US010695330B2

(12) United States Patent
Li et al.

(10) Patent No.: US 10,695,330 B2
(45) Date of Patent: Jun. 30, 2020

(54) METHODS OF TREATMENT

(71) Applicant: Global Blood Therapeutics, Inc., South San Francisco, CA (US)

(72) Inventors: Zhe Li, San Diego, CA (US); Jason R. Harris, South San Francisco, CA (US)

(73) Assignee: Global Blood Therapeutics, Inc., South San Francisco, CA (US)

(*) Notice: Subject to any disclaimer, the term of this patent is extended or adjusted under 35 U.S.C. 154(b) by 0 days.

(21) Appl. No.: 15/981,732

(22) Filed: May 16, 2018

(65) Prior Publication Data

US 2019/0111037 A1 Apr. 18, 2019

Related U.S. Application Data

(63) Continuation of application No. 15/084,252, filed on Mar. 29, 2016, now Pat. No. 10,004,725.

(60) Provisional application No. 62/252,400, filed on Nov. 6, 2015, provisional application No. 62/183,399, filed on Jun. 23, 2015, provisional application No. 62/140,418, filed on Mar. 30, 2015.

(51) Int. Cl.
| *A61K 31/4439* | (2006.01) |
| *A61K 31/4545* | (2006.01) |
| *A61K 31/506* | (2006.01) |
| *A61K 31/497* | (2006.01) |
| *C07D 401/06* | (2006.01) |
| *C07D 403/04* | (2006.01) |
| *A61K 31/455* | (2006.01) |
| *A61K 31/44* | (2006.01) |
| *A61K 31/40* | (2006.01) |

(52) U.S. Cl.
CPC .......... *A61K 31/4439* (2013.01); *A61K 31/40* (2013.01); *A61K 31/44* (2013.01); *A61K 31/455* (2013.01); *A61K 31/4545* (2013.01); *A61K 31/497* (2013.01); *A61K 31/506* (2013.01); *C07D 401/06* (2013.01); *C07D 403/04* (2013.01)

(58) Field of Classification Search
CPC .......... C07D 271/16; C07D 207/08; A61K 31/4439; A61K 31/4545; A61K 31/497; A61K 31/40
USPC ......................................................... 546/340
See application file for complete search history.

(56) References Cited

U.S. PATENT DOCUMENTS

| 3,236,893 | A | 2/1966 | Blout et al. |
|---|---|---|---|
| 4,062,858 | A | 12/1977 | Hoehn et al. |
| 4,410,537 | A | 10/1983 | Kneen |
| 4,478,834 | A | 10/1984 | Shroff et al. |
| 4,535,183 | A | 8/1985 | Kneen |
| 5,185,251 | A | 2/1993 | Chen et al. |
| 5,202,243 | A | 4/1993 | Balani |
| 5,290,941 | A | 3/1994 | Volante et al. |
| 5,403,816 | A | 4/1995 | Takabe et al. |
| 5,679,678 | A | 10/1997 | Binder et al. |
| 5,681,567 | A | 10/1997 | Martinez et al. |
| 5,760,232 | A | 6/1998 | Chen et al. |
| 5,840,900 | A | 11/1998 | Greenwald et al. |
| 5,880,131 | A | 3/1999 | Greenwald et al. |
| 5,965,566 | A | 10/1999 | Greenwald et al. |
| 5,994,353 | A | 11/1999 | Breault |
| 6,011,042 | A | 1/2000 | Greenwald et al. |
| 6,111,107 | A | 8/2000 | Greenwald et al. |
| 6,127,355 | A | 10/2000 | Greenwald et al. |
| 6,153,655 | A | 10/2000 | Martinez et al. |
| 6,194,580 | B1 | 2/2001 | Greenwald et al. |
| 6,214,817 | B1 | 4/2001 | Riley et al. |
| 6,232,320 | B1 | 5/2001 | Stewart et al. |
| 6,242,644 | B1 | 6/2001 | Ackermann et al. |
| 6,355,661 | B1 | 3/2002 | Lai et al. |
| 6,395,266 | B1 | 5/2002 | Martinez et al. |
| 6,608,076 | B1 | 8/2003 | Greenwald et al. |
| 6,630,496 | B1 | 10/2003 | Seehra et al. |
| 7,160,910 | B2 | 1/2007 | Safo et al. |
| 7,411,083 | B2 | 8/2008 | Gopalsamy et al. |
| 8,952,171 | B2 | 2/2015 | Xu et al. |
| 9,012,450 | B2 | 4/2015 | Metcalf et al. |
| 9,018,210 | B2 | 4/2015 | Metcalf et al. |
| 9,248,199 | B2 | 2/2016 | Metcalf et al. |
| 9,422,279 | B2 | 8/2016 | Metcalf et al. |
| 9,447,071 | B2 | 9/2016 | Li et al. |
| 9,458,139 | B2 | 10/2016 | Xu et al. |
| 9,604,999 | B2 | 3/2017 | Harris et al. |
| 9,802,900 | B2 | 10/2017 | Li et al. |
| 9,957,250 | B2 | 5/2018 | Metcalf et al. |
| 1,000,472 | A1 | 6/2018 | Dufu et al. |
| 10,034,879 | B2 | 7/2018 | Metcalf et al. |

(Continued)

FOREIGN PATENT DOCUMENTS

| CN | 101113148 | 1/2008 |
|---|---|---|
| CN | 102116772 | 7/2011 |

(Continued)

OTHER PUBLICATIONS

Abdulmalik et al., "Crystallographic analysis of human hemoglobin elucidates the structural basis of the potent and dual antisickling activity of pyridyl derivatives of vanillin", Acta Cryst. 2011, D67, 920-928.

(Continued)

*Primary Examiner* — Jennifer M Kim

(74) *Attorney, Agent, or Firm* — Sheppard Mullin Richter & Hampton LLP

(57) ABSTRACT

This disclosure relates to use of certain aldehyde compounds for treating pulmonary fibrosis, hypoxia, and connective tissue and autoimmune disease such as scleroderma, lupus, arthritis and related conditions in a mammal.

17 Claims, 49 Drawing Sheets

(56) References Cited

U.S. PATENT DOCUMENTS

| | | |
|---|---|---|
| 10,077,249 B2 | 9/2018 | Li et al. |
| 10,100,040 B2 | 10/2018 | Li et al. |
| 10,100,043 B2 | 10/2018 | Metcalf et al. |
| 10,137,118 B2 | 11/2018 | Li et al. |
| 10,266,551 B2 | 4/2019 | Li et al. |
| 10,377,741 B2 | 8/2019 | Metcalf et al. |
| 10,450,269 B1 | 10/2019 | Xu et al. |
| 2001/0046997 A1 | 11/2001 | Abraham et al. |
| 2002/0095035 A1 | 7/2002 | Warshawsky et al. |
| 2002/0142995 A1 | 10/2002 | Nicolau et al. |
| 2002/0147138 A1 | 10/2002 | Firestone et al. |
| 2003/0022923 A1 | 1/2003 | Lai et al. |
| 2003/0073712 A1 | 4/2003 | Wang et al. |
| 2003/0165714 A1 | 9/2003 | Lee et al. |
| 2003/0187026 A1 | 10/2003 | Li et al. |
| 2003/0190333 A1 | 10/2003 | Mossman et al. |
| 2003/0199511 A1 | 10/2003 | Li et al. |
| 2004/0186077 A1 | 9/2004 | Diakur et al. |
| 2004/0209921 A1 | 10/2004 | Bridger et al. |
| 2005/0085484 A1 | 4/2005 | Mitchell et al. |
| 2005/0159605 A1 | 7/2005 | Tarur et al. |
| 2006/0094761 A1 | 5/2006 | Haque et al. |
| 2008/0114167 A1 | 5/2008 | Castro et al. |
| 2009/0143371 A1 | 6/2009 | Buettelmann |
| 2009/0163512 A1 | 6/2009 | Chen et al. |
| 2009/0312315 A1 | 12/2009 | Yamaguchi et al. |
| 2010/0204235 A1 | 8/2010 | Lizos et al. |
| 2010/0311748 A1 | 12/2010 | Dakin et al. |
| 2013/0018092 A1 | 1/2013 | Stern |
| 2013/0190315 A1 | 7/2013 | Metcalf et al. |
| 2013/0190316 A1 | 7/2013 | Metcalf et al. |
| 2014/0271591 A1 | 9/2014 | Sinha et al. |
| 2014/0274961 A1 | 9/2014 | Metcalf et al. |
| 2014/0275152 A1 | 9/2014 | Metcalf et al. |
| 2014/0275176 A1 | 9/2014 | Xu et al. |
| 2014/0275181 A1 | 9/2014 | Harris et al. |
| 2015/0057251 A1 | 2/2015 | Harris |
| 2015/0133430 A1 | 5/2015 | Xu et al. |
| 2015/0141465 A1 | 5/2015 | Yee et al. |
| 2015/0259296 A1 | 9/2015 | Li et al. |
| 2015/0344472 A1 | 12/2015 | Metcalf et al. |
| 2015/0344483 A1 | 12/2015 | Metcalf et al. |
| 2016/0024127 A1 | 1/2016 | Harris et al. |
| 2016/0038474 A1 | 2/2016 | Sinha et al. |
| 2016/0046613 A1 | 2/2016 | Metcalf et al. |
| 2016/0083343 A1 | 3/2016 | Xu et al. |
| 2016/0083348 A1 | 3/2016 | Xu et al. |
| 2016/0152602 A1 | 6/2016 | Xu et al. |
| 2016/0206604 A1 | 7/2016 | Metcalf et al. |
| 2016/0206614 A1 | 7/2016 | Metcalf et al. |
| 2016/0207904 A1 | 7/2016 | Li et al. |
| 2016/0346263 A1 | 12/2016 | Li et al. |
| 2017/0107199 A1 | 4/2017 | Metcalf et al. |
| 2017/0157101 A1 | 6/2017 | Ramos et al. |
| 2017/0174654 A1 | 6/2017 | Metcalf et al. |
| 2017/0355713 A1 | 12/2017 | Harris et al. |
| 2018/0125789 A1 | 5/2018 | Dalziel et al. |
| 2018/0186807 A1 | 7/2018 | Yee et al. |
| 2018/0201577 A1 | 7/2018 | Xu et al. |
| 2019/0010121 A1 | 1/2019 | Xu et al. |
| 2019/0010176 A1 | 1/2019 | Harris |
| 2019/0106404 A1 | 4/2019 | Li et al. |
| 2019/0111037 A1 | 4/2019 | Li et al. |
| 2019/0112287 A1 | 4/2019 | Metcalf et al. |
| 2019/0160060 A1 | 5/2019 | Metcalf et al. |
| 2019/0202782 A1 | 7/2019 | Xu et al. |
| 2019/0255031 A1 | 8/2019 | Li et al. |

FOREIGN PATENT DOCUMENTS

| | | |
|---|---|---|
| DE | 2238734 | 2/1973 |
| DE | 2238628 | 3/1973 |
| DE | 2853765 | 6/1980 |
| DE | 2904829 | 8/1980 |
| DE | 3503435 | 8/1985 |
| DE | 3431004 | 3/1986 |
| DE | 3704223 | 8/1987 |
| DE | 258226 | 7/1988 |
| DE | 276479 | 2/1990 |
| DE | 3931954 | 3/1990 |
| DE | 4318550 | 12/1994 |
| DE | 4442050 | 5/1996 |
| EP | 010063 | 4/1980 |
| EP | 0268989 | 6/1988 |
| EP | 0278686 | 8/1988 |
| EP | 0291916 | 11/1988 |
| EP | 0303465 | 2/1989 |
| EP | 0336369 | 10/1989 |
| EP | 0348155 | 12/1989 |
| EP | 0401517 | 12/1990 |
| EP | 0453210 | 10/1991 |
| EP | 0462800 | 12/1991 |
| EP | 0481802 | 4/1992 |
| EP | 0498380 | 8/1992 |
| EP | 0528337 | 2/1993 |
| EP | 0542372 | 5/1993 |
| EP | 0567133 | 10/1993 |
| EP | 0637586 | 2/1995 |
| EP | 0640609 | 3/1995 |
| EP | 0747393 | 12/1996 |
| FR | 2909379 | 6/2008 |
| GB | 1593417 | 7/1981 |
| JP | 61-040236 | 2/1986 |
| JP | 06-041118 | 2/1994 |
| JP | 07-025882 | 1/1995 |
| JP | 2006-342115 | 12/2006 |
| JP | 2009-203230 | 9/2009 |
| WO | WO-91/19697 | 12/1991 |
| WO | WO-92/02503 | 2/1992 |
| WO | WO-93/17013 | 9/1993 |
| WO | WO-94/01406 | 1/1994 |
| WO | WO-95/14015 | 5/1995 |
| WO | WO-95/21854 | 8/1995 |
| WO | WO-96/11902 | 4/1996 |
| WO | WO-97/44306 | 11/1997 |
| WO | WO-99/43672 | 9/1999 |
| WO | WO-99/47529 | 9/1999 |
| WO | WO-99/48490 | 9/1999 |
| WO | WO-99/59978 | 11/1999 |
| WO | WO-99/62908 | 12/1999 |
| WO | WO-00/35858 | 6/2000 |
| WO | WO-00/40564 | 7/2000 |
| WO | WO-00/75145 | 12/2000 |
| WO | WO-01/00612 | 1/2001 |
| WO | WO-01/19823 | 3/2001 |
| WO | WO-01/23383 | 4/2001 |
| WO | WO-01/36375 | 5/2001 |
| WO | WO-01/57006 | 8/2001 |
| WO | WO-01/57044 | 8/2001 |
| WO | WO-01/62705 | 8/2001 |
| WO | WO-01/70663 | 9/2001 |
| WO | WO-02/00622 | 1/2002 |
| WO | WO-02/12235 | 2/2002 |
| WO | WO-02/24635 | 3/2002 |
| WO | WO-02/24679 | 3/2002 |
| WO | WO-02/051849 | 7/2002 |
| WO | WO-02/053547 | 7/2002 |
| WO | WO-03/051366 | 6/2003 |
| WO | WO-03/053368 | 7/2003 |
| WO | WO-03/101959 | 12/2003 |
| WO | WO-2004/014899 | 2/2004 |
| WO | WO-2004/018430 | 3/2004 |
| WO | WO-2004/024705 | 3/2004 |
| WO | WO-2004/056727 | 7/2004 |
| WO | WO-2004/058790 | 7/2004 |
| WO | WO-2004/087075 | 10/2004 |
| WO | WO-2005/047249 | 5/2005 |
| WO | WO-2005/074513 | 8/2005 |
| WO | WO-2005/077932 | 8/2005 |
| WO | WO-2005/087766 | 9/2005 |
| WO | WO-2006/011469 | 2/2006 |
| WO | WO-2006/088173 | 8/2006 |
| WO | WO-2006/103463 | 10/2006 |
| WO | WO-2006/106711 | 10/2006 |

(56) References Cited

FOREIGN PATENT DOCUMENTS

| WO | WO-2006/116764 | 11/2006 |
|---|---|---|
| WO | WO-2007/017267 | 2/2007 |
| WO | WO-2007/047204 | 4/2007 |
| WO | WO-2007/049675 | 5/2007 |
| WO | WO-2007/117180 | 10/2007 |
| WO | WO-2008/013414 | 1/2008 |
| WO | WO-2008/016132 | 2/2008 |
| WO | WO-2008/041118 | 4/2008 |
| WO | WO-2008/051532 | 5/2008 |
| WO | WO-2008/060391 | 5/2008 |
| WO | WO-2008/081096 | 7/2008 |
| WO | WO-2008/101682 | 8/2008 |
| WO | WO-2009/001214 | 12/2008 |
| WO | WO-2009/050183 | 4/2009 |
| WO | WO-2009/125606 | 10/2009 |
| WO | WO-2009/130560 | 10/2009 |
| WO | WO-2009/146555 | 12/2009 |
| WO | WO-2010/056631 | 5/2010 |
| WO | WO-2010/129055 | 11/2010 |
| WO | WO-2011/033045 | 3/2011 |
| WO | WO-2011/136459 | 11/2011 |
| WO | WO-2012/141228 | 10/2012 |
| WO | WO-2013/102145 | 7/2013 |
| WO | WO-2014/150261 | 9/2014 |
| WO | WO-2014/150268 | 9/2014 |
| WO | WO-2015/031284 | 3/2015 |
| WO | WO-2015/031285 | 3/2015 |
| WO | WO-2015/120133 | 8/2015 |
| WO | WO-2016/043849 | 3/2016 |

OTHER PUBLICATIONS

Abdulmalik et al., Sickle cell disease: current therapeutic approaches, Expert Opinion Ther. Patents, 2005, vol. 15(11), pp. 1497-1506.
Abraham et al., Vanillin, a Potential Agent for the Treatment of Sickle Cell Anemia, Blood, Mar. 1991, vol. 77 (6), pp. 1334-1341.
Adhikary, P.K., et al., "A new antisickling agent: In vitro studies of its effect on S/S erythrocytes and on hemoglobin S", Experientia. 1978, vol. 34, No. 6, pp. 804-806.
Amendment No. 1 to Form S-1 Registration Statement, Global Blood Therapeutics, Inc., pp. 79 and 88, as filed with the Securities and Exchange Commission on Jul. 31, 2015.
Arya R, et al. "Tucaresol increases oxygen affinity and reduces haemolysis in subjects with sickle cell anaemia," Br. J. Haematol., 93(4):817-21 (1996).
Beddell, Substituted benzaldehydes designed to increase the oxygen affinity of human haemoglobin and inhibit the sickling of sickle erythrocycles, Br. J. Pharmac., 82:397-407, 1984.
Bradbury et al., "New nonpeptide angiotensin II receptor antagonists", Journal of Medicinal Chemistry, 1993, vol. 36, pp. 1245-1254.
Cabrales et al., Abstract 10826: GBT1118, a Potent Allosteric Modifier of Hemoglobin Oxygen Affinity Increases Tolerance to Hypoxia in Mice, Vascular Disease Session Title: The Latest on Lung Injury, downloaded from http://circ.ahajournals.org/content/132/Suppl_3/A10826 (Sep. 27, 2016).
Cabrales et al., GBT1118, A Potent Allosteric Modifier of Hemoglobin Oxygen Affinity Increases Tolerance to Hypoxia in Mice, Poster, 2015.
Chemical Abstract Registry No. 1142191-55-6, indexed in the Registry File on STN CA Online May 4, 2009.
Cherian et al., "Structure-Activity Relationships of Antitubercular Nitroimidazoles 3. Exploration of the Linker and Lipophilic Tail of ((S)-2-Nitro-6,7-dihydro-5H-imidazo[2,1-b][1,3]oxazin-6-yl)-(4-trifluoromethoxybenzyl)amine (6-Amino PA-824).," J. Med. Chem., Aug. 2011, vol. 54(16), pp. 5639-5659.
Database Pubchem Compound Dec. 4, 2011 XP 003033770 (11 pages).
Elwahy, "Synthesis of new benzo-substituted macrocyclic containing quinoxaline subunits" Tetrahedron (2000), 56(6), 897-907 CODEN:TETRAB; ISSN:0040-4020.
Ghate et al., "Synthesis of vanillin ethers from 4-(bromomethyl) coumarins as anti-inflammatory agents," European Journal of Medicinal Chemistry (2003), 38(3), 297-302 CODEN: EJMCAS; ISSN: 0223-5234.
Gibson et al., "Novel small molecule bradykinin B2 receptor antagonists", Journal of Medicinal Chemistry, 2009, vol. 52, pp. 4370-4379.
Grashey, "The nitro group as a 1,3-dipole in cycloadditions" Angewandte Chemie (1962), 74, 155 CODEN: ANCEAD; ISSN: 0044-8249.
International Search Report and Written Opinion for International Application No. PCT/US2016/0024623, dated May 31, 2016. (10 pages).
Lin et al., "Potential Antitumor Agents.8. Derivatives of 3- and 5-Benzyloxy-2-formylpyridine Thiosemicarbazone", Journal of Medicinal Chemistry, American Chemical Society, US, 1972, vol. 15, No. 6, pp. 615-618.
Manna et al., Synthesis and beta-adrenoreceptor blocking activity of [[3-(alkylamine)-2-hydroxypropyl]oximino]pyridines and 0[3-(alkylamine)-2-hydroxypropyl]methylpyridine ketone oximes derivatives, IL FARMACO, 1996, vol. 51, No. 8, 9, pp. 579-587.
Mesguiche et al.,"4-Alkoxy-2,6-diaminopyrimidine Derivatives: Inhibitors of Cyclin Dependent Kinases 1 and 2," Bioorganic & Medicinal Chemistry Letters, Jan. 2003, vol. 13, pp. 217-222.
Nnamani, et al., "Pyridyl derivatives of benzaldehyde as potential antisickling agents," Chem. Biodivers., (2008), 5(9):1762-1769.
PUBCHEM CID 54009805 Create Date: Dec. 4, 2011 p. 1.
PUBCHEM CID 54883281 Create Date: Aug. 19, 2012 p. 1.
Rolan et al., "The pharmacokinetics, tolerability and pharmacodynamics of tucaresol (589C80); 4[2-formyl-3-hydroxyphenoxymethyl] benzoic acid), a potential anti-sickling agent, following oral administration to healthy subjects", British Journal of Clinical Pharmacology, 1993, 35(4):419-425.
Singh et al., "Reductive-Cyclization-Mediated Synthesis of Fused Polycyclic Quinolines from Baylis-Hillman Adducts of Acrylonitrile: Scope and Limitations", European Journal of Organic Chemistry (2009), (20), 3454-3466 CODEN: EJOCFK; ISSN:1434-193X.
Srivastava et al., "Synthesis and biological evaluation of 4-substituted tetrazolo[4,5-a]quinolines and 2,3-disubstituted quinoline derivatives", Indian Journal of Chemistry, Section B: Organic Chemistry Including Medicinal Chemistry (1989), 28B(7), 562-73 CODEN: IJSBOB; ISSN:0376-4699.
Starke et al., "Quinoxalines, Part 13: Synthesis and mass spectrometric study of aryloxymethylquinoxalines and benzo[b]furylquinoxalines" Tetrahedron (2004), 60(29), 6063-6078 CODEN: TETRAB; ISSN:0040-4020.
Wang et al., "Studies of Benzothiophene Template as Potent Factor IXa (FIXa) Inhibitors in Thrombosis", Journal of Medicinal Chemistry (2010), 53, 1465-1472.
Wendt et al., "Synthesis and SAR of 2-aryl pyrido[2,3-d]pyrimidines as potent mGlu5 receptor antagonists", Bioorganic & Medicinal Chemistry Letters, Pergamon, Amsterdam, NL, vol. 17, No. 19, Sep. 14, 2007 (Sep. 14, 2007), pp. 5396-5399.
Zhu et al., "Isoquinoline-pyridine-based protein kinase B/Akt antagonists: SAR and in vivo antitumor activity", Bioorganic & Medicinal Chemistry Letters, Pergamon, Amsterdam, NL, 2006, vol. 16, No. 12, pp. 3150-3155.

Table 1 : Compound 1 hemoximetry

| Structure | Hemox (Whole blood) | |
|---|---|---|
| [chemical structure] | Hct= 20% ([Hb]=1mM) | |
| | %Δp50 (1mM)= 83% | N=1 |
| | | |
| | Hct= 40% ([Hb]=2mM) | |
| | %Δp50 (2mM)= 82% | N=3 |
| | %Δp50 (1.2mM)= 46% | N=3 |
| | %Δp50 (0.6mM)= 22% | N=3 |
| MW= 340.4   cLogP 1.8 | | |

$$\%\Delta p50 = 100 * \left( \frac{(p50 control - p50 sample)}{p50 control} \right)$$

FIG. 1A $$\%\Delta p50 = 100 * \left(\frac{(p50 control - p50 sample)}{p50 control}\right)$$

$$\%\Delta p50 = 100 * \left( \frac{p50 control - p50 sample}{p50 control} \right)$$

Table 5 : Compound 5 hemoximetry

| Structure | Hemox (Whole blood) | |
|---|---|---|
| [Structure image: pyrazole with isopropyl group connected to pyridine, linked via CH2-O to a 2-hydroxybenzaldehyde] <br> MW= 337.4  cLogP 3.2 | Hct= 20% ([Hb]=1mM) | |
| | %Δp50 (1mM)= 80% | N=9 |
| | Hct= 40% ([Hb]=2mM) | |
| | %Δp50 (2mM)= 83% | N=3 |
| | %Δp50 (1.2mM)= 64% | N=3 |
| | %Δp50 (0.6mM)= 30% | N=3 |

$$\%\Delta p50 = 100 * \left( \frac{p50\,control - p50\,sample}{p50\,control} \right)$$

*FIG. 1M*

Table 6 : Compound 6 hemoximetry

| Structure | Hemox (Whole blood) | |
|---|---|---|
| (structure shown; MW= 370.4   cLogP) | | |
| | Hct= 40% ([Hb]=2mM) | |
| | %Δp50 (2mM)= 61% | N=3 |
| | %Δp50 (1.2mM)= 39% | N=3 |
| | 5Δp50 (0.6mM)= 18% | N=3 |

$$\%\Delta p50 = 100 * \left(\frac{p50control - p50sample}{p50control}\right)$$

*FIG. 1P*

Table 7 : Compound 7 hemoximetry $$\%\Delta p50 = 100 * \left( \frac{p50\,control - p50\,sample}{p50\,control} \right)$$

Table 8 : Compound 8 hemoximetry

| Structure | Hemox (Whole blood) | |
|---|---|---|
| [structure of compound 8] | | |
| | Hct= 40% ([Hb]=2mM) | |
| | %Δp50 (2mM)= 70% | N=3 |
| | %Δp50 (1.2mM)= 48% | N=3 |
| | %Δp50 (0.6mM)= 21% | N=3 |
| MW= 370.4    cLogP | | |

$$\%\Delta p50 = 100 * \left(\frac{(p50 control - p50 sample)}{p50 control}\right)$$

FIG. 1V

Table 9 : Compound 9 hemoximetry $$\%\Delta p50 = 100 * \left(\frac{(p50control - p50sample)}{p50control}\right)$$

Table 10 : Compound 10 hemoximetry

| Structure | Hemox (Whole blood) | |
|---|---|---|
| [structure of compound 10] MW= 338.4   cLogP 2.3 | Hct= 20% ([Hb]=1mM) | |
| | Δp50% (1mM)= 75% | N=1 |

$$\%\Delta p50 = 100 * \left(\frac{p50\,control - p50\,sample}{p50\,control}\right)$$

*FIG. 1AB*

Table 11 : Compound 11 hemoximetry

| Structure | Hemox (Whole blood) | |
|---|---|---|
| (structure shown; MW= 354.4, cLogP) | Hct= 40% ([Hb]=2mM) | |
| | %Δp50 (2mM)= 81% | N=3 |
| | %Δp50 (1.2mM)= 63% | N=3 |
| | %Δp50 (0.6mM)= 19% | N=3 |

$$\%\Delta p50 = 100 * \left( \frac{p50control - p50sample}{p50control} \right)$$

Table 12 : PK of Compound 1

| Day 15 terminal blood (N=12) | Whole blood Compound 1 (μM) | Plasma Compound 1 (μM) | Blood/Plasma ratio | Calculated Hb Occupancy (%) |
|---|---|---|---|---|
| Low dose: Day8: 50mg/kg; Day9-15: 40mg/kg | 195.5 | 8.4 | 23.2 | 18.0 |
| High dose: Day8: 150mg/kg; Day9-15: 85mg/kg | 400.2 | 18.9 | 21.2 | 36.7 |

FIG. 4A

METHODS OF TREATMENT

CROSS-REFERENCE TO RELATED APPLICATIONS

This application is a continuation of U.S. patent application Ser. No. 15/084,252, filed Mar. 29, 2016, now U.S. Pat. No. 10,004,725, which application claims priority to U.S. Provisional Application Nos. 62/140,418, filed Mar. 30, 2015, 62/183,399, filed Jun. 23, 2015, and 62/252,400, filed Nov. 6, 2015, the contents of which are hereby incorporated by reference in their entireties into this application.

FIELD

Provided herein are aldehyde compounds for use in treating diseases such as pulmonary fibrosis, hypoxia, and connective tissue and autoimmune disease such as scleroderma, lupus, arthritis and related conditions in a mammal.

BACKGROUND

Idiopathic pulmonary fibrosis (IPF) is a deadly lung disease that causes chronic, progressive, and irreversible fibrosis in the lungs. It is characterized by alveolar damage and exaggerated fibrous tissue production that results in obliteration of lung parenchyma and subsequent lung dysfunction (see Wilson, M. S. and T. A. Wynn (2009). "Pulmonary fibrosis: pathogenesis, etiology and regulation." *Mucosal Immunol* 2(2): 103-121). Currently, around 5 million people worldwide are affected by IPF with over 128,000 patients in the United States with a median survival time of approximately 2.5 years from the time of diagnosis (see Raghu, G., D. Weycker, J. Edelsberg, W. Z. Bradford and G. Oster (2006). "Incidence and prevalence of idiopathic pulmonary fibrosis." *Am J Respir Crit Care Med* 174(7): 810-816). Although two anti-fibrotic drugs, pirfenidone and nintedanib, have been approved for the treatment of IPF, treatment options are still limited for this severe disease (see Harari, S. and A. Caminati (2015). "Idiopathic pulmonary fibrosis: from clinical trials to real-life experiences." *Eur Respir Rev* 24(137): 420-427).

Hypoxemia and hypoxia arise in patients with IPF because the body (or a tissue, or a cell) is deprived of oxygen One of the clinical manifestations of hypoxia is exertional breathlessness for which there are no available drugs to date (see Baddini Martinez, J. A., T. Y. Martinez, F. P. Lovetro Galhardo and C. A. de Castro Pereira (2002). "Dyspnea scales as a measure of health-related quality of life in patients with idiopathic pulmonary fibrosis." *Med Sci Monit* 8(6): CR405-410; see also Parshall, M. B., R. M. Schwartzstein, L. Adams, R. B. Banzett, H. L. Manning, J. Bourbeau, P. M. Calverley, A. G. Gift, A. Harver, S. C. Lareau, D. A. Mahler, P. M. Meek, D. E. O'Donnell and D. American Thoracic Society Committee on (2012). "An official American Thoracic Society statement: update on the mechanisms, assessment, and management of dyspnea." *Am J Respir Crit Care Med* 185(4): 435-452).

Oxygen deprivation resulting from hypoxemia and/or hypoxia can, in turn, cause severe organ damage and even death. Therefore, there continues to be a significant need for drugs useful in the treatment of above diseases or conditions.

SUMMARY

Oxygen loading of hemoglobin is compromised in many conditions, including lung diseases that result in decreased oxygen diffusion in the lungs, such as Idiopathic pulmonary fibrosis (IPF), or with increased altitude (i.e., low alveolar oxygen availability). The compounds provided and/or disclosed herein increase hemoglobin oxygen affinity and improve oxygen uptake under hypoxic conditions or diseases where the lungs lose their ability to transfer oxygen into the bloodstream (such as IPF and lung injury) and increase delivery of oxygen to cells and tissues.

Additionally, in a well-established mouse IPF model (see Degryse, A. L. and W. E. Lawson (2011). "Progress toward improving animal models for idiopathic pulmonary fibrosis." *Am J Med Sci* 341(6): 444-449; Moore, B. B., W. E. Lawson, T. D. Oury, T. H. Sisson, K. Raghavendran and C. M. Hogaboam (2013). "Animal models of fibrotic lung disease." *Am J Respir Cell Mol Biol* 49(2): 167-179), Applicant studied the ability of (S)-2-hydroxy-6-((1-nicotinoylpiperidin-2-yl)methoxy)benzaldehyde (Compound 1) to ameliorate hypoxemia associated with lung fibrosis induced by bleomycin, and unexpectedly discovered that Compound 1 not only significantly improved hypoxemia, but also attenuated pulmonary inflammation and pulmonary fibrosis.

Without being bound by any theory, it is believed that Compound 1 binds covalently and reversibly via Schiff base to the N-terminal valine of the hemoglobin (Hb) alpha chain and allosterically modulates the Hb-oxygen (Hb-$O_2$) affinity. Without being bound by any theory, it also believed that Compound 1 elicits a concentration-dependent left shift in the oxygen equilibrium curve with subsequent increase in Hb-$O_2$ affinity and arterial oxygen loading. Accordingly, besides treating hypoxemia, compounds that increase Hb-$O_2$ affinity could be useful in the treatment of pulmonary fibrosis including inflammation associated therewith and also in the treatment of connective tissue and autoimmune diseases such as scleroderma, lupus, rheumatoid arthritis, polymyositis and dermatomyositis.

Accordingly, in a first aspect, provided herein is a method of treating pulmonary fibrosis in a patient in need thereof, comprising administering to the patient a therapeutically effective amount of a compound described herein. In one embodiment of the first aspect, the pulmonary fibrosis is lung fibrosis. In other embodiment, the pulmonary fibrosis is lung fibrosis. In yet another embodiment, the lung fibrosis is fibrosing mediastinitis.

In a second embodiment of the first aspect, the pulmonary fibrosis is idiopathic, e.g., IPF.

In a third embodiment of the first aspect, the pulmonary fibrosis is caused by the use of certain medicines, including, for example, certain chemotherapeutic drugs (e.g., methotrexate and cyclophosphamide), heart medications (e.g., amiodarone and propranolol), and antibiotics (e.g., nitrofurantoin and sulfasalazine). In a fourth embodiment of the first aspect, the pulmonary fibrosis is caused by inhalation exposure to environmental and occupational pollutants, including, for example, asbestos, silica, and hard metal dusts. In a fifth embodiment of the first aspect, the pulmonary fibrosis is caused by connective tissue diseases, including, for example, systemic lupus erythematosus, rheumatoid arthritis, and scleroderma. In a sixth embodiment of the first aspect, the pulmonary fibrosis is caused by inflammatory diseases, including, for example, sarcoidosis. In a seventh embodiment of the first aspect, the pulmonary fibrosis is caused by bacterial or viral infections, including, for example, tuberculosis, and pneumonia.

In another aspect, provided herein is a method of treating inflammation associated with pulmonary fibrosis in a patient in need thereof, comprising administering to the patient a therapeutically effective amount of a compound described herein. In one embodiment of this aspect, the pulmonary fibrosis is idiopathic, e.g., IPF.

In yet another aspect, provided herein is a method of treating hypoxia in a patient, comprising administering to the patient a therapeutically effective amount of a compound described herein. In one embodiment of this aspect, the patient is in need of such treatment and the patient is suffering from IPF.

In yet another aspect, provided herein is a method of increasing oxygen saturation of arterial blood in a patient with hypoxia, comprising administering to the patient a therapeutically effective amount of a compound described herein. In one embodiment of this aspect, the patient is in need of such treatment.

In yet another aspect, provided herein is a method of improving oxygen delivery to a tissue or a cell of a patient with hypoxia, comprising administering to the patient a therapeutically effective amount of a compound described herein. In one embodiment of this aspect, the patient is in need of such treatment and is suffering from IPF. In another embodiment of this aspect, the patient has been or will be exposed to high altitude. In yet another embodiment of this aspect, the patient is suffering from high altitude hypoxia. In yet another embodiment of this aspect, the patient with hypoxia has been or will be diving underwater. In yet another embodiment of this aspect, the patient is suffering from deep or shallow water blackout.

In yet another aspect, provided herein is a method for increasing oxygen uptake in the lungs of patients with acidosis in the fluids accumulated in lungs, comprising administering to the patient a therapeutically effective amount of a compound described herein. In one embodiment of this aspect, the patient is in need of such treatment.

In yet another aspect, provided herein is a method of reducing lactate build-up in a tissue or a cell of a patient with hypoxia, comprising administering to the patient a therapeutically effective amount of a compound described herein. In one embodiment of this aspect, the patient is in need of such treatment.

In yet another aspect, provided herein is a method of reducing acidosis of arterial blood of a patient with hypoxia, comprising administering to the patient a therapeutically effective amount of a compound described herein. In one embodiment of this aspect, the patient is in need of such treatment.

In one embodiment of the above aspects, the hypoxia is acute hypoxia. In another embodiment, the hypoxia is chronic hypoxia.

In one embodiment of the above aspects, the hypoxia is caused by decreased oxygen uptake in the lungs. In one embodiment, the hypoxia is caused by lung disease, such as acute respiratory distress syndrome (ARDS), chronic obstructive pulmonary disease (COPD), emphysema, bronchitis, pulmonary edema, cystic fibrosis of the lungs, asthma, pneumonia, rheumatoid lung disease, acute lung injury (e.g., caused by multi-organ dysfunction syndrome (MODS), ventilator-associated lung injury, smoke-inhalation induced lung injury, or chemical or thermal burn to the lungs), or IPD. In one embodiment, the hypoxia is caused by lung cancer. In one embodiment, the hypoxia is caused by pulmonary venous thromboembolism, heart failure, pulmonary hypertension, or congestive heart failure. In one embodiment, the hypoxia is caused by sleep disordered breathing, for example, obstructive sleep apnea and central sleep apnea. In one embodiment, the hypoxia is caused by altitude sickness. In some embodiments, the hypoxia is caused by IPF.

In one embodiment, the ARDS results at least in part from one or more of: breathing vomit into the lungs (aspiration), inhaling chemicals, lung transplantation, pneumonia, septic shock (for example, from infection throughout the body), and trauma.

Without being bound by theory, it is believed that the co-treatment of a patient who is undergoing therapy that decreases red blood cell (RBC) count with the compounds described herein and a composition or treatment regimen for increasing RBCs results in a better reduction of symptoms, e.g., hypoxia. For example, patients with cancer may be treated by radiation or chemotherapy that results in pulmonary toxicity and/or decreased RBC count. In one embodiment, treatment of a patient with a compound as described herein is in combination with a composition or treatment regimen for increasing red blood cells in a patient. In one embodiment, the cancer treatment is a chemotherapy drug which induces pulmonary toxicity, non-limiting examples of which include etoposide, cyclophosphamide, chlorambucil, busulfan, and bleomycin.

In one embodiment, the hypoxia is characterized by a partial oxygen pressure of less than 80 mm Hg, preferably, less than 60 mm Hg, more preferably less than 40 mm Hg, and yet more preferably less than 20 mm Hg.

In one embodiment, the method provided herein further comprises administering one or more of an anti-infective agent such as an antibiotic, an anti-inflammatory agent, an anti-fibrotic such as pirfenidone or nintedanib, an antioxidant, a sedative, and an agent that helps remove fluid from the lungs such as a surfactant.

In yet another aspect, provided herein is a pharmaceutically acceptable composition comprising a compound described herein. In one embodiment, the pharmaceutically acceptable composition comprises at least one pharmaceutically acceptable excipient. In one embodiment, at least one of the pharmaceutically acceptable excipient is a carrier or a diluent. In one embodiment, the injectable composition further comprises water and a pH adjusting agent.

In one embodiment, the pharmaceutically acceptable composition is a parenteral composition. In one embodiment, the pharmaceutically acceptable composition is an injectable composition.

Other aspects and embodiments are provided herein.

BRIEF DESCRIPTION OF THE DRAWINGS

FIG. 1M (TABLE 5) shows a summary of the effects of compound 5 on Hb $O_2$ affinity in whole blood.

FIG. 1P (TABLE 6) shows a summary of the effects of compound 6 on Hb $O_2$ affinity in whole blood.

FIG. 1V (TABLE 8) shows a summary of the effects of compound 8 on Hb $O_2$ affinity in whole blood.

FIG. 1AA illustrates the Bohr Effect of compound 9 in whole blood.

FIG. 1AB (TABLE 10) shows a summary of the effects of compound 10 on Hb $O_2$ affinity in whole blood.

FIG. 1AC illustrates the effect of compound 10 on Hb $O_2$ affinity in whole blood.

FIG. 1AD (TABLE 11) shows a summary of the effects of compound 11 on Hb $O_2$ affinity in whole blood.

FIG. 1AE illustrates the effect of compound 11 on Hb $O_2$ affinity in whole blood.

FIG. 1AF illustrates the Bohr Effect of compound 11 in whole blood.

FIGS. 1AG and 1AH show effects of compound 1 on oxidative burst in activated neutrophils.

FIGS. 1AI, 1AJ, and 1AK show effects of compound 1 on production of TNF-α and IL-6 by macrophages.

FIG. 4A (TABLE 12) summarizes the PK of compound 1 in mice.

Figure 1B:
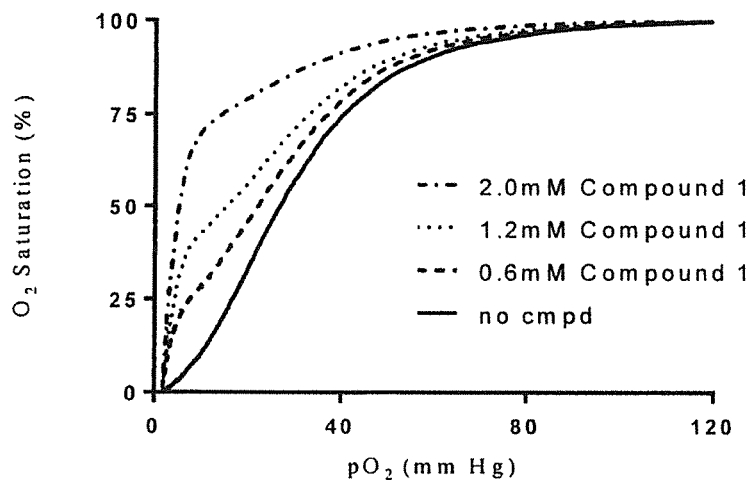
FIG. 1B illustrates the effect of compound 1 on Hb $O_2$ affinity in whole blood.
Figure 1C:
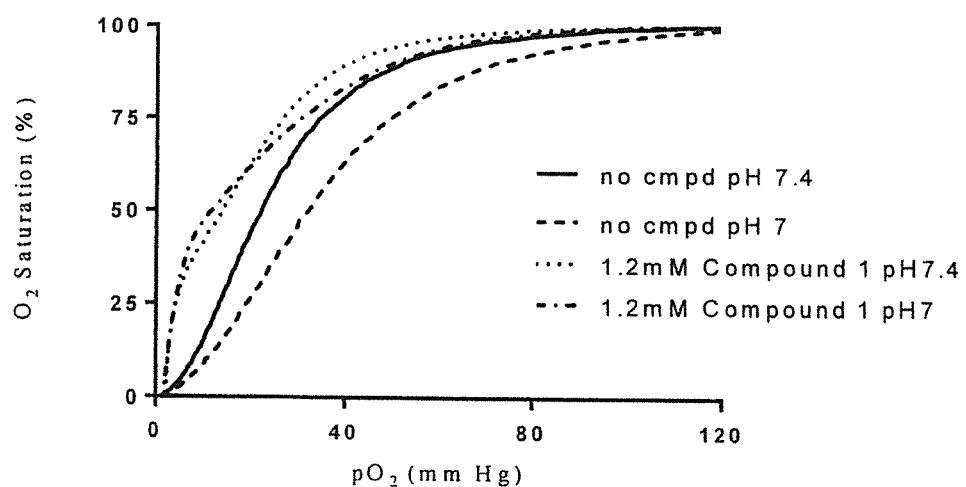
FIG. 1C illustrates the Bohr Effect of compound 1 in whole blood.
Figure 1D:
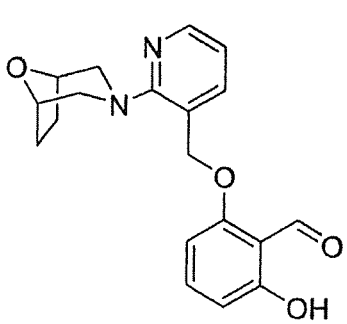
FIG. 1D (TABLE 2) shows a summary of the effects of compound 2 on Hb $O_2$ affinity in whole blood.
Figure 1E:
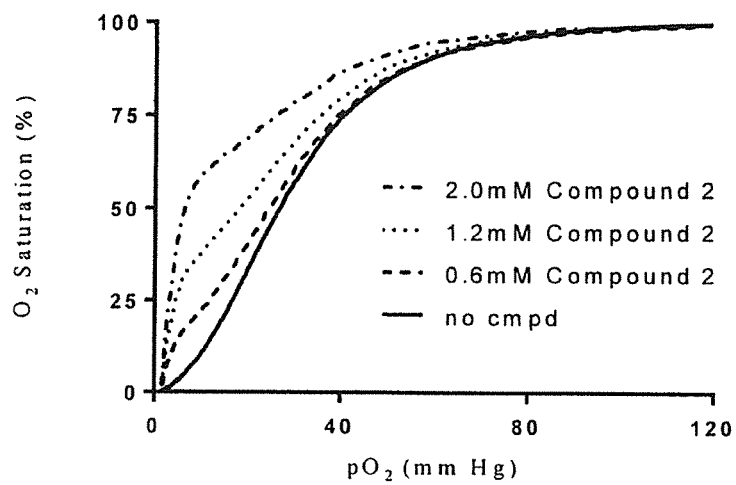
FIG. 1E illustrates the effect of compound 2 on Hb $O_2$ affinity in whole blood.
Figure 1F:
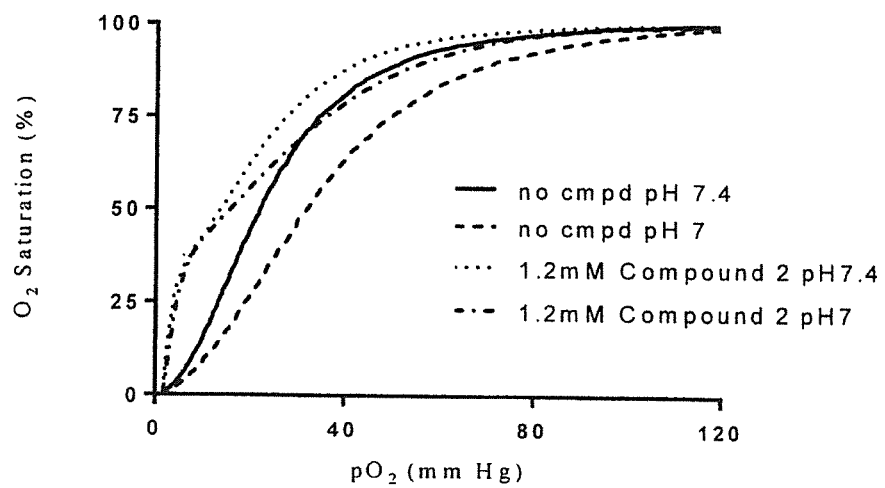
FIG. 1F illustrates the Bohr Effect of compound 2 in whole blood.
Figure 1G:
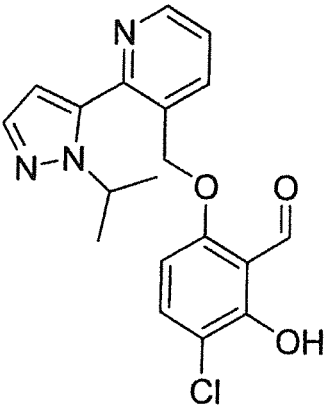
FIG. 1G (TABLE 3) shows a summary of the effects of compound 3 on Hb $O_2$ affinity in whole blood.
Figure 1H:
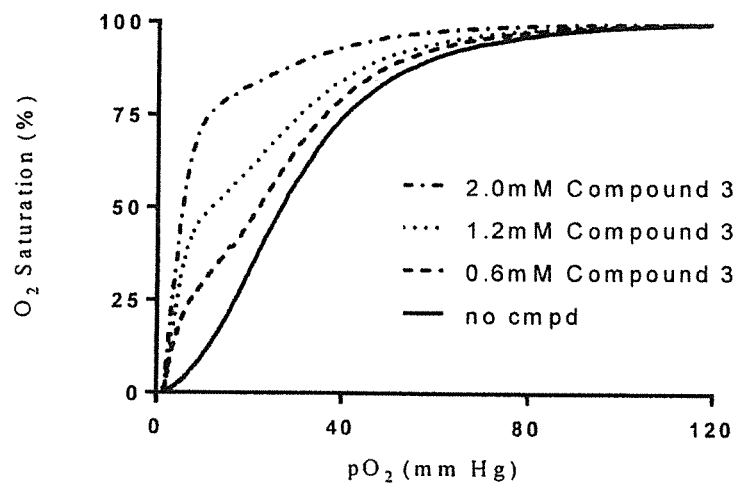
FIG. 1H illustrates the effect of compound 3 on Hb $O_2$ affinity in whole blood.
Figure 1I:
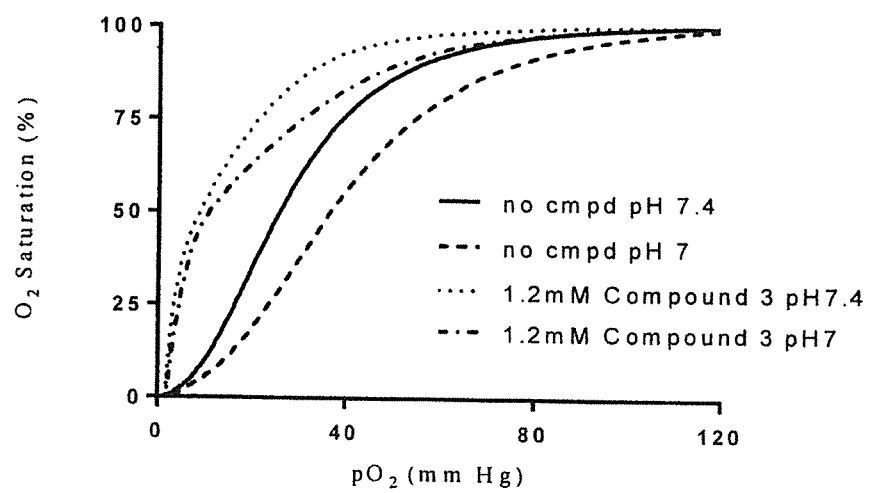
FIG. 1I illustrates the Bohr Effect of compound 3 in whole blood.
Figure 1J:
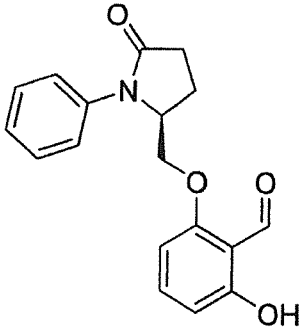
FIG. 1J (TABLE 4) shows a summary of the effects of compound 4 on Hb $O_2$ affinity in whole blood.
Figure 1K:
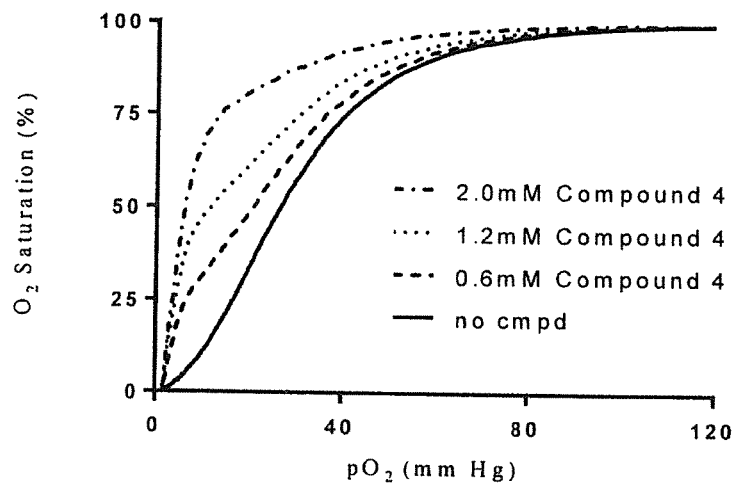
FIG. 1K illustrates the effect of compound 4 on Hb $O_2$ affinity in whole blood.
Figure 1L:
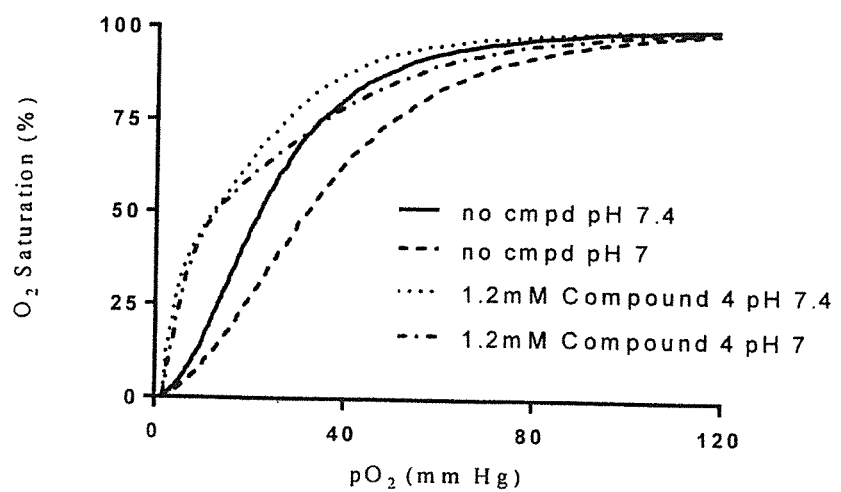
FIG. 1L illustrates the Bohr Effect of compound 4 in whole blood.
Figure 1N:
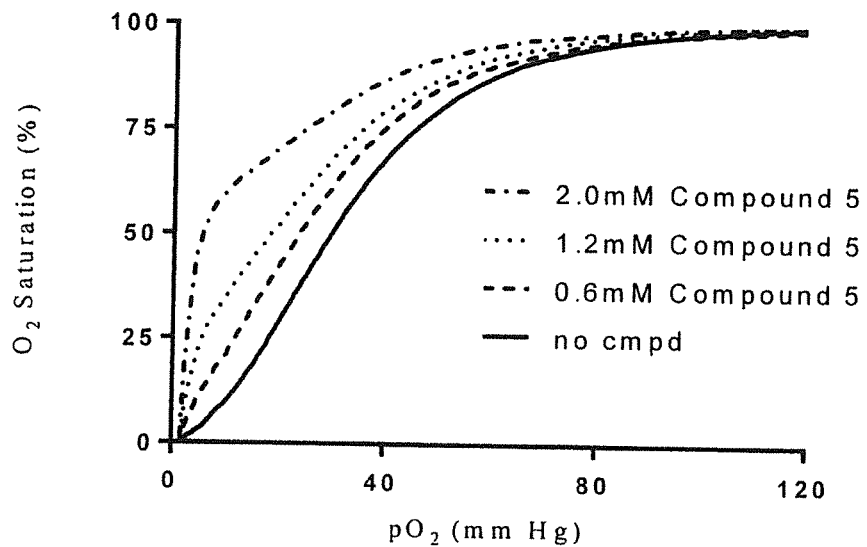
FIG. 1N illustrates the effect of compound 5 on Hb $O_2$ affinity in whole blood.
Figure 1O:
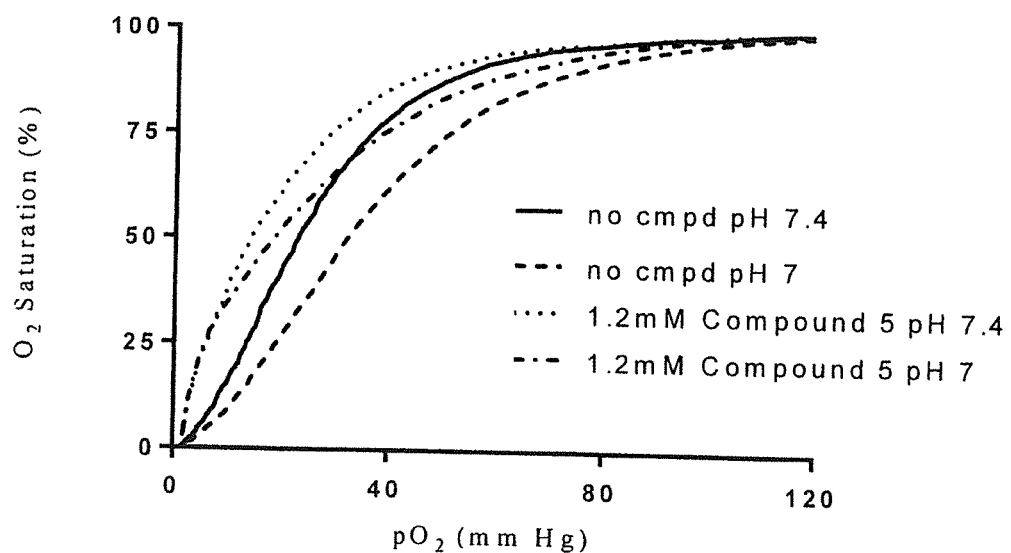
FIG. 1O illustrates the Bohr Effect of compound 5 in whole blood.
Figure 1Q:
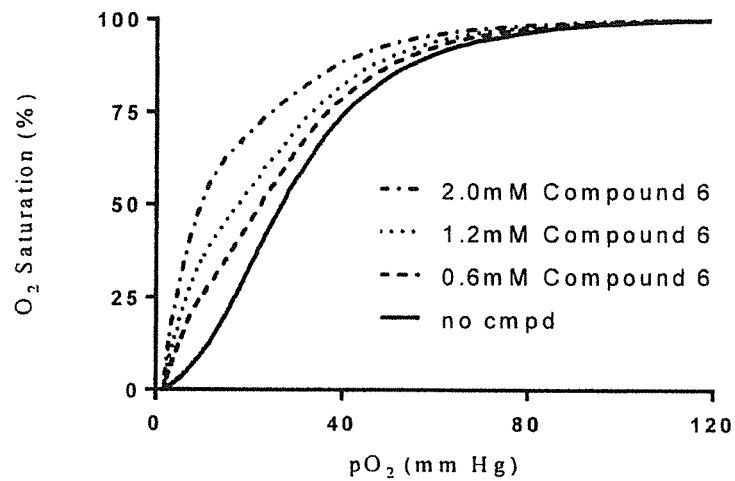
FIG. 1Q illustrates the effect of compound 6 on Hb $O_2$ affinity in whole blood.
Figure 1R:
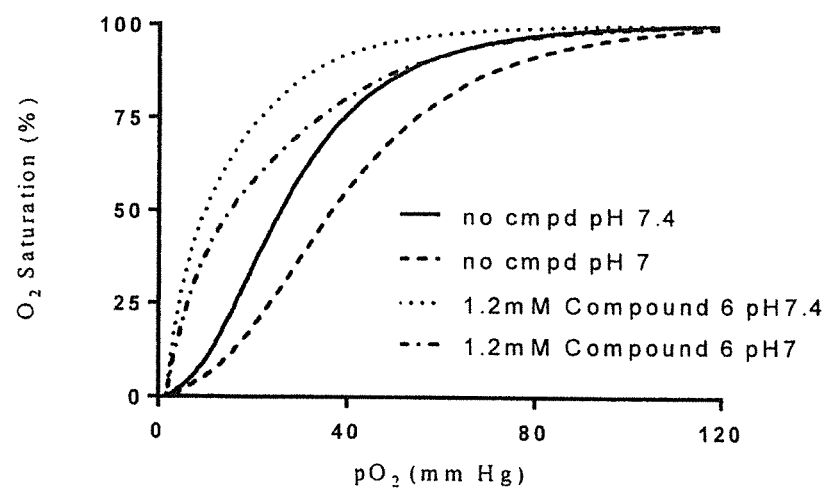
FIG. 1R illustrates the Bohr Effect of compound 6 in whole blood.
Figure 1S:
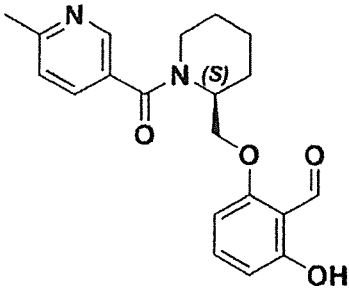
FIG. 1S (TABLE 7) shows a summary of the effects of compound 7 on Hb $O_2$ affinity in whole blood.
Figure 1T:
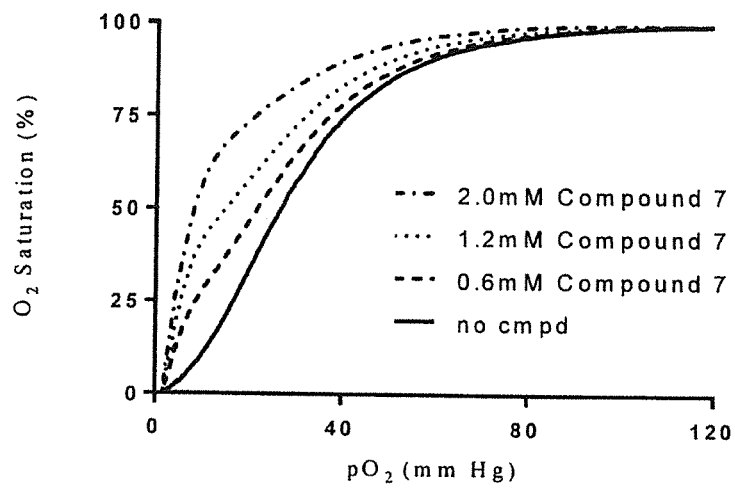
FIG. 1T illustrates the effect of compound 7 on Hb $O_2$ affinity in whole blood.
Figure 1U:
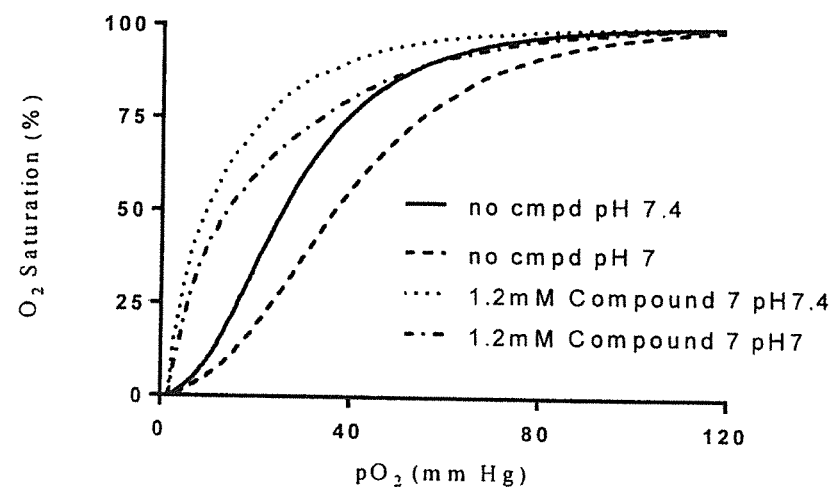
FIG. 1U illustrates the Bohr Effect of compound 7 in whole blood.
Figure 1W:
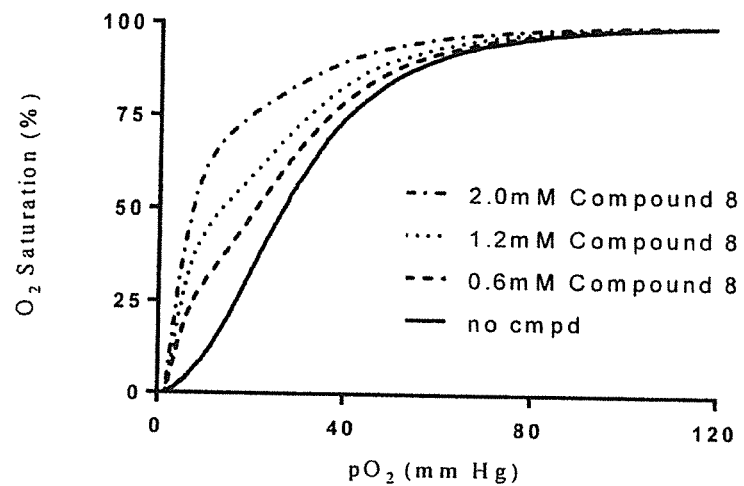
FIG. 1W illustrates the effect of compound 8 on Hb $O_2$ affinity in whole blood.
Figure 1X:
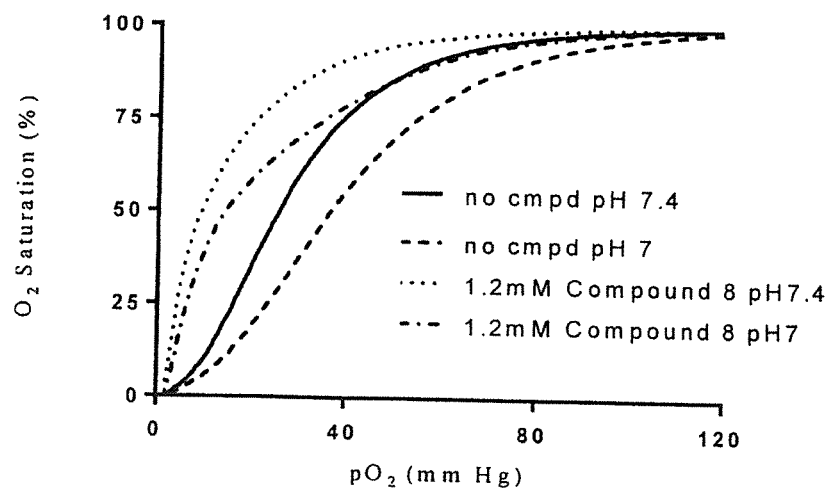
FIG. 1X illustrates the Bohr Effect of compound 8 in whole blood.
Figure 1Y:
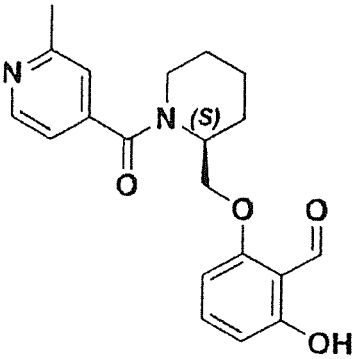
FIG. 1Y (TABLE 9) shows a summary of the effects of compound 9 on Hb $O_2$ affinity in whole blood.
Figure 1Z:
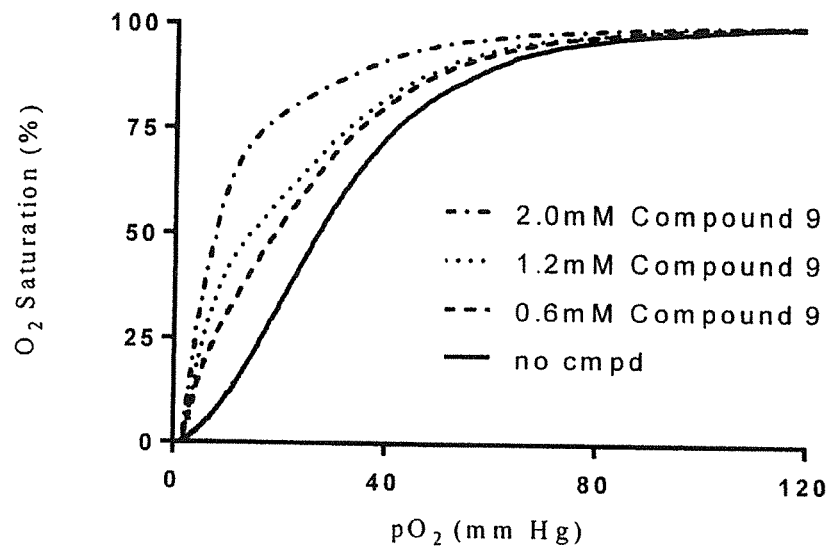
FIG. 1Z illustrates the effect of compound 9 on Hb $O_2$ affinity in whole blood.
Figure 1A:
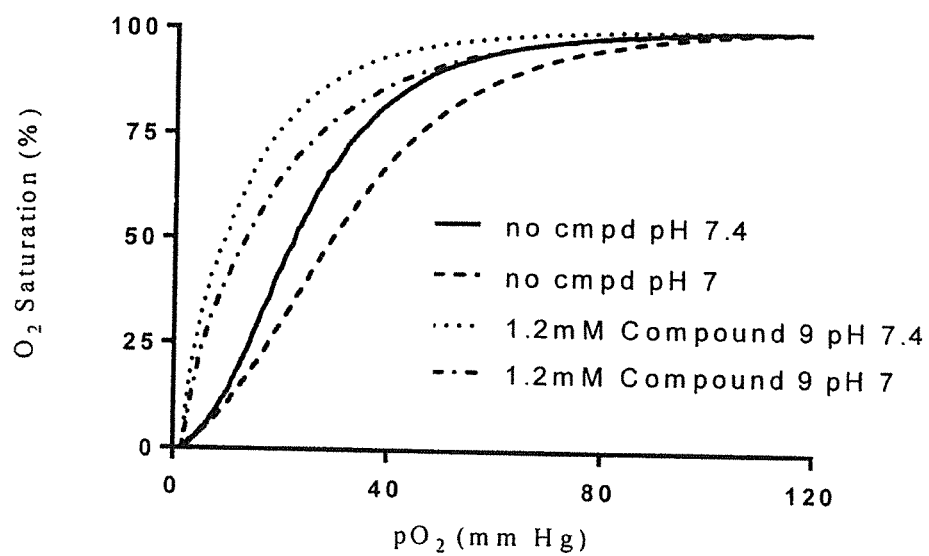
FIG. 1A (TABLE 1) shows a summary of the effects of compound 1 on Hb $O_2$ affinity in whole blood.
Figure 1A:
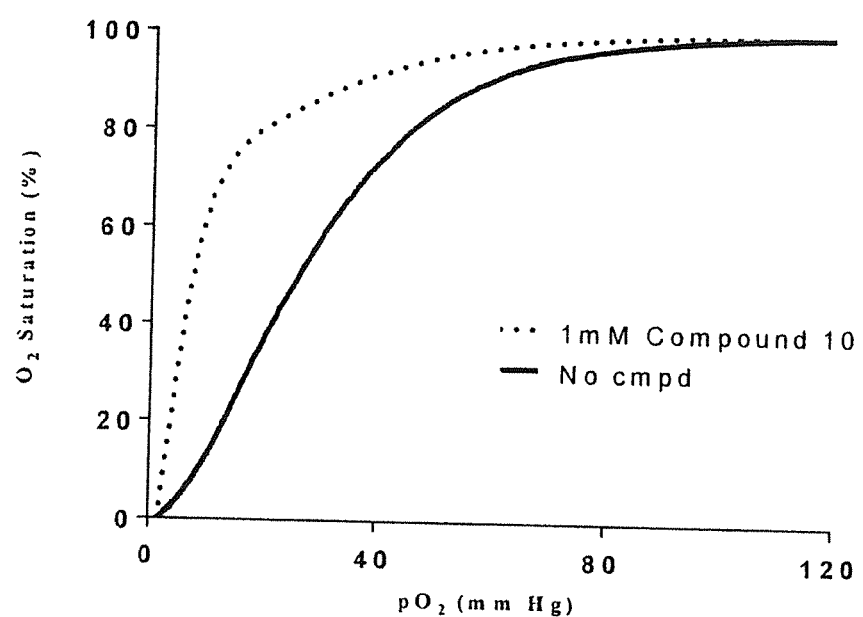
Figure 1A:
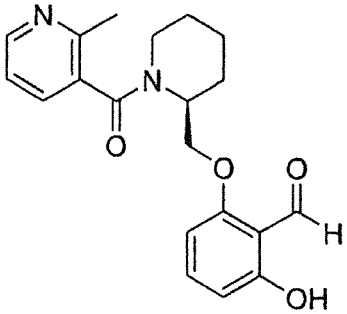
Figure 1A:
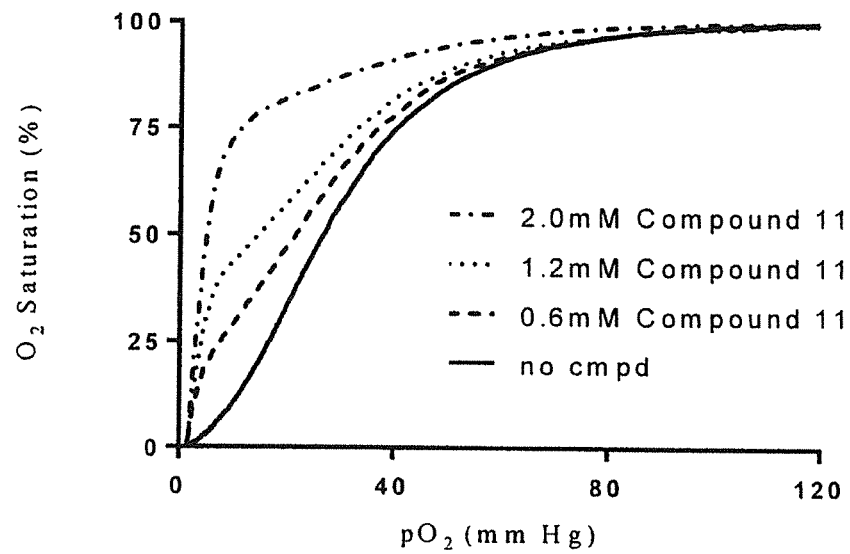
Figure 1A:
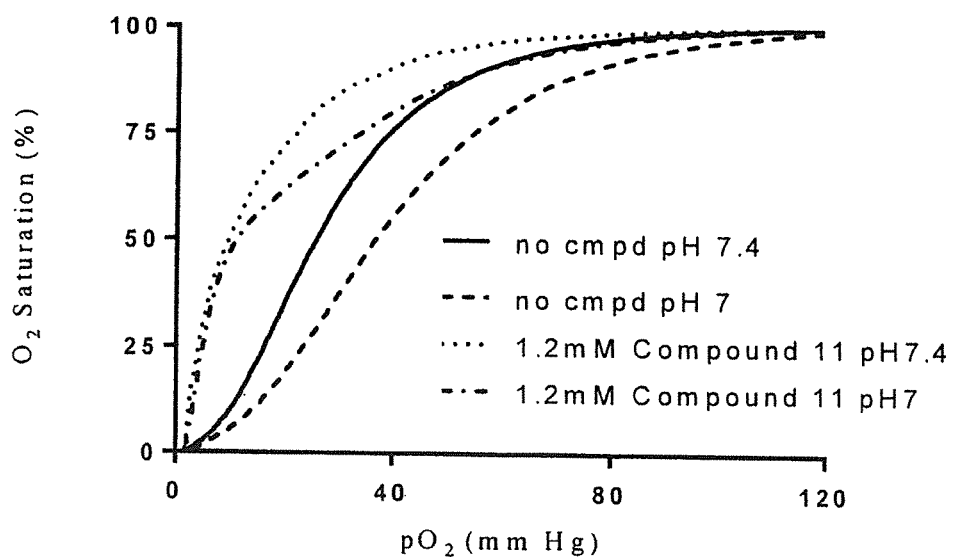
Figure 1A:
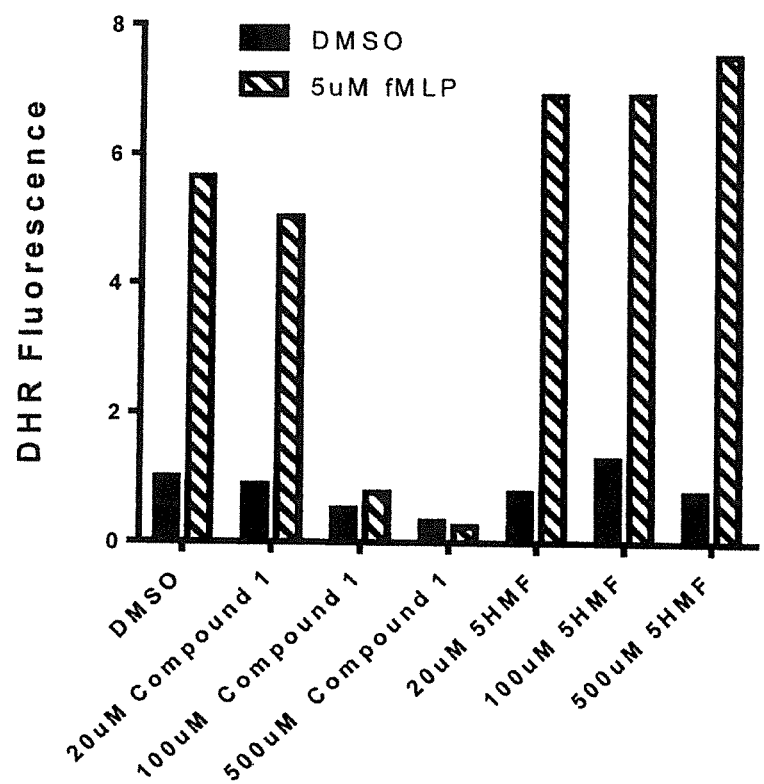
Figure 1A:
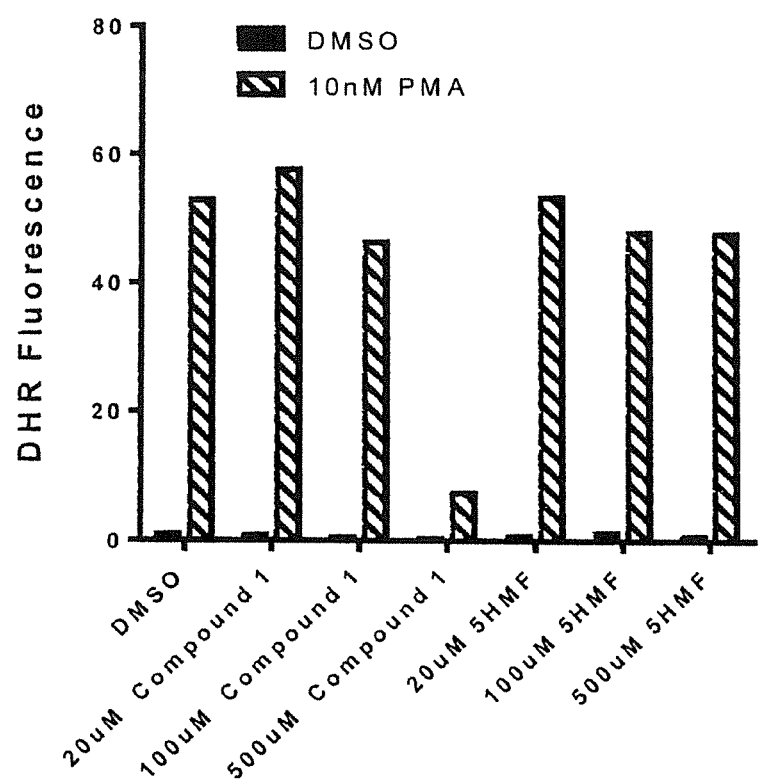
Figure 1A:
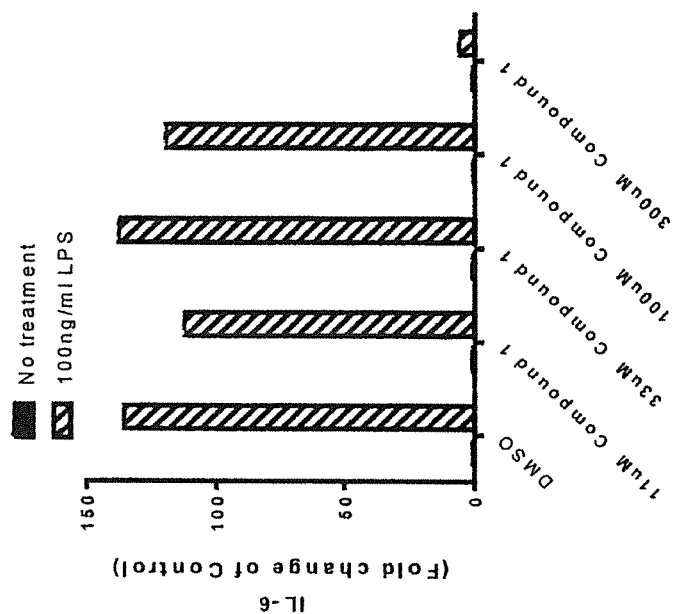
Figure 1A:
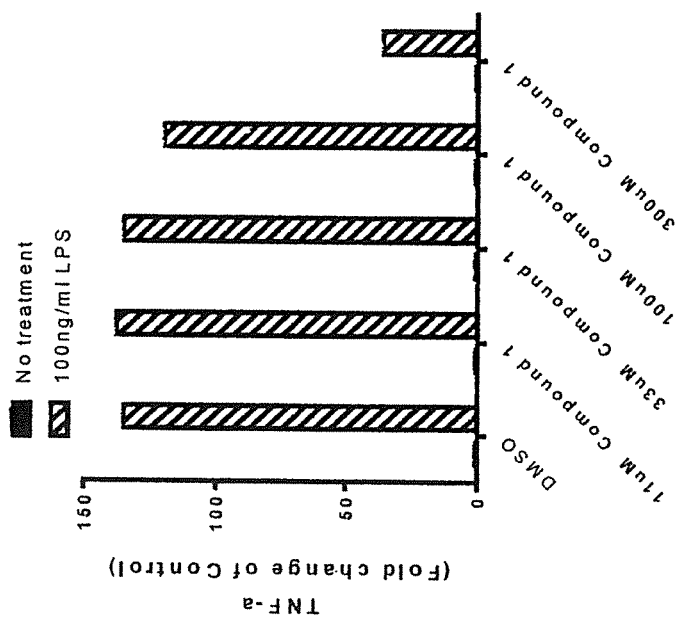

TABLES 1-12 are included in FIGS. 1A (TABLE 1), 1D (TABLE 2), 1G (TABLE 3), 1J (TABLE 4), 1M (TABLE 5), 1P (TABLE 6), 1S (TABLE 7), 1V (TABLE 8), 1Y (TABLE 9), 1AB (TABLE 10), 1AD (TABLE 11), and 4A (TABLE 12).

DETAILED DESCRIPTION

Definitions

It must be noted that as used herein and in the appended claims, the singular forms "a", "an", and "the" include plural referents unless the context clearly dictates otherwise.

As used herein, the term "hypoxia" refers to insufficient oxygen. Hypoxia, as used herein, includes hypoxemia (low blood oxygen), as well as low oxygen in a cell or one or more tissues/organs.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition or process consisting essentially of the elements as defined herein would not exclude other materials or steps that do not materially affect the basic and novel characteristic(s) of the aspects and embodiments provided herein. "Consisting of" shall mean excluding more than trace elements of other ingredients and substantial method steps. Embodiments defined by each of these transition terms are within the scope of the present disclosure.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques. The term "about" when used before a numerical designation, e.g., temperature, time, amount, and concentration, including range, indicates approximations which may vary by (+) or (−) 10%, 5% or 1%.

"Patient" refers to a mammal, preferably, a human.

The term "pharmaceutically acceptable" refers to generally safe and non-toxic for in vivo, preferably, human administration.

The term "pharmaceutically acceptable salt" refers to a salt that is pharmaceutically acceptable. Any compound described herein may be administered as a pharmaceutically acceptable salt.

The term "salt" refers to an ionic compound formed between an acid and a base. When the compound provided herein contains an acidic functionality, such salts include, without limitation, alkali metal, alkaline earth metal, and ammonium salts. As used herein, ammonium salts include, salts containing protonated nitrogen bases and alkylated nitrogen bases. Exemplary and non-limiting cations useful in pharmaceutically acceptable salts include Na, K, Rb, Cs, $NH_4$, Ca, Ba, imidazolium, and ammonium cations based on naturally occurring amino acids. When the compounds utilized herein contain basic functionality, such salts include, without limitation, salts of organic acids, such as carboxylic acids and sulfonic acids, and mineral acids, such as hydrogen halides, sulfuric acid, phosphoric acid, and the likes. Exemplary and non-limiting anions useful in pharmaceutically acceptable salts include oxalate, maleate, acetate, propionate, succinate, tartrate, chloride, sulfate, bisulfate, mono-, di-, and tribasic phosphate, mesylate, tosylate, and the likes.

The terms "treat", "treating" or "treatment", as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting or suppressing the development of the disease or condition, relieving the disease or condition, causing regression of the disease or condition, relieving a condition caused by the disease or condition, or suppressing the symptoms of the disease or condition, and are intended to include prophylaxis. The terms also include relieving the disease or conditions, e.g., causing the regression of clinical symptoms. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made.

The terms "preventing" or "prevention" refer to a reduction in risk of acquiring a disease or disorder (i.e., causing at least one of the clinical symptoms of the disease not to develop in a subject that may be exposed to or predisposed to the disease but does not yet experience or display symptoms of the disease). The terms further include causing the clinical symptoms not to develop, for example in a subject at risk of suffering from such a disease or disorder, thereby substantially averting onset of the disease or disorder.

The term "therapeutically effective amount" refers to an amount that is effective for the treatment of a condition or disorder by a compound or composition described herein. In some embodiments, an effective amount of any of the compounds, compositions or dosage forms described herein is the amount used to treat hypoxia or a hypoxia-associated condition, or to reduce one or more of its negative effects in a patient in need thereof. In other embodiments, an effective amount of any of the compounds described herein is the amount used to treat fibrosis and/or inflammation in IPF, or to reduce one or more of its negative effects in a patient in need thereof.

A "hypoxia-associated condition" is any disease or condition that contributes to or results from hypoxia in a patient. Exemplary hypoxia-associated conditions are described herein.

As used herein, a "prodrug" is a compound that, after administration, is metabolized or otherwise converted to an active or more active form with respect to at least one property. To produce a prodrug, a pharmaceutically active compound can be modified chemically to render it less active or inactive, but the chemical modification is such that an active form of the compound is generated by metabolic or other biological processes. A prodrug may have, relative to the drug, altered metabolic stability or transport characteristics, fewer side effects or lower toxicity. For example, see Nogrady, 1985, Medicinal Chemistry A Biochemical Approach, Oxford University Press, New York, pages 388-392. Prodrugs can also be prepared using compounds that are not drugs.

As used herein, "hemoglobin A" refers to adult hemoglobin, or α2β2, the primary hemoglobin type found in normal adults. Without being bound by theory, it is believed that hypoxemic pulmonary diseases or altitudinal hypoxia and related diseases that are treated by the methods and compounds described herein are treated, at least in part, by increased hemoglobin A oxygen affinity.

As used herein, "hemoglobin S" refers to the most common abnormal hemoglobin type found in patients with sickle cell disease. Hemoglobin S differs from hemoglobin A only by a single amino acid substitution (i.e., valine substituted for glutamine in the $6^{th}$ position of the globin beta chain). Without being bound by theory, it is believed that treatment of sickle cell disease by the methods and compounds described herein is due, at least in part, by increased hemoglobin S oxygen affinity.

Compounds:

Provided is:

A compound of formula:

Compound 6

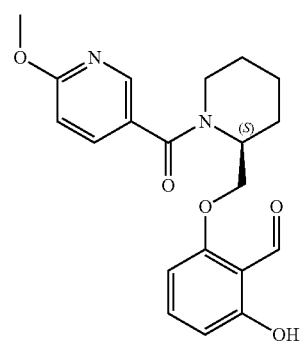

or a stereoisomer thereof, or a pharmaceutically acceptable salt of each thereof, or a pharmaceutically acceptable solvate of each of the foregoing.

A compound of the following formula:

Compound 8

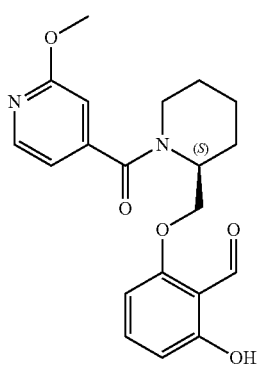

or a stereoisomer thereof, or a pharmaceutically acceptable salt of each thereof, or a pharmaceutically acceptable solvate of each of the foregoing.

A compound of the following formula:

Compound 9

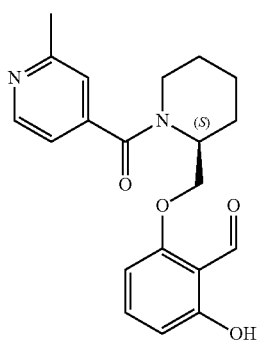

or a stereoisomer thereof, or a pharmaceutically acceptable salt of each thereof, or a pharmaceutically acceptable solvate of each of the foregoing.

Compounds of formula 6 and 8-9 can be made following modifications of procedures well known to a skilled artisan such as by modifying procedures described in WO 2014/150268.

Also provided is a compound of the following formula:

Compound 10

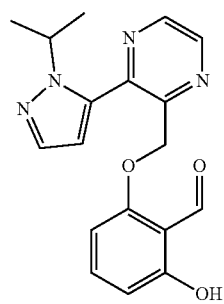

or a pharmaceutically acceptable salt thereof, or a pharmaceutically acceptable solvate of each of the foregoing.

Compound of formula 10 can be made following modifications of procedures well known to a skilled artisan such as by modifying procedures described in US 2013/0190315.

Also provided is a compound of the following formula:

Compound 5

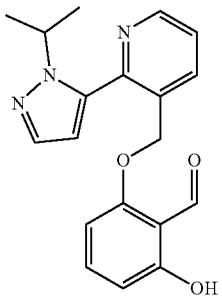

or a pharmaceutically acceptable salt or polymorph thereof.

In some embodiments, the polymorph of Compound 5 comprises a crystalline ansolvate of the free base of Compound 5. In some embodiments, the crystalline ansolvate of the free base of Compound 5 comprises a crystalline anhydrous form.

Figure 5:
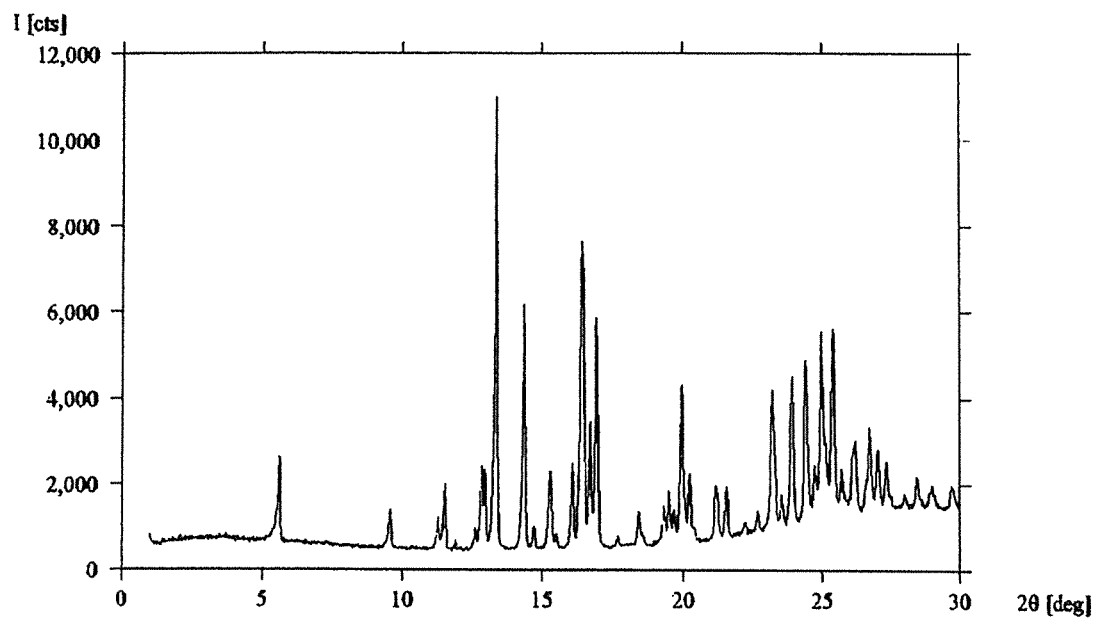
FIG. 5 shows is a XRPD profile and contemplated indexing for free base Form II.

In some embodiments, the crystalline ansolvate of the free base of Compound 5 comprises Form II, which is characterized by an endothermic peak at (97±2) ° C. as measured by differential scanning calorimetry. In another embodiment, the crystalline Form II of the free base of crystalline Compound 5 is characterized by the substantial absence of thermal events at temperatures below the endothermic peak at (97±2) ° C. as measured by differential scanning calorimetry. In another embodiment, the crystalline Form II of the free base of crystalline Compound 5 is characterized by an X-ray powder diffraction peak (Cu Kα radiation at one or more of 13.37°, 14.37°, 19.95° or 23.92° 2θ. In another embodiment, the crystalline Form II of the free base of crystalline Compound 5 is characterized by an X-ray powder diffraction pattern (Cu Kα radiation) substantially similar to that of FIG. 5.

In another embodiment, the crystalline Form II of the free base of crystalline Compound 5 is characterized by at least one X-ray powder diffraction peak (Cu Kα radiation) selected from 13.37°, 14.37°, 19.95° and 23.92° 2θ (each ±0.2° 2θ). In another embodiment, the crystalline Form II of the free base of crystalline Compound 5 is characterized by at least two X-ray powder diffraction peaks (Cu Kα radiation) selected from 13.37°, 14.37°, 19.95° and 23.92° 2θ (each ±0.2° 2θ). In another embodiment, the crystalline Form II of the free base of crystalline Compound 5 is characterized by at least three X-ray powder diffraction peaks (Cu Kα radiation) selected from 13.37°, 14.37°, 19.95° and 23.92° 2θ (each ±0.2° 2θ).

In another embodiment, Form II is characterized by 1, 2, 3, 4, or more peaks as tabulated below in Table A.

TABLE A

| Observed peaks for Form II, XRPD file 613881. | | |
|---|---|---|
| °2θ | d space (Å) | Intensity (%) |
| 5.62 ± 0.20 | 15.735 ± 0.581 | 24 |
| 12.85 ± 0.20 | 6.888 ± 0.108 | 22 |
| 12.97 ± 0.20 | 6.826 ± 0.106 | 21 |
| 13.37 ± 0.20 | 6.622 ± 0.100 | 100 |
| 14.37 ± 0.20 | 6.162 ± 0.087 | 56 |
| 15.31 ± 0.20 | 5.788 ± 0.076 | 21 |
| 16.09 ± 0.20 | 5.507 ± 0.069 | 23 |

TABLE A-continued

Observed peaks for Form II, XRPD file 613881.

| °2θ | d space (Å) | Intensity (%) |
|---|---|---|
| 16.45 ± 0.20 | 5.390 ± 0.066 | 69 |
| 16.75 ± 0.20 | 5.294 ± 0.064 | 32 |
| 16.96 ± 0.20 | 5.227 ± 0.062 | 53 |
| 19.95 ± 0.20 | 4.450 ± 0.045 | 39 |
| 20.22 ± 0.20 | 4.391 ± 0.043 | 20 |
| 23.18 ± 0.20 | 3.837 ± 0.033 | 38 |
| 23.92 ± 0.20 | 3.721 ± 0.031 | 41 |
| 24.40 ± 0.20 | 3.648 ± 0.030 | 44 |
| 24.73 ± 0.20 | 3.600 ± 0.029 | 22 |
| 24.99 ± 0.20 | 3.564 ± 0.028 | 50 |
| 25.12 ± 0.20 | 3.545 ± 0.028 | 28 |
| 25.39 ± 0.20 | 3.509 ± 0.027 | 51 |
| 25.70 ± 0.20 | 3.466 ± 0.027 | 21 |
| 26.19 ± 0.20 | 3.403 ± 0.026 | 27 |
| 26.72 ± 0.20 | 3.336 ± 0.025 | 30 |
| 27.02 ± 0.20 | 3.300 ± 0.024 | 25 |
| 27.34 ± 0.20 | 3.262 ± 0.024 | 23 |
| 28.44 ± 0.20 | 3.138 ± 0.022 | 20 |

In some embodiments, Compound 6 and 8-10 are useful in the methods provided herein. Other compounds useful in the methods provided herein are 3-chloro-2-hydroxy-6-((2-(1-isopropyl-1H-pyrazol-5-yl)pyridin-3-yl)methoxy)benzaldehyde, 2-hydroxy-6-((2-(1-isopropyl-1H-pyrazol-5-yl)pyridin-3-yl)methoxy)benzaldehyde (Compound 5), and others included in the FIGURES and TABLES appended hereto, or a pharmaceutically acceptable salt thereof. Additional compounds that may be used in the methods disclosed herein. Methods of making the additional compounds as well as compounds provided herein, are described in U.S. Patent Publication Nos. 2014/0275152, 2014/0271591, 2014/0274961, 2015/0057251, 2014/0275176, and 2014/0275181; PCT Publication Nos. WO2015/031285 and WO2015/031284; and U.S. Pat. No. 8,952,171 (columns 1-14) each of which is incorporated herein by reference in its entirety. Polymorphic forms of 2-hydroxy-6-((2-(1-isopropyl-1H-pyrazol-5-yl)pyridin-3-yl)methoxy)-benzaldehyde (Compound 5), including methods of making such polymorphic forms are disclosed in U.S. Patent Publication No. 2015/0225366 (see, e.g., Examples 15, 20 and 21) and PCT Publication No. WO2015/120133 (see, e.g., Examples 15, 20 and 21), each of which is incorporated herein by reference in its entirety. In particular, crystalline Form II of the free base of Compound 5 characterized by at least one X-ray powder diffraction peak (Cu Kα radiation) selected from 13.37°, 14.37°, 19.95° and 23.92° 2θ (each ±0.2° 2θ), preferably characterized by at least two X-ray powder diffraction peaks (Cu Kα radiation) selected from 13.37°, 14.37°, 19.95° and 23.92° 2θ (each ±0.2° 2θ), more preferably characterized by at least three X-ray powder diffraction peaks (Cu Kα radiation) selected from 13.37°, 14.37°, 19.95° and 23.92° 2θ (each ±0.2° 2θ).

In another aspect, provided herein is a method for treatment of hypoxia in a patient suffering from a lung disease, the method comprising administering to a subject in need thereof a therapeutically effective amount of a compound provided herein, or a pharmaceutically acceptable composition thereof. In one embodiment the compound is compound 6, 8, 9, or 10. In one embodiment the compound is 2-hydroxy-6-((2-(1-isopropyl-1H-pyrazol-5-yl)pyridin-3-yl)methoxy)benzaldehyde (Compound 5). In one embodiment the compound is crystalline Form II characterized by at least two X-ray powder diffraction peak (Cu Kα radiation) selected from 13.37°, 14.37°, 19.95° and 23.92° 2θ (each ±0.2° 2θ). In one embodiment the lung disease is idiopathic pulmonary fibrosis.

In another aspect, a compound provided herein, or a pharmaceutically acceptable composition thereof, is for use in the treatment of hypoxia in a patient suffering from a lung disease. In one embodiment the compound is compound 6, 8, 9, or 10. In one embodiment the compound is 2-hydroxy-6-((2-(1-isopropyl-1H-pyrazol-5-yl)pyridin-3-yl)methoxy) benzaldehyde (Compound 5). In one embodiment the compound is crystalline Form II characterized by at least two X-ray powder diffraction peak (Cu Kα radiation) selected from 13.37°, 14.37°, 19.95° and 23.92° 2θ (each ±0.2° 2θ). In one embodiment the lung disease is idiopathic pulmonary fibrosis.

In another aspect, provided herein is a method for treatment of idiopathic pulmonary disease in a patient suffering from idiopathic pulmonary disease, the method comprising administering to a subject in need thereof a therapeutically effective amount of a compound provided herein, or a pharmaceutically acceptable composition thereof. In one embodiment the compound is compound 6, 8, 9, or 10. In one embodiment the compound is 2-hydroxy-6-((2-(1-isopropyl-1H-pyrazol-5-yl)pyridin-3-yl)methoxy)benzaldehyde (Compound 5). In one embodiment the compound is crystalline Form II characterized by at least two X-ray powder diffraction peak (Cu Kα radiation) selected from 13.37°, 14.37°, 19.95° and 23.92° 2θ (each ±0.2° 2θ).

In another aspect, a compound provided herein, or a pharmaceutically acceptable composition thereof, is for use in the treatment of idiopathic pulmonary disease in a patient suffering from idiopathic pulmonary disease. In one embodiment the compound is compound 6, 8, 9, or 10. In one embodiment the compound is 2-hydroxy-6-((2-(1-isopropyl-1H-pyrazol-5-yl)pyridin-3-yl)methoxy)benzaldehyde (Compound 5).

In another aspect, provided herein is a method for treatment of fibrosis in a patient suffering from idiopathic pulmonary disease, the method comprising administering to a subject in need thereof a therapeutically effective amount of a compound provided herein, or a pharmaceutically acceptable composition thereof. In one embodiment the compound is compound 6, 8, 9, or 10. In one embodiment the compound is 2-hydroxy-6-((2-(1-isopropyl-1H-pyrazol-5-yl)pyridin-3-yl)methoxy)benzaldehyde (Compound 5). In one embodiment the compound is crystalline Form II characterized by at least two X-ray powder diffraction peak (Cu Kα radiation) selected from 13.37°, 14.37°, 19.95° and 23.92° 2θ (each ±0.2° 2θ).

In another aspect, a compound provided herein, or a pharmaceutically acceptable composition thereof, is for use in the treatment of fibrosis in a patient suffering from idiopathic pulmonary disease. In one embodiment the compound is compound 6, 8, 9, or 10. In one embodiment the compound is 2-hydroxy-6-((2-(1-isopropyl-1H-pyrazol-5-yl)pyridin-3-yl)methoxy)benzaldehyde (Compound 5). In one embodiment the compound is crystalline Form II characterized by at least two X-ray powder diffraction peak (Cu Kα radiation) selected from 13.37°, 14.37°, 19.95° and 23.92° 2θ (each ±0.2° 2θ).

In another aspect, provided herein is a method for increasing oxygen affinity of hemoglobin S in a patient, the method comprising administering to a subject in need thereof a therapeutically effective amount of a compound provided herein, or a pharmaceutically acceptable composition thereof. In one embodiment the compound is compound 6, 8, 9, or 10. In one embodiment the compound is 2-hydroxy- 6-((2-(1-isopropyl-1H-pyrazol-5-yl)pyridin-3-yl)methoxy) benzaldehyde (Compound 5). In one embodiment the compound is crystalline Form II characterized by at least two X-ray powder diffraction peak (Cu Kα radiation) selected from 13.37°, 14.37°, 19.95° and 23.92° 2θ (each ±0.2° 2θ).

In another aspect, a compound provided herein, or a pharmaceutically acceptable composition thereof, is for use in increasing oxygen affinity of hemoglobin S in a patient. In one embodiment the compound is compound 6, 8, 9, or 10. In one embodiment the compound is 2-hydroxy-6-((2-(1-isopropyl-1H-pyrazol-5-yl)pyridin-3-yl)methoxy)benzaldehyde (Compound 5). In one embodiment the compound is crystalline Form II characterized by at least two X-ray powder diffraction peak (Cu Kα radiation) selected from 13.37°, 14.37°, 19.95° and 23.92° 2θ (each ±0.2° 2θ).

In another aspect, provided herein is a method for treating oxygen deficiency associated with sickle cell anemia or acute respiratory distress syndrome (ARDS) in a patient, the method comprising administering to the patient in need thereof a therapeutically effective amount of a compound herein, or a pharmaceutically acceptable composition thereof. In one embodiment the compound is compound 6, 8, 9, or 10. In one embodiment the compound is 2-hydroxy-6-((2-(1-isopropyl-1H-pyrazol-5-yl)pyridin-3-yl)methoxy) benzaldehyde (Compound 5). In one embodiment the compound is crystalline Form II characterized by at least two X-ray powder diffraction peak (Cu Kα radiation) selected from 13.37°, 14.37°, 19.95° and 23.92° 2θ (each ±0.2° 2θ).

In another aspect, a compound provided herein, or a pharmaceutically acceptable composition thereof, is for use in treating oxygen deficiency associated with sickle cell anemia or acute respiratory distress syndrome (ARDS) in a patient. In one embodiment the compound is compound 6, 8, 9, or 10. In one embodiment the compound is 2-hydroxy-6-((2-(1-isopropyl-1H-pyrazol-5-yl)pyridin-3-yl)methoxy) benzaldehyde (Compound 5). In one embodiment the compound is crystalline Form II characterized by at least two X-ray powder diffraction peak (Cu Kα radiation) selected from 13.37°, 14.37°, 19.95° and 23.92° 2θ (each ±0.2° 2θ).

In one embodiment, at least one agent commonly used for treating ARDS is also administered to the patient. In one embodiment, the at least one agent is a neuromuscular blocking agent. In some embodiments, the neuromuscular blocking agent is pancuronium, vecuronium, rocuronium, succinylcholine, or cisatracurium.

In one aspect, a compound as described herein includes a prodrug moiety. Preferably the prodrug moiety imparts at least a 2 fold, more preferably a 4 fold, enhanced solubility and/or bioavailability to the active moiety, and more preferably is hydrolyzed in vivo. Exemplary prodrug moieties are described in U.S. Patent Publication Nos. 2014/0274961 and 2015/0057251, each of which is incorporated herein by reference in its entirety.

Pharmaceutical Compositions:

In further aspects, a pharmaceutical composition is provided comprising any of the compounds described herein (preferably compounds 5, 6, 8-10), and at least a pharmaceutically acceptable excipient. In general, the compounds of this disclosure will be administered in a therapeutically effective amount by any of the accepted modes of administration for agents that serve similar utilities. Therapeutically effective amounts of compounds of this disclosure may range from about 100 mg/day, 200 mg/day, 300 mg/day, 400 mg/day, 500 mg/day, 550 mg/day, 600 mg/day, 650 mg/day, 700 mg/day, 750 mg/day, 800 mg/day, 850 mg/day, 900 mg/day, 950 mg/day or 1 g/day. Preferably, from about 400 mg/day, 500 mg/day, 550 mg/day, 600 mg/day, 650 mg/day, 700 mg/day, 750 mg/day, 800 mg/day, or 850 mg/day. Therapeutically effective amounts of compounds of this disclosure may also range from about 500 to 1000 mg/day, or 600 to 900 mg/day. The actual amount of the compound of this disclosure, i.e., the active ingredient, will depend upon numerous factors such as the severity of the disease to be treated, the age and relative health of the patient, the potency of the compound being utilized, the route and form of administration, and other factors. Such compositions can be formulated for different routes of administration. Routes that may be used include intravenous, intra-arterial, intramuscular, intraperitoneal, intracutaneous, percutaneous, transdermal, oral, pulmonary, rectal, nasal, vaginal, lingual, intracranial, and subcutaneous routes. Suitable dosage forms for administering any of the compounds described herein include tablets, capsules, pills, powders, aerosols, suppositories, parenterals, and liquids, including suspensions, solutions and emulsions. In preferred embodiments, the compositions are suitable for injection, for example, and without limitation, for intravenous, intra-arterial, intramuscular, intraperitoneal, intracutaneous, intracranial, and subcutaneous routes. Sustained release dosage forms may also be used, for example, in a transdermal patch form. All dosage forms may be prepared using methods that are standard in the art (see e.g., Remington's Pharmaceutical Sciences, $16^{th}$ ed., A. Oslo editor, Easton Pa. 1980).

Pharmaceutically acceptable excipients are non-toxic, aid administration, and do not adversely affect the therapeutic benefit of the compounds disclosed herein. Such excipients may be any solid, liquid, semi-solid or, in the case of an aerosol composition, gaseous excipient that is generally available to one of skill in the art. Pharmaceutical compositions in accordance with the aspects and embodiments provided herein are prepared by conventional means using methods known in the art.

The compositions disclosed herein may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions, suspensions, emulsions and the like can be prepared using water or physiologically compatible organic solvents such as ethanol, 1,2-propylene glycol, polyglycols, dimethylsulfoxide, fatty alcohols, triglycerides, partial esters of glycerin and the like.

Solid pharmaceutical excipients include starch, cellulose, hydroxypropyl cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc.

In one embodiment, provided herein are sustained release formulations such as drug depots or patches comprising an effective amount of a compound provided herein. In another embodiment, the patch further comprises gum Arabic or hydroxypropyl cellulose separately or in combination, in the presence of alpha-tocopherol. Preferably, the hydroxypropyl cellulose has an average MW of from 10,000 to 100,000. In a more preferred embodiment, the hydroxypropyl cellulose has an average MW of from 5,000 to 50,000.

Compounds and pharmaceutical compositions disclosed herein maybe used alone or in combination with other compounds. When administered with another agent, the co-administration can be in any manner in which the pharmacological effects of both are manifest in the patient at the same time. Thus, co-administration does not require that a single pharmaceutical composition, the same dosage form, or even the same route of administration be used for administration of both the compounds disclosed herein and the other agent or that the two agents be administered at precisely the same time. However, co-administration can be accomplished conveniently by the same dosage form and the same route of administration, at substantially the same time. Such administration most advantageously proceeds by delivering the active ingredients separately or simultaneously in one or more pharmaceutical compositions in accordance with the present disclosure.

In one aspect, a compounds or pharmaceutical composition disclosed herein is co-administered with an agent that increases RBC count. In one embodiment, the agent is a blood transfusion. In a preferred embodiment, the agent is an erythropoiesis-stimulating agent.

Utility

In one aspect, a compound described herein is used to treat a condition associated with hypoxia. In another aspect, a compound described herein is used to treat one or more symptoms associated with the condition (hypoxia). In a further aspect, a compound described herein is used in healthy subjects where there is a need for short to long term oxygenation. In yet a further aspect, a compound described herein is used in treating disease manifesting as hypoxemia and requiring oxygenation support. In yet a further aspect, a compound described herein is used in treating diseases not manifesting as hypoxemia but where increased $O_2$ delivery to the tissue may be beneficial.

In one embodiment, provided herein is a method for treating acute respiratory distress syndrome (ARDS) in a patient, the method comprising administering to the patient a therapeutically effective amount of a compound described herein. "Acute respiratory distress syndrome" refers to a life-threatening lung condition that prevents enough oxygen from getting to the lungs and into the blood. ARDS is also referred to as noncardiogenic pulmonary edema, increased-permeability pulmonary edema, stiff lung, shock lung, or acute lung injury. ARDS can be caused by any major injury to the lung. Some common causes include, without limitation: breathing vomit into the lungs (aspiration), inhaling chemicals, lung transplant, pneumonia, septic shock (infection throughout the body), and trauma. In one embodiment, provided herein is a method for treating hypoxia associated with lung cancer in a patient, the method comprising administering to the patient a therapeutically effective amount of a compound as described herein.

In another embodiment, provided herein is a method for treating hypoxia associated with decreased RBC count in a patient being treated for cancer, the method comprising administering to the patient a therapeutically effective amount of a compound as described herein. In one embodiment, the patient is treated for cancer using chemotherapy. In one embodiment, the patient is treated for cancer using radiation therapy. In one embodiment, the method further comprises treating the patient with an agent to increase RBC count. Agents for increasing RBC count are known in the art, including blood transfusion or erythropoiesis stimulating agents. In one embodiment, the erythropoiesis-stimulating agent is erythropoietin, epoetin alfa, epoetin beta, darbepoetin alfa, or methoxy polyethylene glycol-epoetin beta. In a preferred embodiment, the erythropoiesis-stimulating agent is epoetin alfa or darbepoetin alfa.

In yet another embodiment, provided herein is a method for treating hypoxia associated with COPD in a patient, the method comprising administering to the patient a therapeutically effective amount of a compound as described herein. "COPD" refers to a progressive lung disease that compromises lung function and decreases the amount of oxygen that gets into the lungs and into the blood. COPD includes emphysema and chronic bronchitis. The most common causes of COPD include tobacco smoking and pollution.

In one embodiment, at least one agent commonly used for treating COPD is co-administered to the patient. In one embodiment, the at least one agent is systemically administered corticosteroid, locally administered corticosteroid, xolair, beta adrenergic broncodilator, anti-histamine, or anti-mast cell degranulation agent.

In yet another embodiment, provided herein is a method for treating hypoxia associated with pulmonary edema in a patient, the method comprising administering to the patient a therapeutically effective amount of a compound as described herein.

In yet another embodiment, provided herein is a method for treating hypoxia associated with cystic fibrosis of the lungs in a patient, the method comprising administering to the patient a therapeutically effective amount of a compound as described herein.

In yet another embodiment, provided herein is a method for treating hypoxia associated with asthma in a patient, the method comprising administering to the patient a therapeutically effective amount of a compound as described herein.

In one embodiment, at least one agent commonly used for treating asthma is co-administered to the patient. In one embodiment, the at least one agent is systemically administered corticosteroid, locally administered corticosteroid, xolair, beta adrenergic broncodilator, anti-histamine, or anti-mast cell degranulation agent.

In yet another embodiment, provided herein is a method for treating hypoxia associated with pneumonia in a patient, the method comprising administering to the patient a therapeutically effective amount of a compound as described herein.

In yet another embodiment, provided herein is a method for treating hypoxia associated with rheumatoid lung disease in a patient, the method comprising administering to the patient a therapeutically effective amount of a compound as described herein.

In yet another embodiment, provided herein is a method for treating hypoxia associated with acute lung injury in a patient, the method comprising administering to the patient a therapeutically effective amount of a compound as described herein.

In yet another embodiment, provided herein is a method for treating hypoxia associated with idiopathic pulmonary fibrosis (IPF) in a patient, the method comprising administering to the patient a therapeutically effective amount of a compound as described herein. In addition to hypoxemia, the disease pathology of IPF involves inflammation and lung injury caused by reactive oxygen species (ROS) produced by leukocytes, and fibrosis. In one embodiment, an anti-inflammatory compound is co-administered. In one embodiment, an anti-fibrosis agent is co-administered to the patient. In one embodiment, the anti-fibrosis agent is selected from the group consisting of pirfenidone, nintenabib, lecithinized superoxide dismutase, and systemic corticosteroids.

In yet another embodiment, provided herein is a method for treating hypoxia associated with sleep apnea in a patient, the method comprising administering to the patient a therapeutically effective amount of a compound as described herein.

In yet another embodiment, provided herein is a method for treating hypoxia associated with altitude sickness in a patient, the method comprising administering to the patient a therapeutically effective amount of a compound as described herein.

In yet another embodiment, provided herein is a method for treating hypoxia associated with deep or shallow water blackout in a patient, the method comprising administering to the patient a therapeutically effective amount of a compound as described herein.

In yet another embodiment, provided herein is a method for treating a symptom or condition associated with hypoxia. In one embodiment, provided herein a method of increasing arterial blood saturation in a patient with hypoxia, comprising administering to the patient a therapeutically effective amount of a compound as described herein. In another embodiment, provided herein is a method of improving oxygen delivery to a tissue of a patient with hypoxia, comprising administering to the patient a therapeutically effective amount of a compound as described herein. In another embodiment, provided herein is a method of reducing lactate build-up in a tissue of a patient with hypoxia, comprising administering to the patient a therapeutically effective amount of a compound as described herein. In another embodiment, provided herein is a method of reducing acidosis of arterial blood of a patient with hypoxia, comprising administering to the patient a therapeutically effective amount of a compound as described herein. In one embodiment, the hypoxia is acute. In one embodiment, the hypoxia is chronic.

In certain aspects, the compounds, compositions and methods provided herein are contemplated to be used to treat a variety of vascular inflammatory conditions. The methods comprise administering an inflammation inhibiting effective amount of a compound or a composition provided or utilized herein. In some embodiments, the inflammatory condition is associated with coronary artery disease, cerebral ischemia and peripheral artery disease. In some embodiments, the inflammatory condition treated is associated with an autoimmune disease, such as, without limitation, lupus erythematosus, multiple sclerosis, rheumatoid arthritis, ocular inflammation and Crohn's disease. In other embodiments, the condition is an acute or chronic inflammatory condition, such as that associated with allergy, asthma, irritable bowel syndrome, ulcerative colitis, and psoriasis. In other embodiments, the condition is systemic inflammation of the body, such as sepsis, gram positive or gram negative shock. In other embodiments, the condition is a malignancy, such as acute leukemia/lymphoma, which displays inflammatory or allergic manifestations. In other embodiments, the condition is inflammatory condition associated with IPF.

In yet another aspect, the compositions provided herein are used in the treatment of pulmonary fibrosis in a patient, the method comprising administering to the patient a therapeutically effective amount of a compound as described herein. In some embodiments, the pulmonary fibrosis is caused by the use of certain medicines, including, for example, certain chemotherapeutic drugs (e.g., methotrexate and cyclophosphamide), heart medications (e.g., amiodarone and propranolol), and antibiotics (e.g., nitrofurantoin and sulfasalazine). In some embodiments, the pulmonary fibrosis is caused by inhalation exposure to environmental and occupational pollutants, including, for example, asbestos, silica, and hard metal dusts. In some embodiments, the pulmonary fibrosis is caused by connective tissue diseases, including, for example, systemic lupus erythematosus, rheumatoid arthritis, and scleroderma. In some embodiments, the pulmonary fibrosis is caused by inflammatory diseases, including, for example, sarcoidosis. In some embodiments, the pulmonary fibrosis is caused by bacterial or viral infections, including, for example, tuberculosis, and pneumonia. In one embodiment the compound is Compound 5.

In yet another aspect, the compositions provided herein are used in the treatment of pulmonary fibrosis, in particular, fibrosis associated with IPF in a patient, the method comprising administering to the patient a therapeutically effective amount of a compound as described herein. In one embodiment the compound is Compound 5.

In yet another aspect, provided herein is a method for treating idiopathic pulmonary fibrosis (IPF) in a patient, the method comprising administering to the patient a therapeutically effective amount of a compound as described herein. In one embodiment the compound is Compound 5.

In some aspects, the compounds and compositions provided herein can be administered prophylactically, e.g., and without limitation, for preventing emphysema.

In some aspects, the compounds and compositions provided herein can be administered prophylactically, e.g., and without limitation, for preventing high altitude hypoxia, or deep or shallow water blackout.

In some aspects, provided herein are methods for lowering C-reactive protein (CRP) in a patient in need thereof, such as due to having a high CRP level indicative of inflammation. The methods comprise administering an effective amount of a compound or composition provided or utilized herein.

EXAMPLES

Abbreviations

Hb Hemoglobin
OEC Oxygen equilibrium curve
$PO_2$ Partial pressure of oxygen
Hb $O_2$ Hemoglobin liganded to oxygen
LPS Lipopolysaccharide
$FiO_2$ Fraction of inspired $O_2$
PK Pharmacokinetics
PD Pharmacodynamics
BALF Bronchoalveolar lavage fluid
ALI Acute lung injury
ARDS Acute respiratory distress syndrome

SYNTHETIC EXAMPLES

Preparation of 2,6-dihydroxybenzaldehyde

INT-1

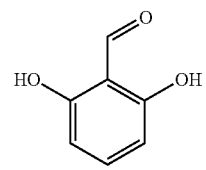

Into a 3000-mL three neck round-bottom flask, was placed a solution of $AlCl_3$ (240 g, 1.80 mol, 3.00 equiv) in dichloromethane (1200 mL). A solution of 2,6-dimethoxybenzaldehyde (100 g, 601.78 mmol, 1.00 equiv) in dichloromethane (800 ml) was added to the reaction mixture dropwise at 0° C. The resulting solution was stirred overnight at room temperature, and then it was quenched with 200 mL of diluted HCl (2M). The resulting solution was extracted with 2×200 mL of dichloromethane. The combined organic layers were concentrated under vacuum. The residue was applied onto a silica gel column with ethyl acetate/petroleum ether (1:200-1:50) as eluent to furnish 40 g (48%) of 2,6-dihydroxybenzaldehyde as a yellow solid. $^1$HNMR (300 MHz, DMSO-d$_6$) δ 11.25 (s, 2H), 10.25 (s, 1H), 7.36 (m, 1H), 6.36 (d, J=8.4 Hz 2H); MS (ESI) m/z 139 [M+H]$^+$.

Example 1 (Compound 6)

Synthesis of (S)-2-hydroxy-6-((1-(6-methoxynicotinoyl)piperidin-2-yl)methoxy)benzaldehyde

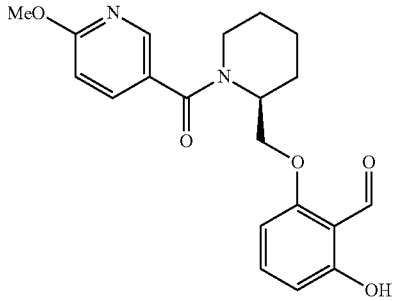 [SMILES: COc1ccc(C(=O)N2CCCC[C@H]2COc2cccc(O)c2C=O)cn1]

Step 1:
Into a 50-mL round-bottom flask, was placed a solution of 6-methoxypyridine-3-carboxylic acid (613 mg, 4.0 mmol, 1.00 equiv), dichloromethane (20 mL), (2S)-piperidin-2-ylmethanol (461 mg, 4.0 mmol, 1.00 equiv), DIEA (1.03 g, 8.0 mmol, 2.00 equiv) and HATU (1.67 g, 4.39 mmol, 1.10 equiv). The resulted solution was stirred for 2 h at room temperature. After concentration, the residue was extracted with 100 mL of EA and washed with 3×30 mL of brine. The organic phase was dried over anhydrous sodium sulfate and concentrated under vacuum. The residue was purified by silica gel column eluted with ethyl acetate/petroleum ether (1:2). This resulted in 550 mg (55%) of [(2S)-1-[(6-methoxypyridin-3-yl)carbonyl]piperidin-2-yl]methanol as a white solid.
Step 2:
Into a 25-mL round-bottom flask purged and maintained with an inert atmosphere of nitrogen, was placed a solution of [(2S)-1-[(6-methoxypyridin-3-yl)carbonyl]piperidin-2-yl]methanol (420 mg, 1.68 mmol, 1.00 equiv), tetrahydrofuran (10 mL) and 2,6-dihydroxy-benzaldehyde (278 mg, 2.02 mmol, 1.20 equiv) with stirring at 0° C., to which was added sequentially PPh$_3$ (529 mg, 2.02 mmol, 1.20 equiv) and DTAD (465 mg, 2.02 mmol, 1.20 equiv). The resulted solution was stirred for 16 h at room temperature. After concentration, the residue was purified by silica gel column eluted with ethyl acetate/petroleum ether (1:1) to a crude product (130 mg) which was further purified by prep-TLC eluted with DCM/EA (2:1). This resulted in 86.1 mg (14%) of 2-hydroxy-6-[[(2S)-1-[(6-methoxypyridin-3-yl)carbonyl]piperidin-2-yl]methoxy]benzaldehyde as a yellow solid.

LC-MS (ESI) m/z: calculated for C$_{20}$H$_{22}$N$_2$O$_5$: 370.15; found: 371[M+H]$^+$. Rt: 1.88 min. $^1$H NMR (300 MHz, CDCl$_3$): δ 11.98 (s, 1H), 10.29 (s, 1H), 8.30 (s, 1H), 7.75 (d, J=8.7 Hz, 1H), 7.42 (t, J=8.4 Hz, 1H), 6.86 (d, J=8.7 Hz, 1H), 6.57 (d, J=8.1 Hz, 1H), 6.42 (d, J=7.2 Hz, 1H), 5.05 (brs, 1H), 4.39-4.33 (m, 1H), 4.23-4.21 (m, 1H), 4.09-4.06 (m, 4H), 3.17-3.14 (m, 1H), 2.00-1.57 (m, 6H).

Example 2 (Compound 8)

Synthesis of (S)-2-hydroxy-6-((1-(2-methoxyisonicotinoyl)piperidin-2-yl)methoxy)benzaldehyde

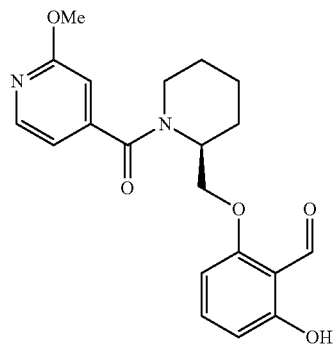 [SMILES: COc1cc(C(=O)N2CCCC[C@H]2COc2cccc(O)c2C=O)ccn1]

Step 1:
Into a 50-mL round-bottom flask, was placed a solution of 2-methoxyisonicotinic acid (1.00 g, 6.5 mmol, 1.00 equiv), dichloromethane (15 mL), (2S)-piperidin-2-ylmethanol (827 mg, 7.2 mmol, 1.1 equiv), DIEA (1.7 g, 13.0 mmol, 2.00 equiv) and HATU (3.70 g, 9.75 mmol, 1.50 equiv). The resulted solution was stirred for 2 h at room temperature. After concentration, the residue was dissolved with 100 mL of EA, washed with 3×30 mL of brine, dried over anhydrous sodium sulfate and concentrated under vacuum. The residue was purified by silica gel column eluted with dichloromethane/methanol (15:1). This resulted in 800 mg (50%) of (S)-(2-(hydroxymethyl)piperidin-1-yl)(2-methoxypyridin-4-yl)methanone as a light yellow solid.
Step 2:
Into a 25-mL round-bottom flask purged and maintained with an inert atmosphere of nitrogen, was placed a solution of (S)-(2-(hydroxymethyl)piperidin-1-yl)(2-methoxypyridin-4-yl)methanone (300 mg, 1.2 mmol, 1.00 equiv) and 2,6-dihydroxybenzaldehyde (497 mg, 3.6 mmol, 3.0 equiv) in toluene (10 mL) with stirring at 0° C. To the above solution was added PPh$_3$ (943.2 mg, 3.6 mmol, 3.0 equiv), followed by DTAD (828 mg, 3.6 mmol, 3.0 equiv). The resulted solution was stirred for 16 h at room temperature. After concentration, the residue was purified by Prep-HPLC with the following conditions.
Column: Waters XBridge C18 19*150 mm, 5 μm; mobile phase: H$_2$O (it is a buffer of 10 mM NH$_4$HCO$_3$+0.05% ammonia) and CH$_3$CN with a gradient of 15% to 45% acetonitrile in 5 min then 45% to 75% acetonitrile in 5 min; flow rate: 15 mL/min; detector UV wavelength: 254 nm. This resulted in 129 mg (29%) of (S)-2-hydroxy-6-((1-(2-methoxyisonicotinoyl)piperidin-2-yl)methoxy)benzaldehyde as a light yellow solid. LC-MS (ESI) m/z: calculated for C$_{20}$H$_{22}$N$_2$O$_5$: 370.15; found: 371[M+H]$^+$. Rt: 1.82 min. $^1$H NMR (300 MHz, CDCl$_3$): δ 12.00 (s, 1H), 10.34 (br. s, 1H), 8.25 (d, J=5.1 Hz 1H), 7.42 (br. s, 1H), 6.84 (d, J=4.8

Hz, 1H), 6.71 (s, 1H), 6.60 (d, J=8.4 Hz, 1H), 6.46 (br. s, 1H), 5.31 (br. s, 1H), 4.33-4.22 (m, 2H), 3.98 (s, 3H), 3.58 (br. s, 1H), 3.12 (br. s, 1H), 1.94-1.57 (m, 6H).

Example 3 (Compound 9)

Synthesis of (S)-2-hydroxy-6-((1-(2-methylisonicotinoyl)piperidin-2-yl)methoxy)benzaldehyde

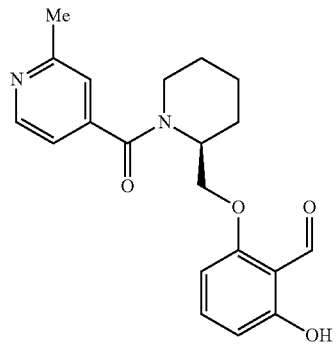 [SMILES: Cc1cc(C(=O)N2CCCC[C@H]2COc2cccc(O)c2C=O)ccn1]

Step 1:

Into a 50-mL round-bottom flask, was placed a solution of 2-methylpyridine-4-carboxylic acid (548 mg, 4.00 mmol, 1.00 equiv), (2S)-piperidin-2-ylmethanol (460 mg, 3.99 mmol, 1.00 equiv), DIEA (1.29 g, 9.98 mmol, 2.50 equiv) and HATU (1.67 g, 4.39 mmol, 1.10 equiv) in dichloromethane (20 mL). The resulted solution was stirred for 30 min at room temperature. After concentration, the residue was dissolved with 200 mL of EA. Then it was washed with 3×20 mL of brine, dried over anhydrous sodium sulfate and concentrated under vacuum to give a residue. The crude was purified by silica gel column eluted with dichloromethane/methanol (10:1). This resulted in 426 mg (46%, 97% ee) of [(2S)-1-[(2-methylpyridin-4-yl)carbonyl]-piperidin-2-yl]methanol as yellow oil.

Step 2:

Into an 100-mL round-bottom flask purged and maintained with an inert atmosphere of nitrogen, was placed a solution of [(2S)-1-[(2-methylpyridin-4-yl)carbonyl]piperidin-2-yl]methanol (426 mg, 1.82 mmol, 1.00 equiv) and 2,6-dihydroxybenzaldehyde (753 mg, 5.45 mmol, 3.00 equiv) in toluene (30 mL) with stirring at 0° C. To the above solution was added $PPh_3$ (1.43 g, 5.45 mmol, 3.00 equiv), followed by DTAD (1.25 g, 5.43 mmol, 3.00 equiv) at 0° C. The resulted solution was stirred for 16 h at room temperature. After concentration, the residue was purified by silica gel column eluted with dichloromethane/ethyl acetate (1:1) to give a crude product, which was further purified by Prep-HPLC with the following conditions. Column: Waters XBridge C18 19*150 mm, 5 μm; mobile phase: $H_2O$ (it is a buffer of 10 mM $NH_4HCO_3$+0.05% ammonia) and $CH_3CN$ with a gradient of 42% to 46% acetonitrile in 8 min; flow rate: 20 mL/min; detector UV wavelength: 254 nm. This resulted in 90.6 mg (14%) of 2-hydroxy-6-[[(2S)-1-[(2-methylpyridin-4-yl)carbonyl]piperidin-2-yl]methoxy]benzaldehyde as a light yellow solid. LC-MS (ESI) m/z: calculated for C20H22N2O4: 354; found: 355[M+H]$^+$. Rt: 1.00 min. $^1$H NMR (300 MHz, CDCl$_3$): δ 11.99 (s, 1H), 10.34 (s, 1H), 8.58 (d, J=5.1 Hz, 1H), 7.43-7.40 (m, 1H), 7.12 (s, 1H), 7.05 (d, J=4.8 Hz, 1H), 6.59 (d, J=8.7 Hz, 1H), 6.48 (br., 1H), 5.34 (br., 1H), 4.38-4.05 (m, 2H), 3.55 (br., 1H), 3.10 (br., 1H), 2.61 (s, 3H), 1.96-1.64 (m, 6H).

Example 4 (Compound 10)

Synthesis of 2-hydroxy-6-((3-(1-isopropyl-1H-pyrazol-5-yl)pyrazin-2-yl)methoxy)benzaldehyde

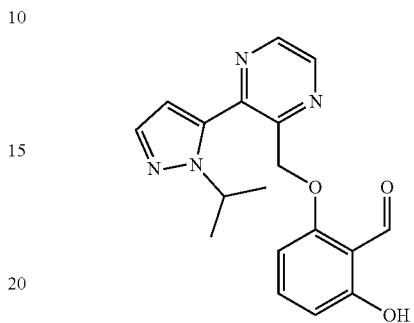

Step 1:

3-Chloropyrazine-2-carboxylic acid (2.97 g, 18.73 mmol, 1 eq.) was dissolved in tetrahydrofuran (75 mL). The solution was stirred in an ice bath and triethylamine (5.2 mL, 37.5 mmol, 2 eq.) was added followed by addition of methyl chloroformate (1.74 mL, 22.5 mmol, 1.2 eq.) dropwise. After 30 m, the reaction was filtered and the solid rinsed with more tetrahydrofuran (10 mL). The tetrahydofuran solution was stirred in an ice bath and a suspension of sodium borohydride (1.4 g, 37.5 mmol, 2 eq.) in water (3 mL) was added. After 1 h, a saturated aqueous ammonium chloride solution (100 mL) was added to the reaction and the mixture was extracted with ethyl acetate (2×100 mL). The combined organic phases were washed with a saturated aqueous sodium chloride solution (25 mL) and dried over sodium sulfate. After filtration and evaporation, the residue was purified by silica gel chromatography (5-70% ethyl acetate/hexanes) to give (3-chloropyrazin-2-yl)methanol (0.84 g, 31%) as a faintly colored oil.

Step 2:

(3-Chloropyrazin-2-yl)methanol (0.6 g, 4.15 mmol, 1 eq.) was dissolved in 1,4-dioxane (16 mL) and water (5 mL). The solution and reaction vessel were purged with a stream of $N_2$ gas. 1-isopropyl-5-(4,4,5,5-tetramethyl-1,3,2-dioxaborolan-2-yl)-1H-pyrazole (1.08 g, 4.57 mmol, 1.1 eq.), [1,1'-bis(diphenylphosphino)ferrocene]dichloropalladium(II) (0.3 g, 0.41 mmol, 0.1 eq.) and potassium carbonate (0.57 g, 4.15 mmol, 1 eq.) were added and the reaction was stirred in a heat block at 100° C. After 1 h, the reaction was judged to be complete by TLC (35% ethyl acetate/hexanes). The reaction mixture was cooled to 25° C., and taken up in a mixture of ethyl acetate (100 mL) and an aqueous saturated sodium bicarbonate solution (100 mL). The phases were separated and the aqueous phase was extracted once more with ethyl acetate (50 mL). The combined organic phases were washed with an aqueous saturated sodium chloride solution (50 mL) and dried over sodium sulfate. After filtration and evaporation, the residue was purified by silica gel chromatography (5-70% ethyl acetate/hexanes) to give (3-(1-isopropyl-1H-pyrazol-5-yl)pyrazin-2-yl)methanol (0.53 g, 59%) as a light yellow oil.

Step 3:

(3-(1-Isopropyl-1H-pyrazol-5-yl)pyrazin-2-yl)methanol (0.308 g, 1.41 mmol, 1 eq.) was dissolved in dichromethane (4 ml) and stirred in an ice bath. Thionyl chloride (2.05 mL, 28.2 mmol, 20 eq.) was added slowly and the reaction mixture was stirred to 20° C. over 2 h. The reaction was then evaporated to a residue, re-dissolved in toluene (20 mL) and evaporated to dryness. This cycle of evaporation, dissolution and evaporation was repeated two further times. The resulting residue of 5-(3-(chloromethyl)pyrazin-2-yl)-1-isopropyl-1H-pyrazol-1-ium chloride was used directly in the next step.

Step 4:

2-Hydroxy-6-(methoxymethoxy)benzaldehyde (0.15 g, 0.823 mmol, 1 eq.) was dissolved in N,N-dimethylformamide (5 mL). 5-(3-(chloromethyl)pyrazin-2-yl)-1-isopropyl-1H-pyrazol-1-ium chloride (0.247 g, 0.905 mmol, 1.1 eq.) and potassium carbonate (0.45 g, 3.3 mmol, 4 eq.) were added and the reaction was stirred in a heat block for 2 h at 60° C. The reaction was cooled, and poured into a mixture of ethyl acetate (100 mL) and water (50 mL). The phases were separated and the aqueous phase was extracted with more ethyl acetate (2×50 mL). The combined organic phases were washed with water (25 mL), an aqueous saturated sodium chloride solution (25 mL), and dried over sodium sulfate. After concentration, the residue was purified by silica gel chromatography (5-80% ethyl acetate/hexanes) to give 2-((3-(1-isopropyl-1H-pyrazol-5-yl)pyrazin-2-yl)methoxy)-6-(methoxymethoxy)benzaldehyde (0.22 g, 70%) as an off-white solid.

Step 5:

2-((3-(1-Isopropyl-1H-pyrazol-5-yl)pyrazin-2-yl)methoxy)-6-(methoxymethoxy)-benzaldehyde (0.22 g, 0.575 mmol, 1 eq.) was dissolved in dry THF (3 mL). Concentrated HCl (0.19 mL, 2.3 mmol, 4 eq.) was then added slowly to the reaction. After 3 h the reaction was complete as determined by TLC (silica gel, 50% ethyl acetate/hexanes), and it was poured into ethyl acetate (50 mL) and an aqueous sodium bicarbonate solution (25 mL). The phases were separated and the aqueous phase was extracted further with ethyl acetate (2×30 mL). The combined organic phases were washed with a saturated aqueous sodium chloride solution (20 mL) and dried over sodium sulfate. After filtration and evaporation, the crude product was purified by silica gel chromatography (5-70% ethyl acetate/hexanes) to give 2-hydroxy-6-((3-(1-isopropyl-1H-pyrazol-5-yl)pyrazin-2-yl)methoxy)benzaldehyde (0.127 g, 65%) as an off-white solid after lyophilization from water/acetonitrile. $^1$H NMR (400 MHz, CDCl$_3$) δ 11.94 (s, 1H), 10.23 (dd, J=0.59, 1.33 Hz, 1H), 8.74 (d, J=2.41 Hz, 1H), 8.66 (d, J=2.41 Hz, 1H), 7.61 (dd, J=0.41, 1.90 Hz, 1H), 7.38 (t, J=8.40 Hz, 1H), 6.56 (dt, J=0.64, 8.50 Hz, 1H), 6.46 (d, J=1.91 Hz, 1H), 6.40 (dd, J=0.69, 8.30 Hz, 1H), 5.26 (s, 2H), 4.68 (hept, J=6.67 Hz, 1H), 1.48 (d, J=6.61 Hz, 6H). $^{13}$C NMR (101 MHz, CDCl$_3$) δ 194.01, 163.71, 160.87, 149.32, 144.06, 143.43, 138.46, 138.25, 110.85, 107.81, 102.18, 69.25, 51.14, 22.83. MS (ESI) m/z 339 [M+H]$^+$.

BIOLOGICAL EXAMPLES

Example 1

Compound Characterization

Representative compounds disclosed herein were tested for their ability to increase hemoglobin oxygen affinity using hemoximetry. Blood (20% or 40% Hct) was incubated with compound at various concentrations followed by hemoximetry. Oxygen equilibrium curves for blood treated with compounds were obtained by deoxygenation of O2-equilibrated samples in a Hemox buffer at 37° C., using a Hemox Analyzer. The blood samples were transferred to the hemoximeter sample chamber where they were first saturated with compressed air and then deoxygenated with pure nitrogen. The absorbance at wavelengths that correspond to the isosbestic point (570 nm) and deoxy Hb (560 nm) was recorded as a function of the sample O2 tension (pO2). During deoxygenation, the pO2 and percent O2 saturation values were collected to obtain the OECs and the p50 values (partial pressure of O2 at which Hb is 50% saturated with O2). p50 values were calculated using a non-linear regression analysis. The compounds described herein dose-dependently increased hemoglobin oxygen affinity as seen in FIGS. 1B, 1E, 1H, 1K, 1N, 1Q, 1T, 1W, 1Z, 1AC, and 1AE.

Bohr Effect: Oxygen delivery to tissues was mediated by decreased hemoglobin-O$_2$ affinity via changes in the pH of blood (Bohr effect) and by an increase in the concentration of 2,3-diphosphoglycerate in red blood cells. For hypoxia caused by pathologic conditions such as ARDS or acute lung injury, respiratory acidosis may lead to a reduction in pH of blood thereby reducing hemoglobin-O$_2$ affinity and reduced oxygen uptake. The compounds described herein increased oxygen affinity under acidic (low pH) conditions as seen in FIGS. 1C, 1F, 1I, 1L, 1O, 1R, 1U, 1X, 1AA, and 1AF.

Reactive oxygen species (ROS) released from activated white blood cells cause lung injury as well as fibrotic changes in patients with IPF. Surprisingly, compound 1 disclosed herein displayed anti-oxidative (FIGS. 1AG and 1AH) and anti-inflammatory activity (FIGS. 1AI, 1AJ, and 1AK) in in vitro experimental systems containing neutrophils and macrophages. A previously-described aldehyde compound, 5-hydroxymethyl-2-furfural (5-HMF), does not display this activity (FIGS. 1AG and 1AH). Thus, the compounds described herein could also provide a method to inhibit the adverse effects of inflammation in a patient. Reduction in systemic pro-inflammatory cytokines (tumor necrosis alpha and interleukin-6) also has the potential to exert a broad anti-inflammatory effect which would supplement the beneficial effect of alleviation of hypoxemia via increased hemoglobin-O$_2$ affinity.

Example 2

Tolerance to Hypoxia Mouse Model

This study was conducted to evaluate the effect of increased Hb O$_2$ affinity on O$_2$ transport in the lungs of healthy mice during hypoxia. In this regard, the effect of Compound 1, that increases Hb O$_2$ affinity, was studied in healthy mice (without lung injury) subjected to extreme hypoxia. In this animal model, by exposing mice to hypoxia, the amount of O$_2$ available for uptake in the lungs is reduced providing a preclinical model of pulmonary hypoxemia associated with lung disease in which the partial pressure of O$_2$ (pO$_2$) is decreased below normal. This animal model also mimics conditions of exposure to environments of reduced O$_2$ tensions (for example O$_2$ tensions at high altitudes).

Study:

Male, C57BL mice were fitted with a dorsal skinfold window chamber for direct visualization of an intact microvascular bed (Yalcin & Cabrales 2012). After the window chamber was implanted, the animals were left to recover for at least 2 days, before undergoing surgery a second time for arterial (carotid) catheter implantation (PESO tubing). After two day of recovery, mice were dosed orally with Compound 1 (70 or 140 mg/kg) or vehicle only and Hb O$_2$ affinity was determined by hemoximetry. Two hours post dose, conscious mice were placed in a restraining tube with a longitudinal slit from which the protruding window chamber provided a microscopic stage for observation. In this setup, gas flow rate (0.2 L/min) into the tube is diffused by a cotton filter barrier. Baseline measurements for normoxia (21% $O_2$) were completed within an hour of restraining mice. The animals were then exposed to stepwise hypoxia by decreasing the $O_2$ concentration to 15, 10 and 5%. Animals were kept at each hypoxic level for 30 min. Mice were allowed 15 min of acclimatization at each new hypoxic level before measurements were taken. During hypoxia, changes in systemic and microvascular hemodynamics, blood gases, blood lactate, tissue partial pressure of $O_2$ ($PO_2$), tissue hypoxia and tolerance to hypoxia were evaluated. At each time point, mice with adequate systolic blood pressure (BP) were counted as survived and mice with severe hypotension (BP≤60 mmHg) were counted as non-survived and were euthanized.

Measurement of Systemic Parameters:

MAP (mean arterial pressure) and heart rate (HR) were recorded continuously from Carotid catheter. Hct was measured from centrifuged arterial blood samples taken in heparinized capillary tubes. Arterial blood was collected in heparinized glass capillaries (50 μL) and immediately analyzed for $PO_2$, $PCO_2$, base excess, and pH. Arterial Hb saturations were measured using a CO-Oximeter.

Blood Oxygen Equilibrium Curve:

Oxygen equilibrium curves for mice blood were obtained by deoxygenation of $O_2$-equilibrated samples in a Hemox buffer at 37° C., using a Hemox Analyzer (TCS Scientific Corporation, New Hope, Pa.). The blood samples were transferred to the hemoximeter sample chamber where they were first saturated with compressed air and then deoxygenated with pure nitrogen. The absorbance at wavelengths that correspond to the isosbestic point (570 nm) and deoxy Hb (560 nm) was recorded as a function of the sample $O_2$ tension ($pO_2$). During deoxygenation, the $pO_2$ and percent $O_2$ saturation values were collected to obtain the OECs and the p50 values (partial pressure of $O_2$ at which Hb is 50% saturated with $O_2$). p50 values were calculated using a non-linear regression analysis.

Microvascular Tissue $PO_2$:

High resolution non-invasive microvascular $PO_2$ measurements were made using phosphorescence quenching microscopy (PQM). Tissue $PO_2$ was measured in regions in between functional capillaries (Yalcin & Cabrales 2012). Hb $O_2$ saturations in the microcirculation are calculated using the $O_2$ equilibrium curves measured.

Tissue Hypoxic Areas:

Tissue hypoxia was studied via immunohistochemistry staining for pimonidazole bound to hypoxic zones in vital tissues. Mice received a bolus intraperitoneal injection (IP) injection of the hypoxic marker Hypoxyprobe-1 (pimonidazole 40 mg/kg) and 5 mg/kg Hoechst 33342 diluted in PBS (total volume, 100 μL). At the end of the study, mice were euthanized and tissues extracted for histology. Sections are stained with monoclonal antibody against pimonidazole. Images for pimonidazole antibody-stained areas and Hoechst were recorded. Results are reported as the ratio of pimonidazole stained area to the total cellular area by co-localization of pimonidazole and Hoechst.

Figure 2A:
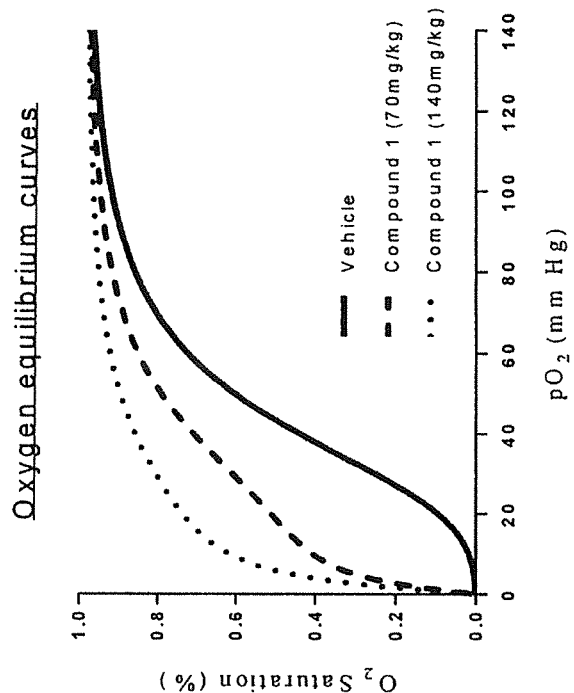
FIG. 2A illustrates the effect of compound 1 on Hb $O_2$ affinity in healthy mice.
Figure 1A:
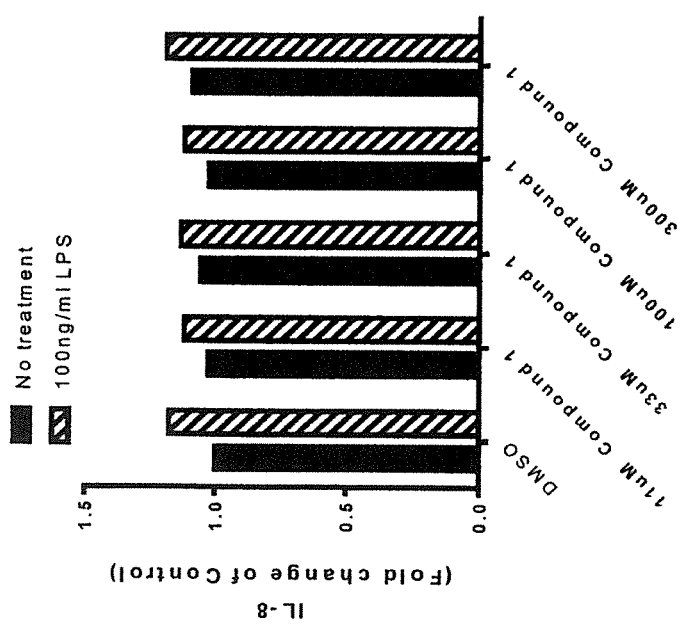

Analysis and Results:

PK/PD Analysis:

Pharmacokinetic analysis of blood from mice dosed with 70 mg/kg or 140 mg/kg of Compound 1 revealed a calculated Compound 1 Hb occupancy of ~30 and 60%, respectively. % Hb occupancy=100×[Compound 1 concentration in blood (mM)]/[(Hct/100)×5 mM]. Hemoximetry was used to determine the PD effect of Compound 1 in whole blood from dosed mice. Representative oxygen equilibrium curves (OECs) of whole blood obtained from mice dosed with Compound 1 (blue and red lines) or vehicle only (black line) are shown in FIG. 2A. The left-shift in the OEC indicates a Compound 1 dose-dependent increase in Hb $O_2$ affinity relative to control (vehicle only).

Figure 2B:
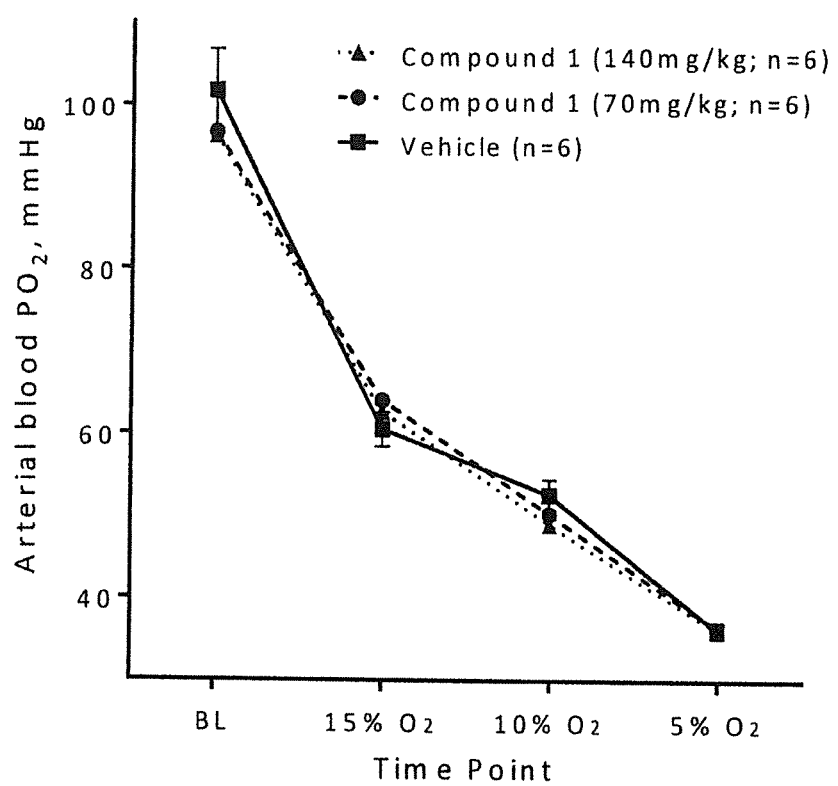
FIGS. 2B and 2C, respectively illustrate the effects of compound 1 on $PaO_2$ and $SaO_2$ during hypoxic challenge.
Figure 2C:
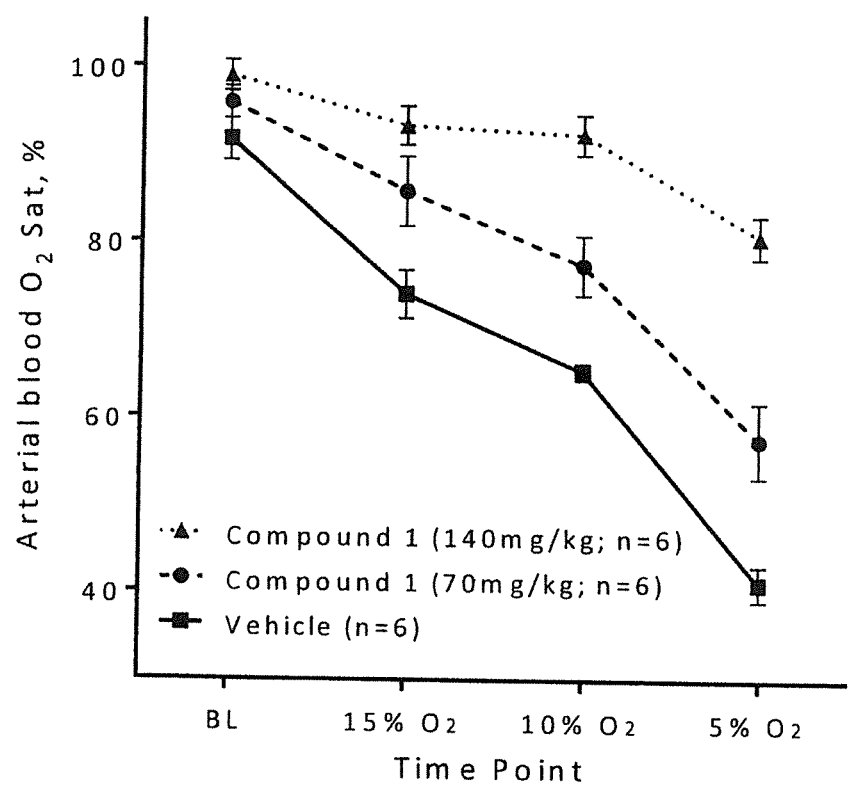

Change in Arterial Blood $O_2$ Saturation:

FIG. 2C depicts the changes $SaO_2$ in response to changes in $PaO_2$ (FIG. 2B) during hypoxia. Arterial blood partial pressure of $O_2$ ($PaO_2$) decreased with increasing level of hypoxia. Since all animals were exposed to the same level of hypoxia, the $PaO_2$ was the same in Compound 1-treated and control mice (FIG. 2B). Arterial blood oxygen saturation ($SaO_2$) decreased with increasing hypoxia. However, Compound 1 dose-dependently increased $SaO_2$ relative to control during hypoxia indicating that Compound 1 increased $O_2$ uptake during hypoxia (FIG. 2C).

Figure 2D:
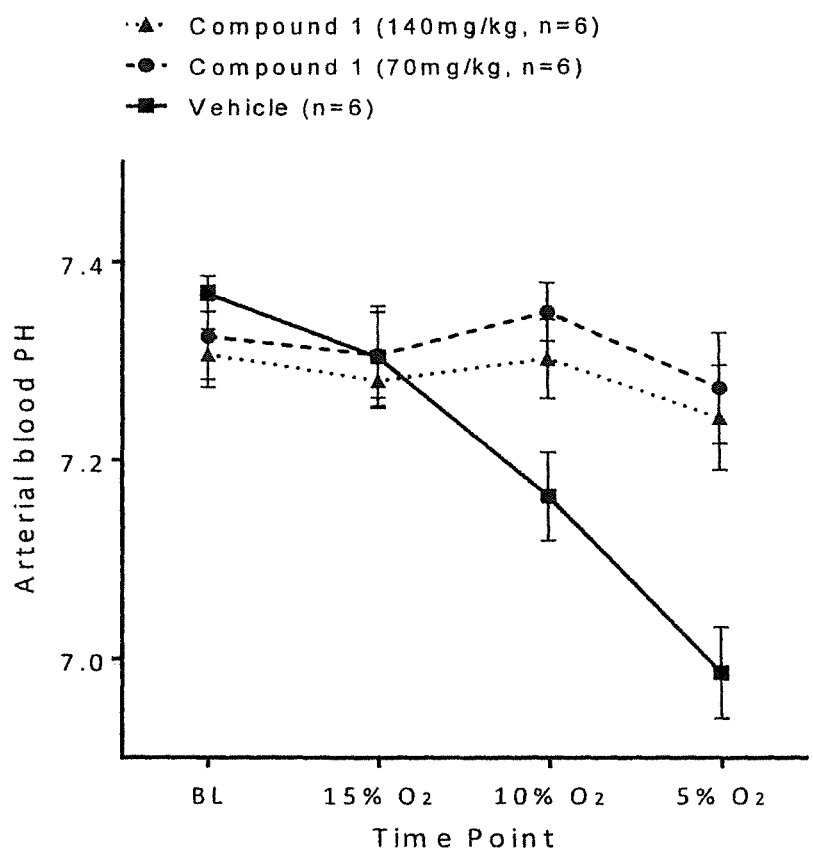
FIGS. 2D and 2E, respectively illustrate the effect of compound 1 on acidosis and blood lactate during hypoxic challenge.
Figure 2E:
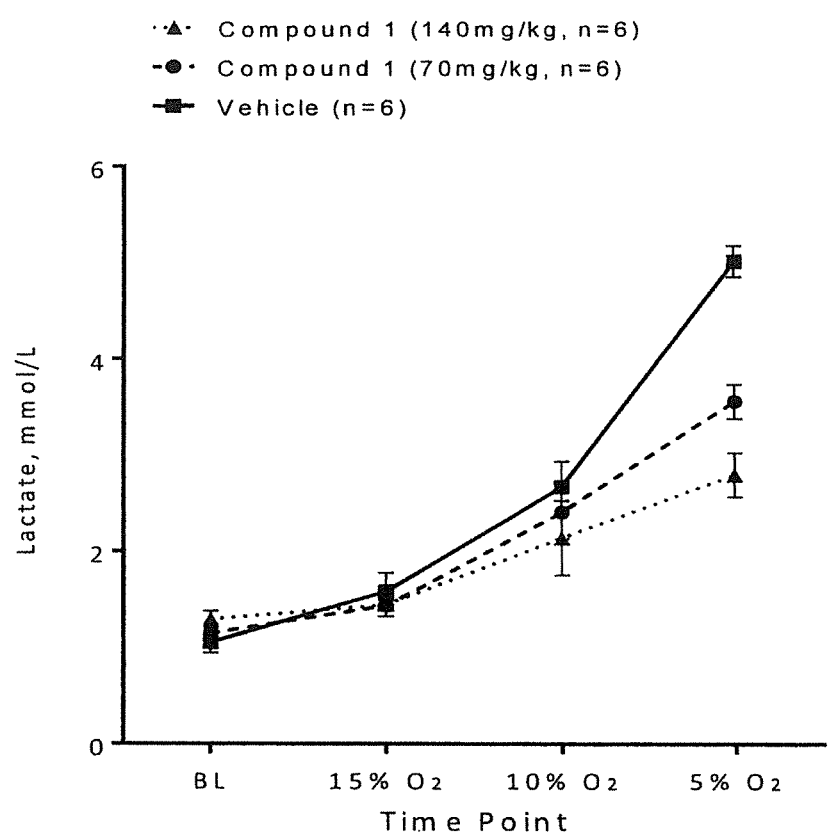

Change in Lactate and pH of Blood During Hypoxia:

FIGS. 2D and 2E shows the changes in lactate and pH of blood during hypoxia. As shown in FIG. 2D, arterial blood pH decreased substantially in control mice during 10% and 5% $O_2$ hypoxia indicating acidosis. In contrast, arterial blood pH was normal during hypoxia in Compound 1 dosed mice indicating that Compound 1 reduced acidosis. In support of this, Compound 1 reduced lactate levels relative to control during extreme hypoxia (5% $O_2$) (FIG. 2E). Thus, by increasing Hb $O_2$ affinity, Compound 1 improved $O_2$ delivery to tissues during hypoxia as evidenced by reduced blood lactate levels relative to control.

Figure 2F:
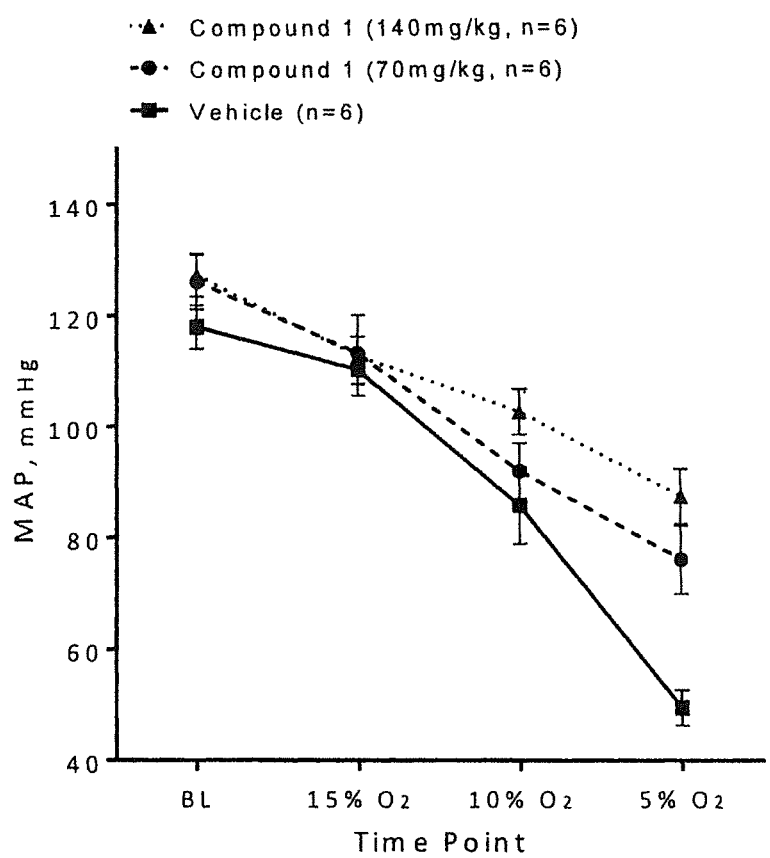
FIGS. 2F and 2G, respectively illustrate the effect of compound 1 on blood pressure and heart rate during hypoxic challenge.
Figure 2G:
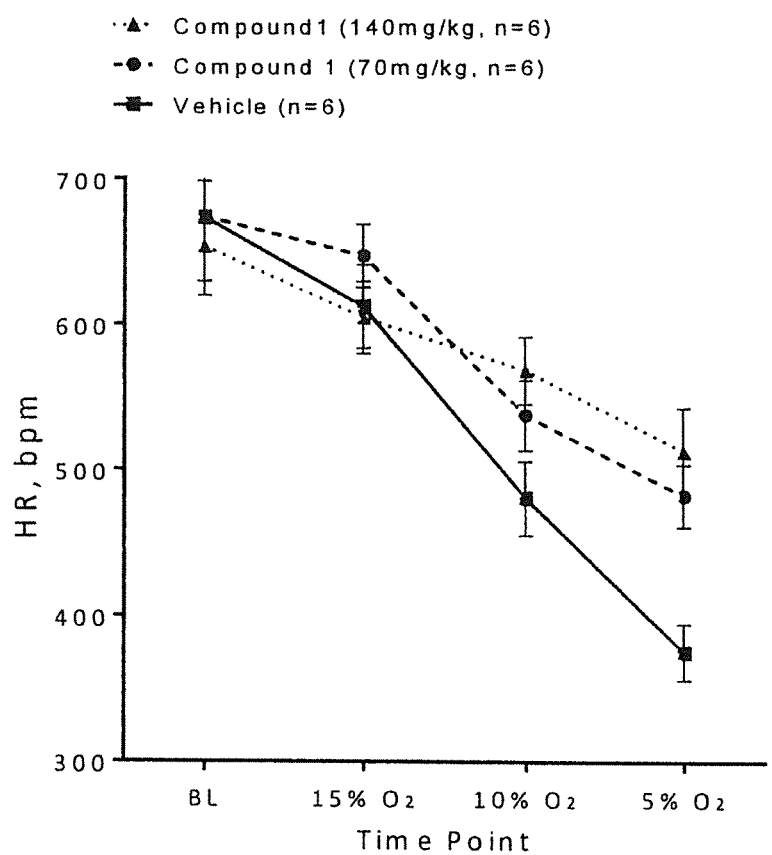

Changes in Mean Arterial Pressure (MAP) and Heart Rate (HR) During Exposure to Hypoxia:

FIGS. 2F and 2G, show changes in mean arterial pressure (MAP) and heart rate (HR) during exposure to hypoxia. During hypoxia MAP and heart rate (HR) decreased in control mice, whereas Compound 1-dosed mice sustained higher mean BP (FIG. 2F) and HR (FIG. 2G) in a dose-dependent fashion. Thus, increased Hb $O_2$ affinity leads to increased $O_2$ delivery to tissues during hypoxia minimizing the systematic the changes in blood pressure and HR necessary to adjust to hypoxia.

Figure 2H:
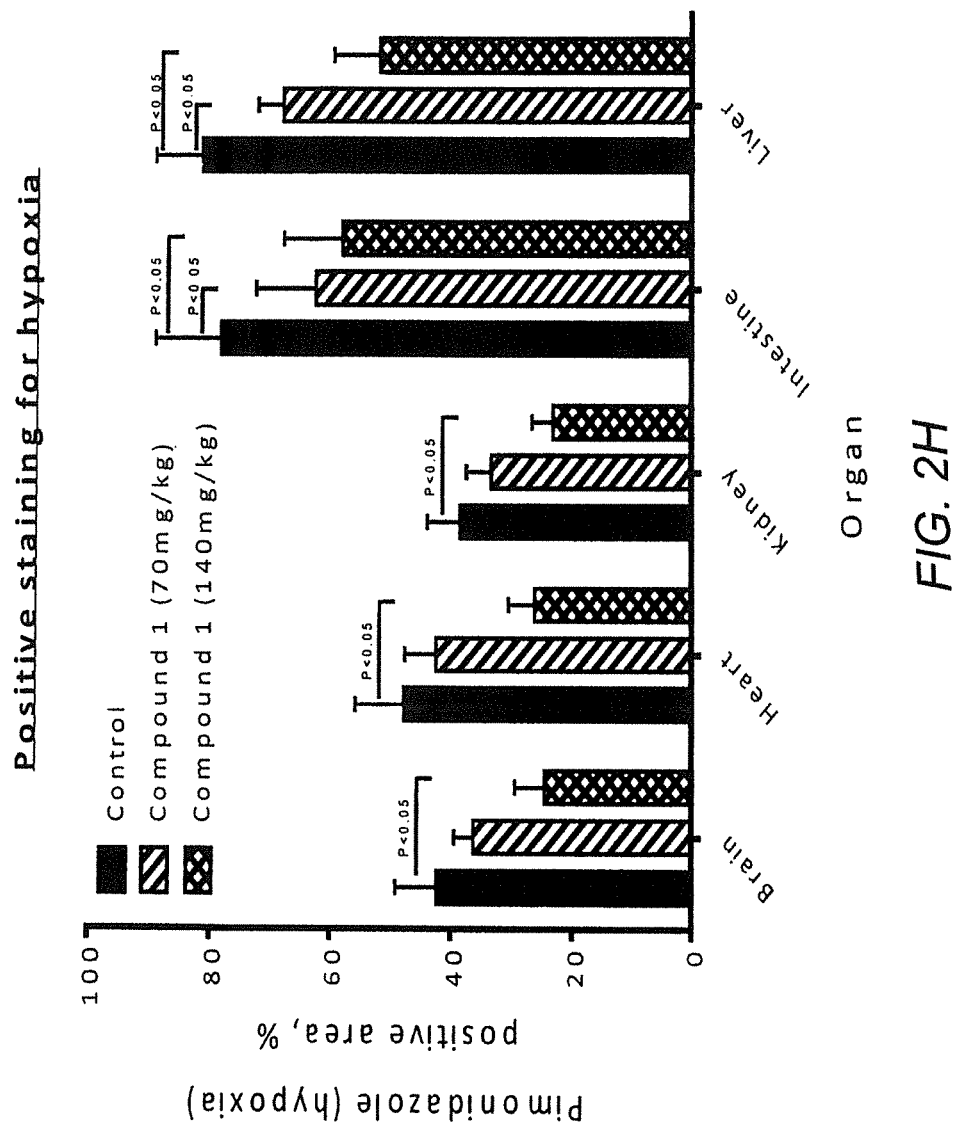
FIGS. 2H and 2I, respectively illustrate the effect of compound 1 on tissue hypoxia and survival during hypoxic challenge.
Figure 2I:
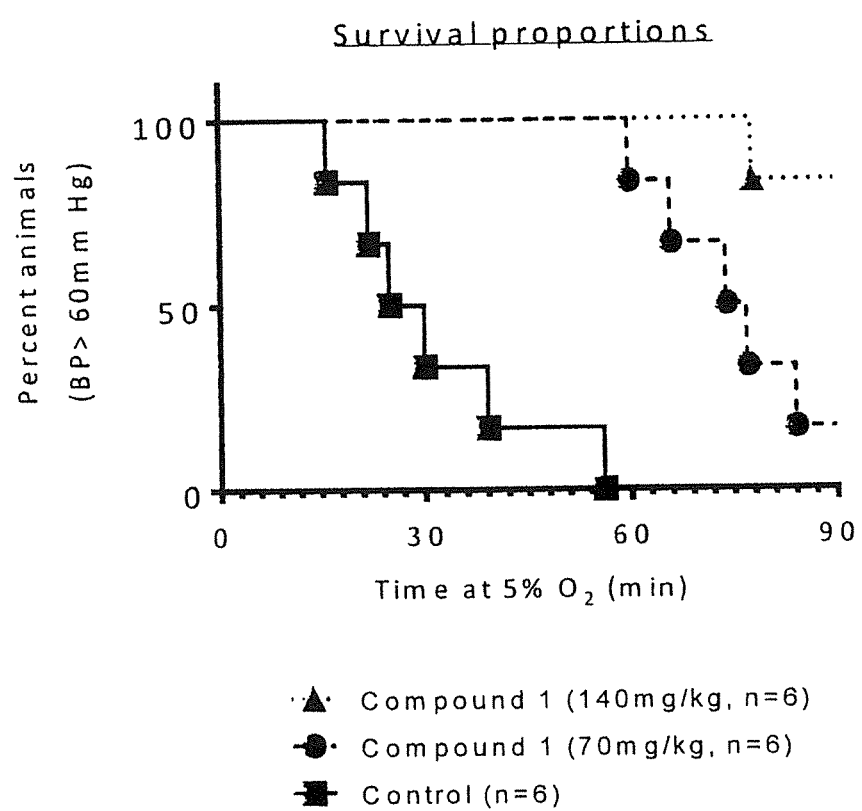

Tissue Hypoxia and Survival:

FIGS. 2H and 2I, respectively show the degree of tissue hypoxia and survival of mice during hypoxia. As shown in FIG. 2H, Compound 1 reduced hypoxic tissues positively stained by pimonidazole relative to control during extreme hypoxia. Moreover, during extreme hypoxia, mice with adequate systolic BP were counted as survived and mice with severe hypotension (BP≤60 mmHg) were counted as non-survived and were euthanized. As shown in FIG. 2I, none of the control mice survived past 1 hour of exposure to 5% $O_2$ hypoxia, whereas 16% of 70 mg/kg Compound 1 dosed mice and 83% of 140 mg/kg Compound 1 dosed mice survived after 1.5 hours of exposure to 5% $O_2$ hypoxia. These data show that Compound 1 improved tissue oxygenation and survival of mice during extreme hypoxia.

This Study demonstrates that a compound that increases the $O_2$ affinity of hemoglobin increases arterial $O_2$ saturation and improves oxygen delivery to tissues during hypoxia. At the tissue level, local milieu allows for efficient $O_2$ extraction leading to improved oxygenation as measured by decreased lactic acidosis, improved cardiovascular function and ultimately, survival.

Example 3

Acute Lung Injury (ALI) Mouse Model

This study was conducted to evaluate the effect of increased Hb $O_2$ affinity on acute hypoxia conditions. In this regard, the effect of Compound 1, that increases Hb $O_2$ affinity, was studied in a mouse model of lipopolysaccharide-induced acute lung injury who were also subjected to extreme hypoxia. This animal model is reproducible and captures the neutrophilic inflammatory response of human ALI/ARDS (Matute-bello, G., Frevert, C. W. & Martin, T. R., 2008. Animal models of acute lung injury). In combination with hypoxic challenge, LPS-induced ALI in animals provides a preclinical model for investigating the effect of potential drugs that may reduce hypoxemia associated with ALI (Matute-bello et al. Id)(Vuichard, D. et al., 2005. Hypoxia aggravates lipopolysaccharide-induced lung injury. *Clinical and Experimental Immunology,* 141(2), pp. 248-260).

Study:

Adult, 8-10-week-old male C57BL/6J mice (Jackson Laboratory, Bar Harbor, Me.), were anesthetized with isoflurane, injected with 100 μg LPS (Sigma, St. Louis, Mo.) in 100 μL PBS by direct intratracheal injection. After 24 hours, mice were given Compound 1 (70 or 140 mg/kg formulated in dimethylacetamide, polyethylene glycol 400 (PEG400) and 40% cavitron in a ratio of 1:5:4, respectively) or vehicle only (5 μL/g) by oral gavage 2 hours prior to placement in a hypoxia chamber. Mice were exposed to either 10 or 5% $O_2$ for 4 hours. Oxygen saturation ($SaO_2$) was measured with a pulse oximeter (STARR Life Sciences, Oakmont, Pa.) at baseline and hourly during hypoxic exposure. During hypoxic exposure, mice were monitored continuously and a moribund check was done every 15 minutes. Time to death was assessed by time to moribund status. Mice were determined to be moribund if they could not right themselves when placed in a supine position.

Blood was collected by cardiac puncture in the hypoxic chamber. Blood gases were measured using the i-STAT portable analyzer within the hypoxic environment (Abaxis, Union City, Calif.). Remaining blood samples were used for hemoximetry and pharmacokinetic analysis. For sample collection, mice were euthanized with pentobarbital overdose. A bronchoaleveolar lavage (BAL) was performed with 900 uL Saline. Blood was collected by retro orbital puncture, and then spun to collect plasma. Lungs were removed and flash frozen. All samples were stored at −80° C. until further study. BAL inflammatory cell counts and differentials were determined manually after staining cytospins with DiffQuik. BAL protein was measured using a Pierce BCA Protein Assay Kit (Thermo Scientific, Waltham, Mass.).

Analysis and Results

Figure 3A:
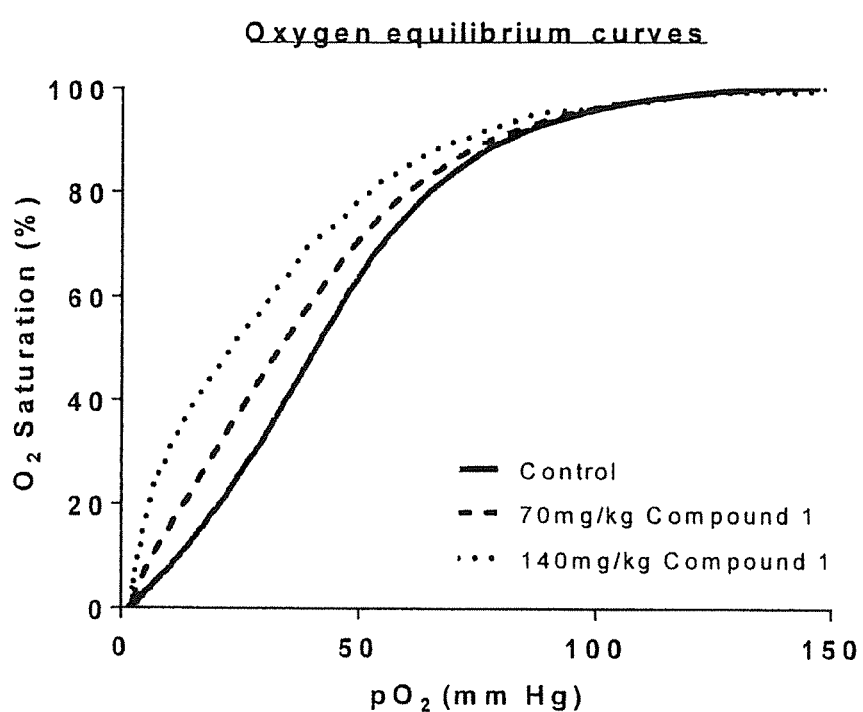
FIG. 3A illustrates the effect of Compound 1 on Hb $O_2$ affinity in mice with LPS-induced ALI.

PK/PD Analysis:

PK analysis of blood from mice dosed with 70 mg/kg or 140 mg/kg Compound 1, revealed Compound 1 Hb occupancy of ~19% and 27%, respectively. % Hb occupancy=100×[Compound 1 concentration in blood (mM)]/[(Hct/100)×5 mM]. Hemoximetry was used to determine the PD effect of Compound 1 in whole blood from dosed mice as described above. Representative oxygen equilibrium curves (OECs) of whole blood obtained from mice dosed with Compound 1 (blue and red lines) or vehicle only (black line) are shown in FIG. 3A. The left-shift in the OEC indicates a Compound 1 dose-dependent increase in Hb $O_2$ affinity relative to control (vehicle only).

Figure 3C:
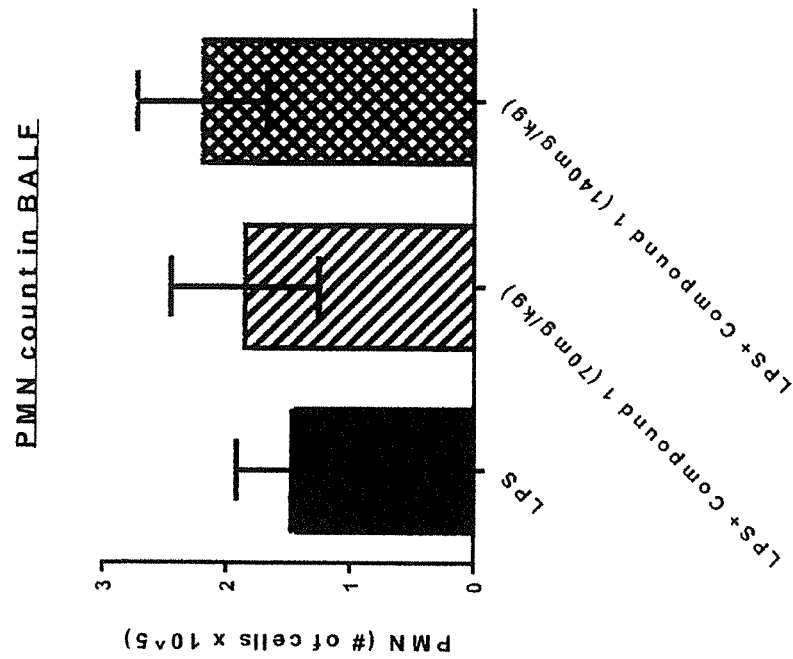
FIGS. 3B, 3C, 3D and 3E illustrate the effect of Compound 1 on inflammation induced by intratracheal administration of LPS.
Figure 3B:
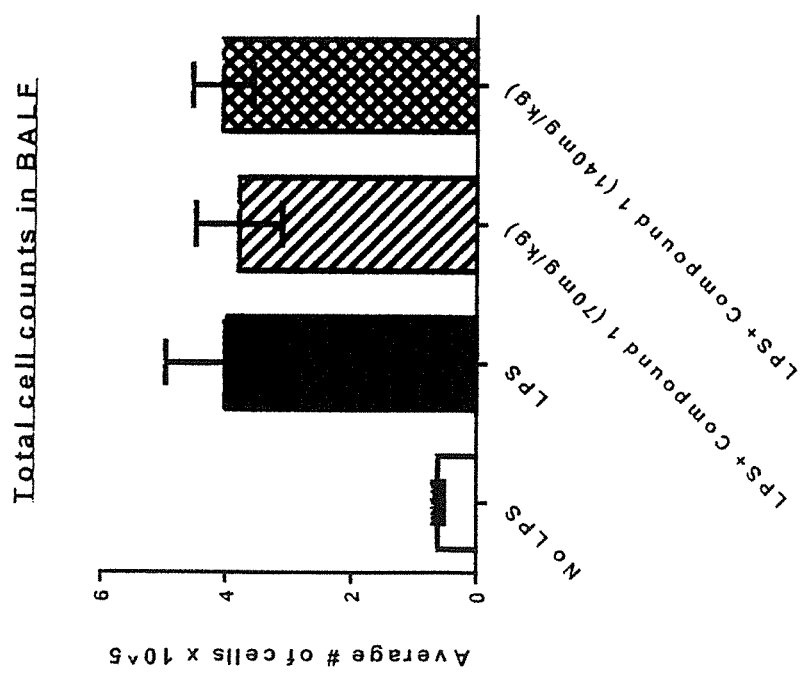
Figure 3E:
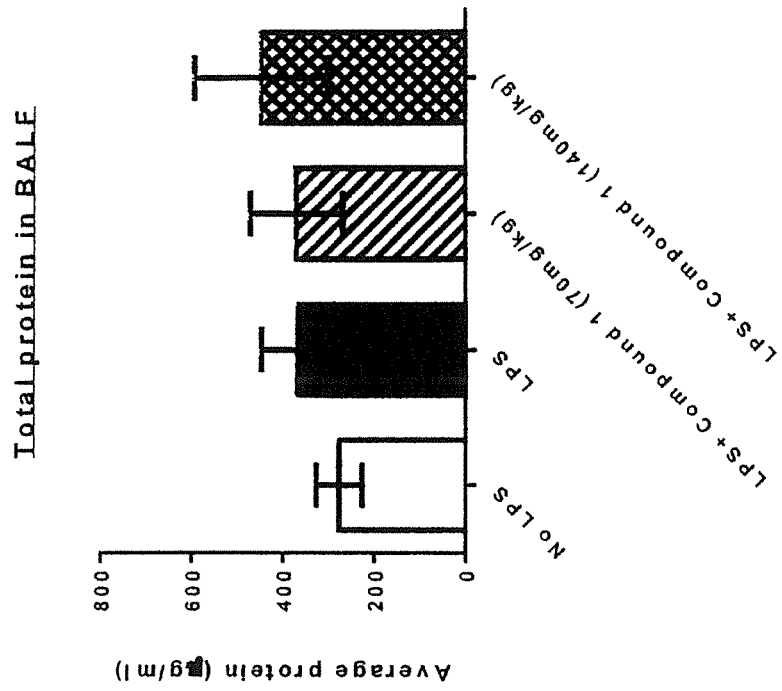
Figure 3D:
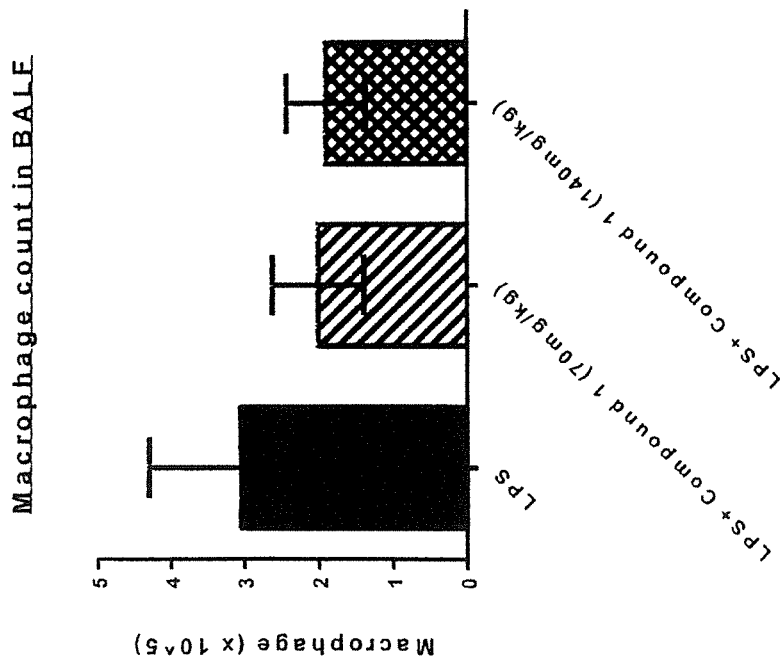

LPS Induced Lung Injury:

Treatment with 100 μg LPS induced inflammation as evidenced by increased total cell counts in BALF relative to No LPS control group (FIG. 3B). Moreover, BALF from LPS treated animals contained neutrophils (FIG. 3C) and macrophages (FIG. 3D) which are typical inflammatory markers consistent with LPS-induced lung injury. However, no major differences in total protein were observed in BALF of LPS-treated versus (No LPS) control groups (FIG. 3E), confirming the absence of significant alveolar capillary damage in this model of acute lung injury. Compound 1 had no significant effect on inflammation or lung injury.

Figure 3F:
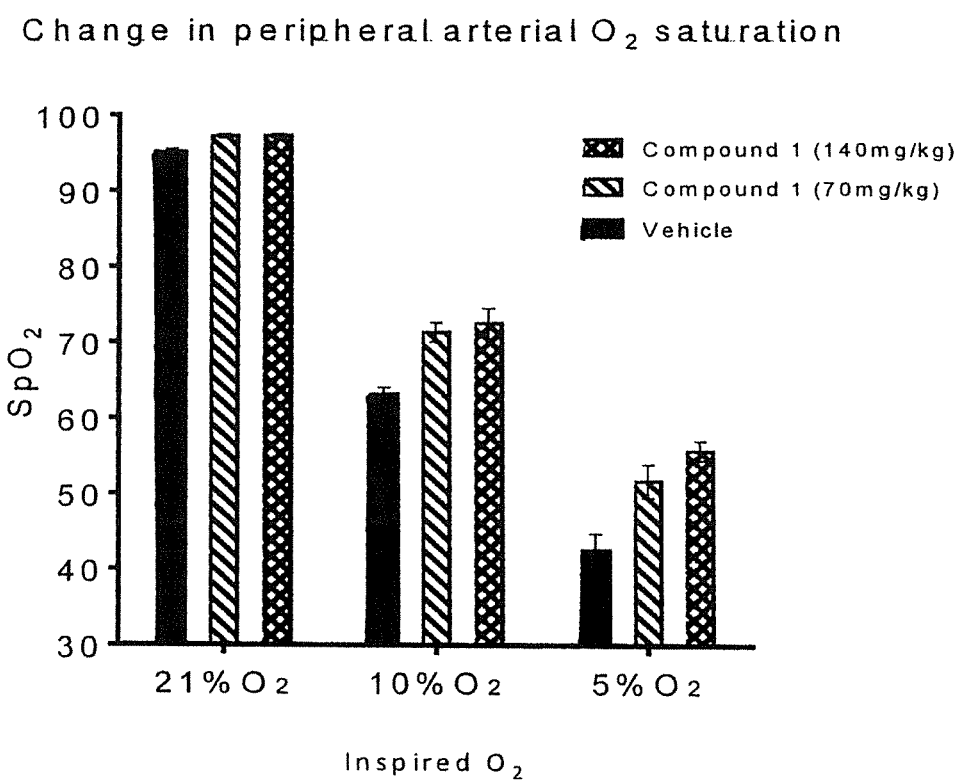
FIG. 3F illustrates the effect of Compound 1 on peripheral arterial $O_2$ saturation in mice with LPS-induced ALI.

Change in Peripheral Arterial $O_2$ Saturation:

Using a MouseOx, peripheral arterial $O_2$ saturation ($SpO_2$) was measured during hypoxia. $SpO_2$ was measured for each group every hour during hypoxia. Average $SpO_2$ during 4 hours of exposure to hypoxia for each group are shown in FIG. 3F. In general, $SpO_2$ decreased during hypoxia for all groups. However, during 10% and 5% $O_2$ hypoxia, $SpO_2$ was higher in Compound 1 dosed mice compared to control (or vehicle) mice. For example, during 5% $O_2$ hypoxia, Compound 1 at 70 mg/kg or 140 mg/kg increased $SpO_2$ by 22% or 31% of control value, respectively. Thus Compound 1 increased $SpO_2$ relative to control during hypoxia indicating that Compound 1 increased $O_2$ uptake during hypoxia in the presence of acute lung injury.

Figure 3G:
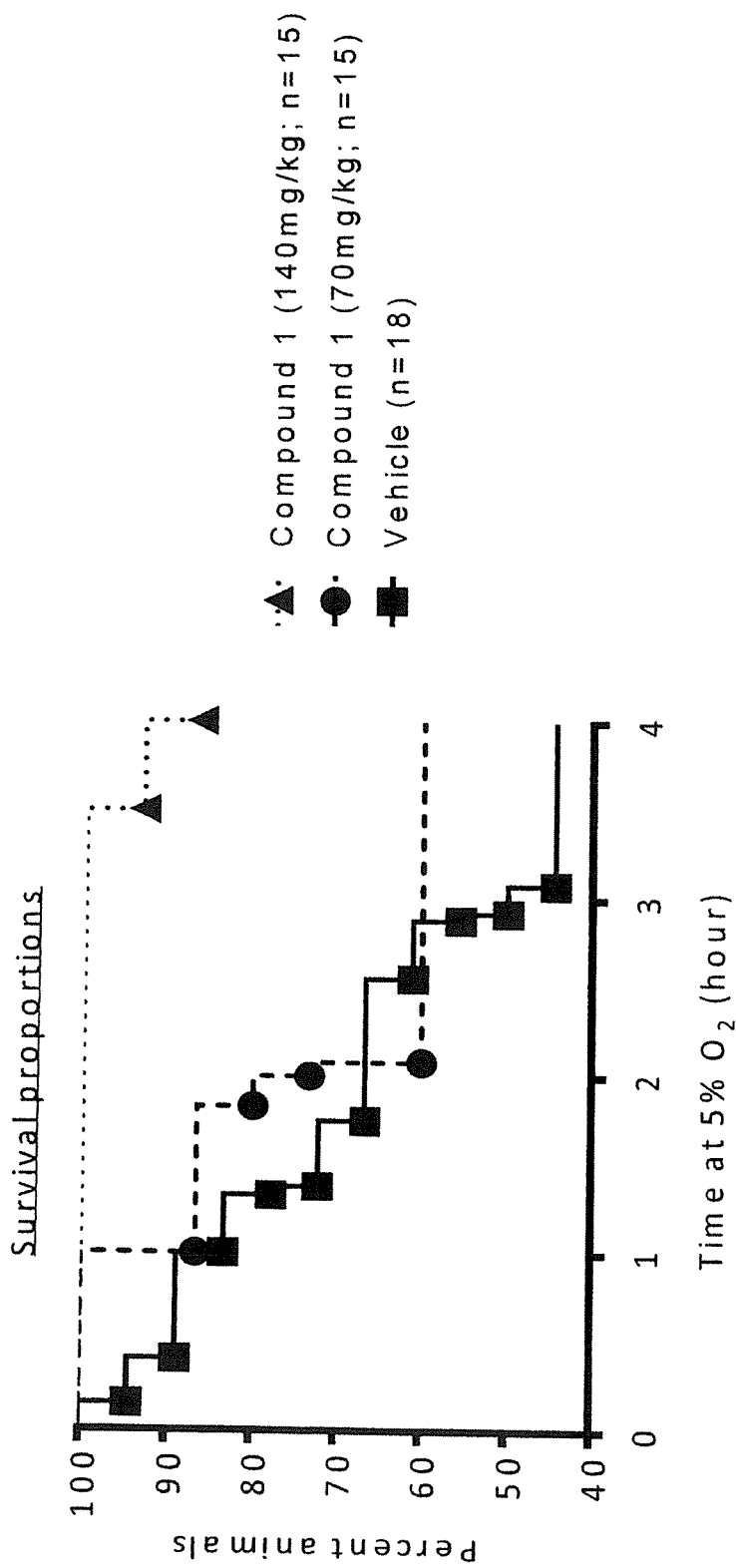
FIG. 3G illustrates the effect of Compound 1 on survival in mice with LPS-induced ALI.

Survival:

During exposure hypoxia, mice were monitored continuously and a moribund check was done every 15 minutes. Time to death was assessed by time to moribund status. Mice were determined to be moribund if they could not right themselves when placed in a supine position. As shown in FIG. 3G, 45% of control mice survived after 4 hours of exposure to 5% $O_2$ hypoxia, whereas 60% of 70 mg/kg Compound 1 dosed mice and 86% of 140 mg/kg Compound 1 dosed mice survived. Thus Compound 1 dose-dependently improved survival of mice with acute lung injury during exposure to extreme hypoxia.

This study demonstrates that a compound that increases the $O_2$ affinity of hemoglobin improves $O_2$ uptake and $O_2$ delivery to tissue during hypoxia in the presence of lung injury and thereby provides a new therapeutic strategy for improving $O_2$ delivery and minimizing the need for excessive $O_2$ which often further aggravates lung injury.

Example 4

Bleomycin Induced Mouse Model of Hypoxemia and Pulmonary Fibrosis

This study was conducted to evaluate whether increased Hb $O_2$ affinity could ameliorate hypoxia associated with IPF. Compound 1 was evaluated in a bleomycin induced mouse model of hypoxemia and fibrosis. Bleomycin induced pulmonary fibrosis in animals provides a preclinical model for investigating the effect of potential drugs that may reduce hypoxemia associated with IPF. In this study, hypoxemia was determined by monitoring arterial oxygen saturation ($SaO_2$), while the severity of pulmonary fibrosis was assessed by histopathologic evaluation and determination of collagen and leukocyte levels in bronchoalveolar lavage fluid (BALF).

Study:

Forty-eight C57B/L6 male mice aged 7-8 weeks were obtained from Simonsen Laboratory, Gilroy, Calif. The mice were ear tagged and weighed prior to the start of the study. The animals were distributed into four groups with twelve animals in each group. Body weights of all mice were recorded daily during the study. Animals in groups 2, 3 and 4 were administered 3 U/kg bleomycin sulfate USP (Teva Pharmaceuticals) via oropharyngeal route for 7 days (see Walters, D. M. and S. R. Kleeberger (2008). "Mouse models of bleomycin-induced pulmonary fibrosis." *Curr Protoc Pharmacol Chapter* 5: Unit 5 46.) Animals in group 1 were administered normal saline via oropharyngeal route.

Compound 1 (formulated in dimethylacetamide: polyethylene glycol 400 (PEG400): 40% cavitron at a 1:5:4 ratio) was administered at either low dose (first day 50 mg/kg followed by 40 mg/kg daily) or high dose (first day 150 mg/kg followed by 85 mg/kg daily) via oral gavage to bleomycin treated mice once daily from day 8 to day 15. Animals in group 1 were administered vehicle via oral gavage. The dosing volume was 200 µL. The study animals were sacrificed on day 15 at 4 hours post final dose.

Samples for hemoximetry and pharmacokinetics (PK) were taken 4 hours following the last dose of the dosing regimen. BAL fluid was collected from the lungs of the animals by lavaging the lung with 1 ml Hanks balanced salt media (HBSS). Lungs were harvested from each animal and weighed. They were then inflated by ~0.5 mL of 10% NBF and fixed in a formalin container for subsequent histopathological analysis.

Analysis and Results:
PK/PD:
PK:

Compound 1 blood and plasma concentrations were determined by LC-MS 4 hours after the last dose. Both standard and QC blood samples were pre-incubated at 37° C. for 1 hr. After incubation, all standard and QC samples were diluted with 2-fold volume of water to match with the condition of samples. Plasma standard and QC were proceeding without pre-incubation. For all samples, 10 µL of blood or plasma sample were mixed with 240 µL of sodium citrate buffer (pH 3) in a 2-mL 96 well plate. The mixture was vortexed for 10 minutes. An internal standard, 500 µL of 200 ng/mL 2-hydroxy-6-((2-(1-(propan-2-yl-$d_7$)-1H-pyrazol-5-yl)pyridin-3-yl)methoxy)benzaldehyde) in acetonitrile, was added to all samples and the mixture was vortexed for 20 minutes. The sample plate was centrifuged at 4000 rpm for 10 minutes. Ten µL of supernatant was transferred to an injection plate and diluted with 190 µL of 50% acetonitrile in water before injecting to the LCMS. Compound 1 and 2-hydroxy-6-((2-(1-(propan-2-yl-$d_7$)-1H-pyrazol-5-yl)pyridin-3-yl)methoxy)benzaldehyde were separated on a Thermo Aquasil C18 column (2.1×20, 5 µm). A mobile phase gradient was programmed with mixture of 85% mobile phase A (0.1% formic acid in water) and 15% mobile phase B (0.1% formic acid in 100% acetonitrile) from 0.0-0.5 min, changed to 95% mobile phase B from 0.5-1.5 minutes, hold at 95% mobile phase B from 1.5-1.8 min. At 1.9 min, the mobile phase went back to 15% mobile phase B and remained there from 1.9-2.5 min. The peak area of m/z 341->203 product ion (Compound 1) was measured against that of the m/z 345->159 product ion 2-hydroxy-6-((2-(1-(propan-2-yl-$d_7$)-1H-pyrazol-5-yl)pyridin-3-yl)methoxy)benzaldehyde in positive ion mode. The analytical range was 50 to 100000 ng/mL for blood sample and 50 to 5000 ng/mL for plasma sample. The bleomycin treated mice with the low and high dose regimens of Compound 1 achieved 18.0% and 36.7% of calculated Hb occupancy, respectively. The average blood/plasma concentration ratio was 22:1 which is equivalent to RBC/plasma ratio of 102:1. The high RBC/plasma ratio of Compound 1 indicated a preferential partitioning of Compound 1, into the red blood cells (Table 12).

Figure 4B:
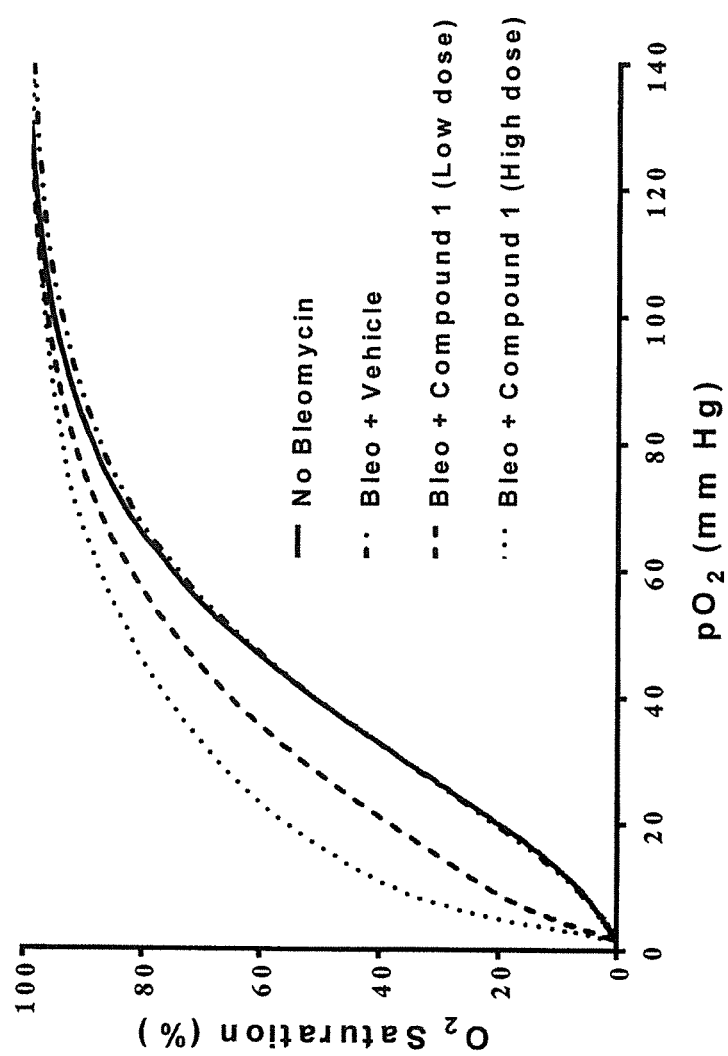
FIG. 4B illustrates the PD effects of Compound 1 in mice with bleomycin-induced fibrosis.

Hemoglobin Occupancy:

Hemoglobin occupancy by Compound 1 was calculated by dividing the concentration of Compound 1 in RBCs by the Hb concentration in RBCs (5 mM). RBC was calculated from whole blood and plasma concentration data using the following equation:

$$RBC = \frac{C_b - [(1 - Hct) * C_p]}{Hct}$$

here $C_b$=Blood concentration of Compound 1 in µg/mL
$C_b$=Plasma concentration of Compound 1 Compound 1 in µg/mL
Hct=Hematocrit value (0.21) Hemoximetry
PD Hemoximetry measurements (PD analysis) were conducted in a Hemox Analyzer (TCS Scientific Corporation, New Hope, Pa.). The samples were transferred to the hemoximeter sample chamber where they were first saturated with compressed air and then deoxygenated with pure nitrogen. The absorbance at wavelengths that correspond to the isosbestic point (570 nm) and deoxy Hb (560 nm) was recorded as a function of the sample $O_2$ tension ($pO_2$). During deoxygenation, the $pO_2$ and percent $O_2$ saturation values were collected to obtain the OECs and the p50 values (partial pressure of $O_2$ at which Hb is 50% saturated with $O_2$). p50 values are calculated using a non-linear regression analysis. As shown in FIG. 4B, mice treated with Compound 1 demonstrated a significant left shift in the OEC in a dose-response manner indicating a higher Hb-oxygen binding affinity.

Figure 4C:
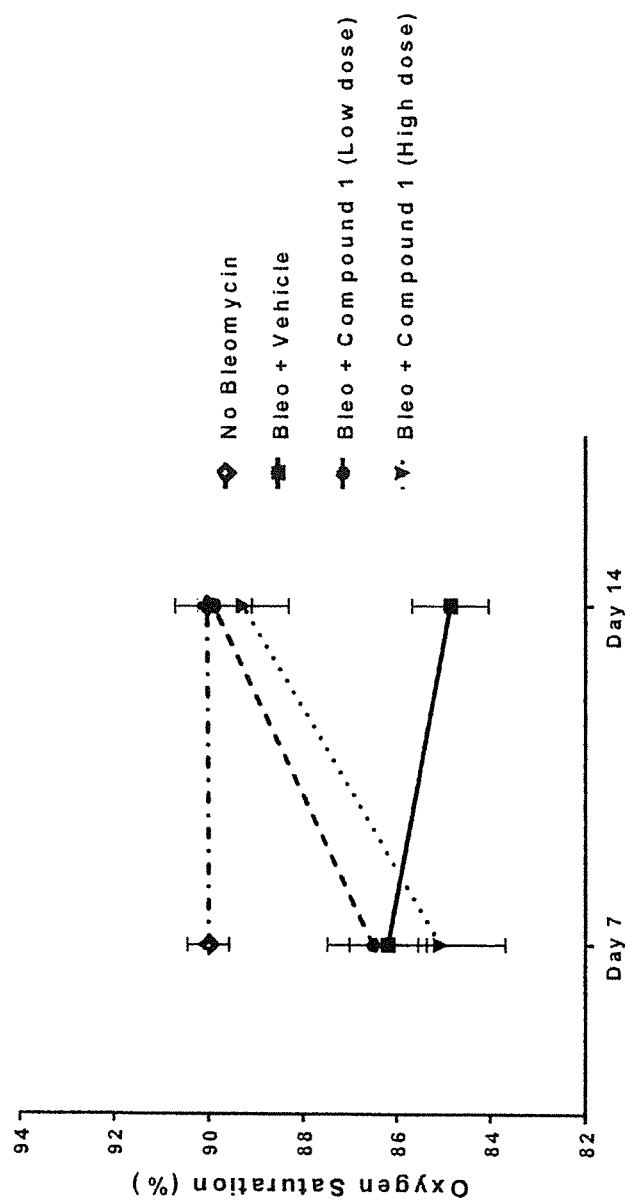
FIGS. 4C and 4D illustrate the effect of Compound 1 on $O_2$ saturation in mice with bleomycin-induced fibrosis.
Figure 4D:
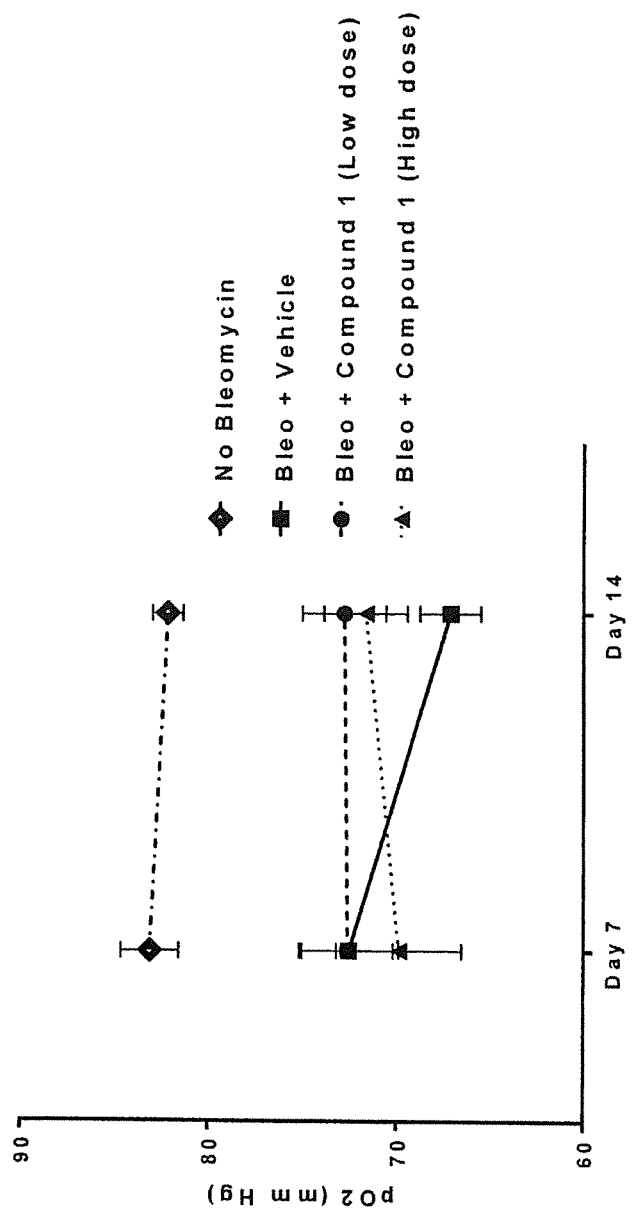

Arterial Blood Gases and Oxygen Saturation:

Hypoxia is a feature of IPF, and oxygen saturation measurements are often used clinically to evaluate the presence and severity of hypoxia. Responses to hypoxia in mice treated with Compound 1 were first evaluated by measuring arterial oxygen saturation ($S_aO_2$). On day 7 and 14 after bleomycin or saline instillation, 50 µL of arterial blood from the tail artery were used for measurement of arterial oxygen saturation ($S_aO_2$) using whole blood GEM OPL co-oximeter (Instrumentation Laboratory, MA). An additional aliquot of 100 µL of blood were collected from tail artery and arterial blood gases using the i-STAT Handheld Blood Analyzer (ABBOTT) were measured using CG4+ cartridges. For each mouse, $S_aO_2$ and arterial oxygen tension (pO2) were measured. As shown in FIG. 4C, both Compound 1-treated groups showed a decrease of $S_aO_2$ before Compound 1 treatment on day 7 and subsequent return toward control values following treatment with Compound 1 for seven consecutive days (Low dose: Day 8 50 mg/kg; Day 9-15 40 mg/kg daily; High dose: Day 8 150 mg/kg; Day 9-15 85 mg/kg daily). In contrast, arterial oxygenation levels of vehicle treated mice further declined throughout the study (FIG. 4C). The arterial blood gases (ABG) were also analyzed on day 7 and day 14 (FIG. 4C). Data are expressed as means±SEM. At day 7, in bleomycin treated mice, arterial oxygen tension ($pO_2$) was significantly decreased, indicating an impairment of pulmonary gas exchange. In vehicle-treated bleomycin mice the $pO_2$ reached a further decline at day 14. Compound 1 treatment showed a tendency for an increase $pO_2$ or prevention of further decline of $pO_2$, suggesting a beneficial effect on disease progression (FIG. 4D). Collectively, these findings demonstrate that Compound 1 treatment significantly improve hypoxemia, leading to physiologic improvement in mice.

BAL Fluid Leukocyte Analysis:

In this bleomycin model, mice develop extensive pulmonary fibrosis as well as pulmonary inflammation; thus, the effect of Compound 1 treatment on the phenotype of pulmonary inflammatory cells was examined. The BAL fluid was centrifuged at 1,000 rpm at 4° C. for 5 minutes. The BAL cell pellets were suspended in 2 mls of 1× Pharmalyse buffer (BD Bioscience) to lyse the RBCs. PBS+2% FBS were added to stop the lysis reaction and cells centrifuged again. Leukocytes in the cell pellet were counted using a hemocytometer and the trypan blue exclusion method.

Figure 4E:
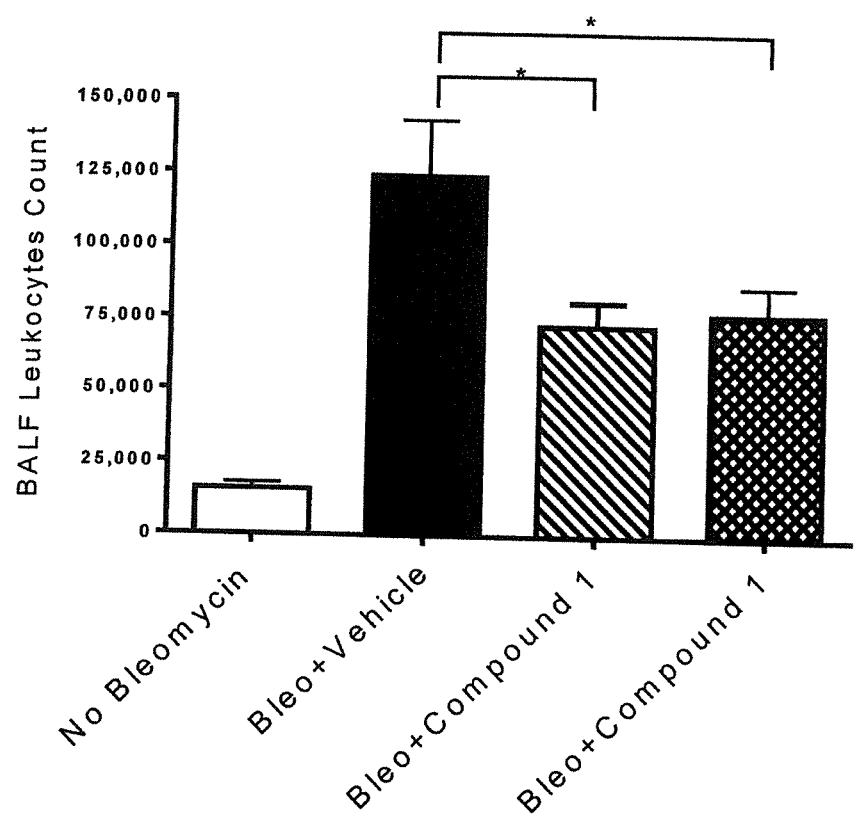
FIG. 4E illustrates the effect of Compound 1 on leukocyte infiltration in mice with bleomycin-induced fibrosis.

Treatment with Compound 1 was associated with decreased inflammation, as evident by a significant reduction in total inflammatory cells recovered in BAL fluid on day 15 (*, P<0.05; Low dose: Day 8 50 mg/kg; Day 9-15 40 mg/kg daily; High dose: Day 8 150 mg/kg; Day 9-15 85 mg/kg daily) (FIG. 4E). This finding demonstrates that Compound 1 treatment attenuates pulmonary inflammation in this model.

Figure 4F:
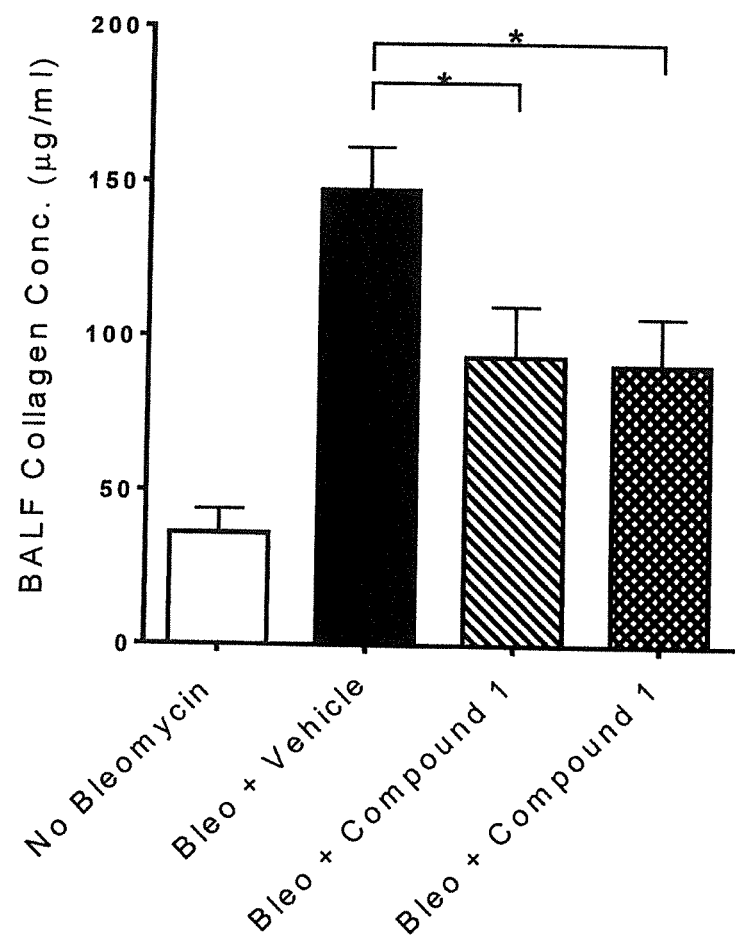
FIG. 4F illustrates the effect of Compound 1 on collagen deposition in mice with bleomycin-induced fibrosis.

BAL Fluid Collagen Analysis:

In addition to anti-hypoxemia and anti-inflammatory effects, Compound 1 treatment showed improvement in the fibrotic lesions. Pulmonary fibrosis was induced by administering mice a single dose of bleomycin. Collagen content of was determined by quantifying total soluble collagen in the BALF supernatant using the Sircol collagen dye binding assay according to the manufacturer's instructions (Biocolor Ltd, Carrick Fergus, UK). Compound 1 treatment resulted in a significant reduction in collagen protein in the lungs (*, P<0.05; Low dose: Day 8 50 mg/kg; Day 9-15 40 mg/kg daily; High dose: Day 8 150 mg/kg; Day 9-15 85 mg/kg daily) (FIG. 4F). These results indicate that Compound 1 attenuates pulmonary fibrosis in the bleomycin murine model.

Figure 4G:
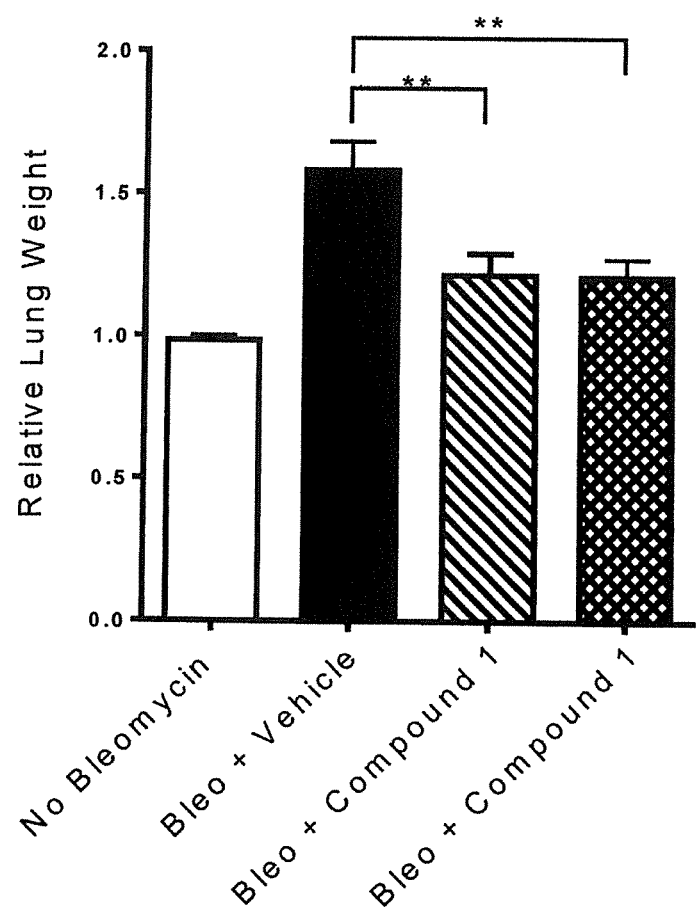
FIG. 4G illustrates the effect of Compound 1 on lung weight of mice with bleomycin-induced fibrosis.

Measurement of Lung Weight:

Lungs were harvested from each animal and weighed at Day 15. The lungs of bleomycin mice administered with vehicle control were significantly heavier than lungs from Compound 1-treated mice (**, P<0.01), suggestive of reduced fibrotic disease in treated animals (FIG. 4G). These results confirm that Compound 1 attenuates pulmonary fibrosis in the bleomycin murine model.

Histopathological Analysis:

The histopathological analysis was conducted at Seventh Wave Laboratories, Chesterfield, Mo. The lung samples were processed and embedded with all lobes from each mouse in one paraffin block. Coronal sections through the four major lobes were stained with Masson's Trichrome. For each animal, consecutive lung fields were examined in a raster pattern using a 20× objective lens and a 10× or 40× ocular lens (200× or 800×). A modified Ashcroft score (Hubner et al. 2008) was recorded for each field. The fibrotic index was calculated as the sum of the modified Ashcroft field scores divided by the number of fields examined.

Figure 4H:
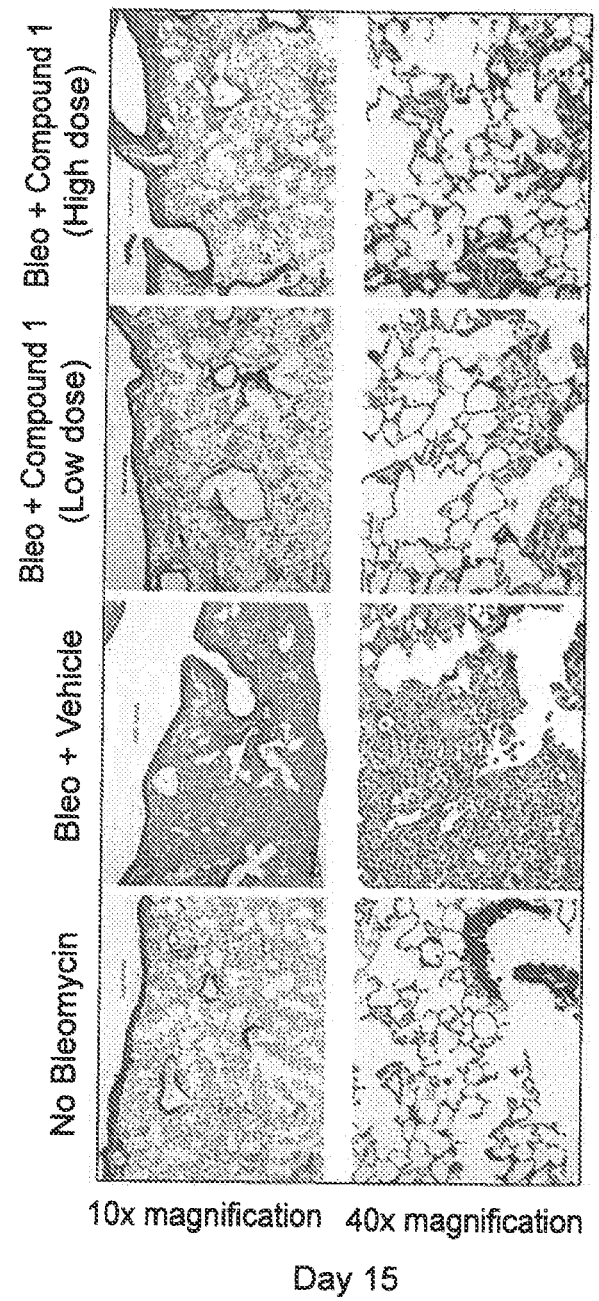
FIGS. 4H and 4I illustrate the effect of Compound 1 on fibrosis in mice treated bleomycin-induced fibrosis.
Figure 4I:
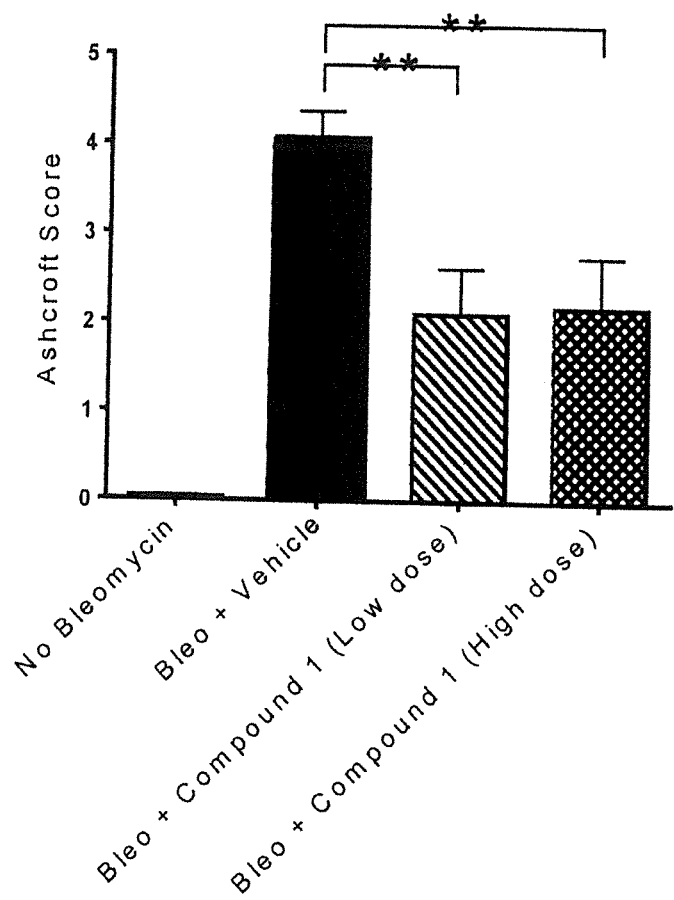

Lung sections from day 15 mice were stained with Masson's trichrome to visualize collagen deposition (blue). Vehicle treated bleomycin lungs were fibrotic and had extensive collagen deposition, thickened pulmonary interalveolar septum and obliteration of the alveolar airspaces by collagen (FIG. 4H). In contrast, Compound 1-treated lungs (Low dose: Day 8 50 mg/kg; Day 9-15 40 mg/kg daily; High dose: Day 8 150 mg/kg; Day 9-15 85 mg/kg daily) showed diminished collagen deposition; many alveoli did not exhibit septal fibrosis and resembled the parenchyma in lungs without bleomycin exposure (FIG. 4H). Ashcroft scoring to quantify morphologic fibrosis was performed, and Compound 1 treatment improved overall scores by approximately 50% (**, P<0.01; FIG. 4I). These results suggest that Compound 1 inhibits pulmonary fibrosis in this bleomycin mouse model.

It should be understood that other compounds as described herein can be similarly evaluated as described above.

The disclosure has been described broadly and generically herein. Each of the narrower species and subgeneric groupings falling within the generic disclosure also form part of the invention. In addition, where features or aspects of the invention are described in terms of Markush groups, those skilled in the art will recognize that the invention is also thereby described in terms of any individual member or subgroup of members of the Markush group.

The invention claimed is:

1. A compound selected from:

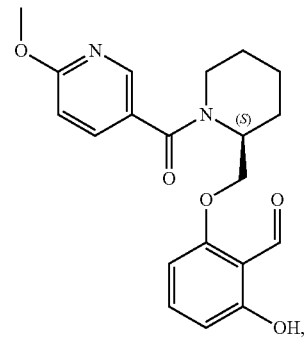

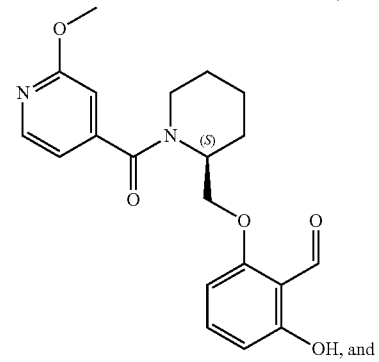

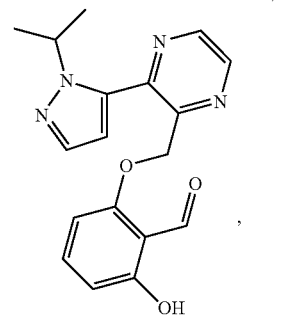

or a stereoisomer thereof, or a pharmaceutically acceptable salt of each thereof.

2. A pharmaceutical composition comprising a compound of claim 1, or a stereoisomer thereof, or a pharmaceutically acceptable salt of each thereof, and at least one pharmaceutically acceptable excipient.

3. The compound of claim 1, which is

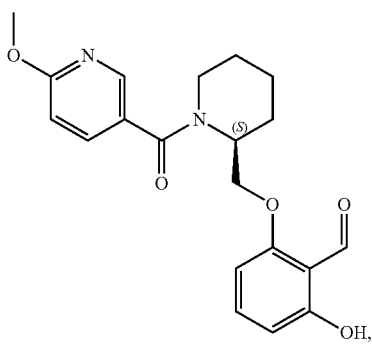

or a stereoisomer thereof, or a pharmaceutically acceptable salt of each thereof.

4. The compound of claim 1, which is

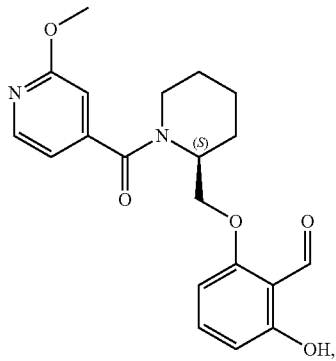

or a stereoisomer thereof, or a pharmaceutically acceptable salt of each thereof.

5. The compound of claim 1, which is

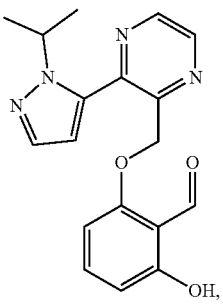 [SMILES: CC(C)n1nccc1-c1nccnc1COc1cccc(O)c1C=O]

or a stereoisomer thereof, or a pharmaceutically acceptable salt of each thereof.

6. A pharmaceutical composition comprising the compound of claim 3, or a stereoisomer thereof, or a pharmaceutically acceptable salt of each thereof, and at least one pharmaceutically acceptable excipient.

7. A pharmaceutical composition comprising the compound of claim 4, or a stereoisomer thereof, or a pharmaceutically acceptable salt of each thereof, and at least one pharmaceutically acceptable excipient.

8. A pharmaceutical composition comprising the compound of claim 5, or a stereoisomer thereof, or a pharmaceutically acceptable salt of each thereof, and at least one pharmaceutically acceptable excipient.

9. A method for increasing hemoglobin oxygen affinity in a human in need thereof comprising administering to the human a compound of claim 1, or a stereoisomer thereof, or a pharmaceutically acceptable salt of each thereof.

10. The method of claim 9, wherein the hemoglobin is hemoglobin S.

11. A method for increasing hemoglobin oxygen affinity in a human in need thereof comprising administering to the human the compound of claim 3, or a stereoisomer thereof, or a pharmaceutically acceptable salt of each thereof.

12. A method for increasing hemoglobin oxygen affinity in a human in need thereof comprising administering to the human the compound of claim 4, or a stereoisomer thereof, or a pharmaceutically acceptable salt of each thereof.

13. A method for increasing hemoglobin oxygen affinity in a human in need thereof comprising administering to the human the compound of claim 5, or a stereoisomer thereof, or a pharmaceutically acceptable salt of each thereof.

14. A method for treating sickle cell disease in a human in need thereof comprising administering to the human a compound of claim 1, or a stereoisomer thereof, or a pharmaceutically acceptable salt of each thereof.

15. A method for treating sickle cell disease in a human in need thereof comprising administering to the human the compound of claim 3, or a stereoisomer thereof, or a pharmaceutically acceptable salt of each thereof.

16. A method for treating sickle cell disease in a human in need thereof comprising administering to the human the compound of claim 4, or a stereoisomer thereof, or a pharmaceutically acceptable salt of each thereof.

17. A method for treating sickle cell disease in a human in need thereof comprising administering to the human the compound of claim 5, or a stereoisomer thereof, or a pharmaceutically acceptable salt of each thereof.

* * * * *